US009957514B2

(12) United States Patent
Martienssen et al.

(10) Patent No.: US 9,957,514 B2
(45) Date of Patent: May 1, 2018

(54) TRANSFORMATION OF DUCKWEED AND USES THEREOF

(71) Applicants: Cold Spring Harbor Laboratory, Cold Spring Harbor, NY (US); Brookhaven Science Associates, LLC, Upton, NY (US)

(72) Inventors: Rob Martienssen, Cold Spring Harbor, NY (US); Almudena Molla-Morales, New York, NY (US); Alex Cantó-Pastor, New York, NY (US); Evan Ernst, New York, NY (US); John Shanklin, Shoreham, NY (US); Yiheng Yan, Athens, GA (US)

(73) Assignees: Cold Spring Harbor Laboratory, Cold Spring Harbor, NY (US); Brookhaven Science Associates, LLC, Upton, NY (US)

( * ) Notice: Subject to any disclaimer, the term of this patent is extended or adjusted under 35 U.S.C. 154(b) by 0 days. days.

(21) Appl. No.: 14/913,057

(22) PCT Filed: Aug. 21, 2014

(86) PCT No.: PCT/US2014/052182
§ 371 (c)(1),
(2) Date: Feb. 19, 2016

(87) PCT Pub. No.: WO2015/027109
PCT Pub. Date: Feb. 26, 2015

(65) Prior Publication Data
US 2016/0201069 A1 Jul. 14, 2016

Related U.S. Application Data

(60) Provisional application No. 61/868,529, filed on Aug. 21, 2013.

(51) Int. Cl.
*C12N 15/82* (2006.01)
(52) U.S. Cl.
CPC ..... *C12N 15/8205* (2013.01); *C12N 15/8218* (2013.01); *C12N 15/8251* (2013.01)
(58) Field of Classification Search
None
See application file for complete search history.

(56) References Cited

U.S. PATENT DOCUMENTS 7,176,352 B1 2/2007 Edelman et al.

FOREIGN PATENT DOCUMENTS

WO  WO 99/07210      2/1999
WO  WO 02/10414 A2   2/2002

OTHER PUBLICATIONS

Chhabra et al. (cited in IDS, Physiol. Mol. Biol. Plants (Apr.-Jun. 2011) 17(2): pp. 129-136).*
Ohira et al. (Plant and Cell Physiol. 14: pp. 1113-1121 (1973)).*
Tabei et al. (cited in IDS, Breeding Science, 44: pp. 47-51 (1994)).*
Yamamoto et al. (cited in IDS, in Vitro Cellular & Developmental Biology-Plant, (2001), vol. 37, No. 3, pp. 349-353).*
Hansen et al., Recent advances in the transformation of plants. Trends Plant Sci. Jun. 1999;4(6):226-231.
Mollá-Morales et al., Duckweeds: Genetic study for biofuel production. The Second International Conference on Duckweed Research and Applications. Aug. 21-24, 2013. p. 11. Abstract.
Mollá-Morales, Duckweed: Genetic study for biofuel production. The Second International Conference on Duckweed Research and Applications. Aug. 21-24, 2013. Presentation. 32 pages.
Moon et al., Effects of medium components and light on callus induction, growth, and frond regeneration in *Lemna gibba* (Duckweed). In Vitro Cell & Develop Biol—Plant. 1997; 33:20-25.
Pastor et al. Highly-specific gene silencing by artificial microRNAs in *Lemnaceae*. The Second International Conference on Duckweed Research and Applications. Aug. 21-24, 2013. p. 21. Abstract.
Pastor et al. Specific gene silencing by artificial microRNAs in *Lemnaceae*. The Second International Conference on Duckweed Research and Applications. Aug. 21-24, 2013. Poster Presentation.
Schenk et al., Medium and techniques for induction and growth of monocotyledonous and dicotyledonous plant cell cultures. Canadian J of Botany. 1972; 50(1):199-204.
Tabei et al., Selection of transformed callus in a liquid medium and regeneration of transgenic plants in cucumber (*Cucumis sativus* L.). Breeding Science. 1994; (44): 47-51.
Yan et al., Survey of the total fatty acid and triacylglycerol composition and content of 30 duckweed species and cloning of a Δ6-desaturase responsible for the production of γ-linolenic and stearidonic acids in *Lemna gibba*. BMC Plant Biol. Dec. 5, 2013;13:201. doi: 10.1186/1471-222913-201.
Canto-Pastor et al., Efficient transformation and artificial miRNA gene silencing in Lemna minor. Plant Biology. Epub Jul. 2, 2014. 7 pages.
Chhabra et al., Genetic transformation of Indian isolate of Lemna minor mediated by Agrobacterium tumefaciens and recovery of transgenic plants. Physiology and Molecular Biology of Plants. 2011;17(2):129-36.
Thiruvengadam et al., Establishment of an efficient Agrobacterium tumefaciens-mediated leaf disc transformation of spine gourd (Momordica dioica Roxb. ex Willd). African Journal of Biotechnology. 2011;10(83):19337-45.
Yamamoto et al., Genetic transformation of duckweed Lemna gibba and Lemna minor. In Vitro Cellular & Developmental Biology-Plant. 2001;37(3):349-53.

(Continued)

*Primary Examiner* — Brent Page
*Assistant Examiner* — Jared Shapiro
(74) *Attorney, Agent, or Firm* — Wolf, Greenfield & Sacks, P.C.

(57) ABSTRACT

The present disclosure provides methods and compositions for genetic transformation of *Lemnaceae* species.

18 Claims, 16 Drawing Sheets

(56) References Cited

OTHER PUBLICATIONS

Boehm et al., A transient transformation system for duckweed (Wolffia columbiana) using Agrobacterium-mediated gene transfer. Journal of Applied Botany. Aug. 2001;75(3-4):107-111.
Vunsh et al., High expression of transgene protein in Spirodela. Plant Cell Rep. Sep. 2007;26(9):1511-9. Epub May 10, 2007.

* cited by examiner

DWC131 MS 3% sucrose  DWC131 MS 3% sucrose without nitrate (N deprivation)

➡ Transformed region

➡ Dead tissue

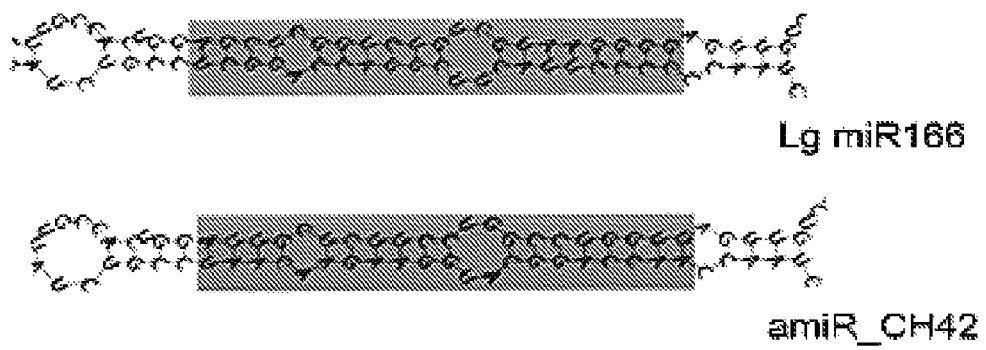
FIG. 16A
```
CH42-A mRNA   5'..AUUGGUCUGUACCUUCUUGUUAUUG..3'   SEQ ID NO: 55
                   ||||||o||||||||||||||
amiRNA        3'   AACCAGGCAUGGAAGAACAAU        5'   SEQ ID NO: 56
CH42-B mRNA   5'..AUUGGUCUCUACCUUCUUGUUAUUG..3'   SEQ ID NO: 57
                   ||||||o |||||||||||||
amiRNA        3'   AACCAGGCAUGGAAGAACAAU        5'   SEQ ID NO: 56
```
FIG. 16B
FIG. 16C

| SEQ ID NO: | | |
|---|---|---|
| 46 | RACE1 | gtgaaacatggcaaaactcataatgggaaagagacccaataa-tttcatcaaagccagcaaaccagtgttcggatccggaagggcgaattcgt |
| 47 | RACE2 | gtgaaacatggcaaaactcataatgggaaagagacccaataacttcatcaaagccagccagcaaaccagtgttcggatccggaagggcgaattcgt |
| 48 | CH42-A 3' | gtgaaacatggcaaaactcataatgggaaagagacccaataacttcatcaaagccagccagcaaaccagtgttcggatccggaagggcgaattcgt... taaattcttcaagattggcatcatcact...gct 5' |
| 49 | CH42-B 3' | gcgaaacatggcaaaactcataatgggaaagagacccaataacaagaagtagagaccaataacaagaagtagaga... taaattcttcaagattcttcaagattggcatcatcact...act 5' |
| 50 | RACE3 | gcgaaacatggcaaaactcataatgggaaagagacccaataacaagaagtagagaccaataacaagaagtagaga... taaattcttcaagattcttcaagattggcatcatcaact |

5' RACE adapter  TOPO/TA vector

FIG. 21

SEQUENCE LISTING

```
<160> NUMBER OF SEQ ID NOS: 65

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
cttctcatta tcggtggtga ac                                              22

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
```

-continued ctctctaacc atctgtgggt c                                    21

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
ctggagatta ttactcgggt agatc                                25

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 4
atgattagag tcccgcaatt atac                                 24

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 5
gcaaactagg ataaattatc gcgc                                 24

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 6
gttactagat cgaccggcat g                                    21

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
caatcgccag aaatgtcaga                                      20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
gcctccctct ctcttcctct                                      20

<210> SEQ ID NO 9
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 9
tttgagccag tttagggtgc                                                     20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
cgcgctttcc ctctttctct                                                     20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 11
gagagataag ccaaagacga g                                                   21

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 12
cgttgtggag aattgaagag c                                                   21

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
atgtaggggg atggaaggag                                                     20

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 14
tcgctctagg aaaccaaaac a                                                   21

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ccggtagagc gagagaagaa                                                     20
```

```
<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
gatcgtcggc gagaagaa                                                        18

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
tctacatgct aagagggtgg tg                                                   22

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
tcccattgag acgaagaagg                                                      20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
ggggaatgaa gcctggtccg a                                                    21

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gaacttgtgg ccgtttacgt                                                      20

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21
gctcctacaa atgccatca                                                       19

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide
```

<400> SEQUENCE: 22
agggagctcc cttcagtcca a                                         21

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
actagagcca agctgatctc                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
ttgtgatatc actagtgcgg                                           20

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
gacccggtcg tgcccctct                                            19

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gtaacaccaa acaacagggt                                           20

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27
tatttaatat atgtttgcga t                                         21

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tgtgcgcagt tctgcaaaga                                           20

<210> SEQ ID NO 29

```
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t

<400> SEQUENCE: 29
ntcgastwts gwgtt                                                    15

<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 30
ngtcgaswga nawgaa                                                   16

<210> SEQ ID NO 31
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 31
sttgntastn ctntgc                                                   16

<210> SEQ ID NO 32
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 32
gttttcccag tcacgac                                                  17

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 33
```

-continued

```
aacagctatg accatg                                                     16
```

<210> SEQ ID NO 34
<211> LENGTH: 2570
<212> TYPE: DNA
<213> ORGANISM: Artificial Sequence
<220> FEATURE:
<223> OTHER INFORMATION: Synthetic Polynucleotide

<400> SEQUENCE: 34

```
tatttaatat atgtttgcga ttttatttat ttgttttaat agaattattt gagtccttaa     60
ttatttaagt gggaagacgt tttttcttgt agtagaaaat tgaaatttgg ttttctagaa    120
atttgtattg tattggtgtt ccatttcact cggtgacagc tcgcttatgc tcacgcataa    180
gacataagct acgtggagat cgtgggttgt ttttccagc gaacttttc gctcgatcca     240
tggaaaatat caaaatatac aacatatttg caggaaattg catgatattt aatatatgtt    300
tgcgatttta tttatttgtt ttaatagaat tatttgagtc cttaattatt taagtgggaa    360
gacgttttt cttgtagtag aaaattgaaa tttggttttc tagaaatttg tattgtattg    420
gtgttccatt tcactcggtg acagctcgct tatgctcacg cataagacat aagctacgtg    480
gagatcgtgg gttgtttttt ccagcgaact ttttcgctcg atccatggaa aatatcaaaa    540
tatacaacat atttgcagga aattgcatga tatttaatat atgtttgcga ttttatttat    600
ttgttttaat agaattattt gagtccttaa ttatttaagt gggaagacgt tttttcttgt    660
agtagaaaat tgaaatttgg ttttctagaa atttgtattg tattggtgtt ccatttcact    720
cggtgacagc tcgcttatgc tcacgcataa gacataagct acgtggagat cgtgggttgt    780
ttttccagc gaacttttc gctcgatcca tggaaaatat caaaatatac aacatatttg     840
caggaaattg catgatcatc aacagtgtta aattcttttt cttctgttta caatttgttt    900
taaagtaaaa acaaaactat ttttatcatc cggaaacgag aaaataaaag atagtgaatt    960
tcttcggttt ttcaacttct tatataaata atttaaatat tcacgtgaga atggatgacc   1020
cggtccattg accgaccaat gggttgagtc agcaaagggg aaaaatatgg gcctcatatt   1080
tgacacggct ctctctctct ctctctctct ctctctctct ctctctctcc ctctctctct   1140
ctctctctct ctctctctct ctctctctct ctctctctca gtctcactcc ccatcatctc   1200
tcctctcaca aacaggtcta tctgtctatc tctctcctcc gccagccaca ggtctgaatg   1260
aattagcttt aaattttgag aagggagtga gtggttgtgt agccacctca tttgaccact   1320
accatgagac tttatgtaga ataaaattag ttttattttt taatataatt attccgtttc   1380
catttaggat ttagaataaa agtgggaggg gtttatttat tggagaatat tgtaatttgt   1440
tattttgga gtgaatggaa gtttcatttg tgtttcattt gtgttcatt tcgtgcggtg     1500
acagctcgct tatgctgacg catcctagct ttaaaggaa aggctgagcc agcggctgct    1560
ttgttggacg ccctcagacc gctgctcttc ttccacgcta cttttcttcc ggcggagaag   1620
aggtaaagct cgaccgcggc atcctcggaa tctcggagag caggtagaga tctatgctgg   1680
ttttctcata gatcggtctt ctcgaaacct gtaaatcttc tgattgctt gtctgatacc    1740
attttcttcc cgatcgtagc atttcgcatg ctgtttattc gtgttttttg ttttctcggc   1800
ttgcaatctt tgagatgttc agatcttatg tcttctcgtg tcgcatcttg tagatctggt   1860
ttcttttgt gcgccgatct gttcactcga tcctcttttc tcgtcaatcg ccagcgatct    1920
ttattaactt gttctccgag gaggattccc tgctttccat ggcgattatc aacatctcgg   1980
```

```
gtgcttgcgt gaagttcttt ttctgatttc ccgttgtaga acataagtta ccatttcttt    2040
cattatctgt attttctttt cgtatcagat gcatttcctc tactgtttct gctgctttct    2100
gtacttctcc gattggaggc tcgatttcct gatatttgga gacaactaca ggaagcatta    2160
cgtatttcca actgtagatt aacattcctt tttggttcat cgatctgtca tcctcatttt    2220
tcatcatttt tcgtggaaag tactaaaaga ttaactggtc taggtcctgg cgaataactg    2280
tgatggaaaa aatgacatta ctaatataat ttaacctaat ttcgttgaca cgatcattta    2340 tggttttta tttaaacaaa tactacgaga cttcggagtc tatattgtca ttttttata     2400 tgggaggtaa actggtcaat ttccagtttc ttttgtcatg tcttctatct aaatatgtaa    2460
catctatcgg aattattccc ctgaattatc atccctttct acttatctta atttcatttt    2520
ctgtcctctc tagctatctt aattaactca tctttgcaga actgcgcaca              2570

<210> SEQ ID NO 35
<211> LENGTH: 2050
<212> TYPE: DNA
<213> ORGANISM: Artificial Sequence
<220> FEATURE:
<223> OTHER INFORMATION: Synthetic Polynucleotide

<400> SEQUENCE: 35
caatcgccag aaatgtcaga agaggctggc tctagaggc cccgcaaggc ctcacccaga      60
gttggcgcag cctcgccgcg tccgaggcat gtgcagctca ctaaacggga aatttccaac    120
agtcaacccg cagacaaggg ccaaacccca aagaacaatt ctttgtccat gaagtaaaat    180
aacgttttat cttgaaacaa gagttcaagg ccaaatgtgg ccaagcgatt cggatggggg    240
ggcatgaaca ccttgcaatc atttcctgac tcatttctga acagtgccct ggcacacgt     300 gtagacctgc caacataatt aaaatataat attagaaaaa aatctccca tagtatttag     360 tatttaccaa aagtcacacg accactagac ttccaattta cccaaatcac taaccaattt    420
taggttgaat ggaaaataga acgcaataat gtccgacata tttcctatat ttccgttttt    480
cgagagaagg cctgtcgata aggatgtaat ccatggggcg acgcagtgtg tggaggagca    540
ggctcagtct ccttctcgtg agggatcgaa cgatggcagc cgtagaatgc tcagagcaat    600
gacccagcca gctgtgggga cctatttaag cgggttatga cgagtctcag actcgcaagt    660
ggagagagga tccgagcgtc cagtcatcgc cagaaatgtc aagaggctg cctctagag      720 gccccgcaag gcctcaccca gagttggcgc agcctcgccg cgtccgaggc atgtgcagct    780
cactaaacgg gaaatttcca acagtcaacc cgcagacaag ggccaaaccc caagaacaa     840 ttctttgtcc atgaagtaaa ataacgtttt atcttgaaac aagagttcaa ggccaaatgt    900
ggccaagcga ttcggatggg ggggcatgaa caccttgcaa tcatttcctg actcatttct    960
gaacagtgcc cttggcacac gtgtagacct gccaacataa ttaaaatata atattagaaa   1020
aaaaatctcc catagtattt agtatttacc aaaagtcaca cgaccactag acttccaatt   1080
tacccaaatc actaaccaat tttaggttga atggaaaata gaacgcaata atgtccgaca   1140
tatttcctat atttccgttt ttcgagagaa ggcctgtcga taaggatgta atccatgggg   1200
cgacgcagtg tgtggaggag caggctcagt ctccttctcg tgagggatcg aacgatggca   1260
gccgtagaat gctcagagca atgacccagc cagctgtggg gacctattta agcgggttat   1320
gacgagtctc agactcgcaa gtggagagag gatccgagcg tccagtcaat cgccagaaat   1380
gtcagaagag gctggcctct agaggccccg caaggcctca cccagagttg gcgcagcctc   1440
gccgcgtccg aggcatgtgc agctcactaa acgggaaatt tccaacagtc aacccgcaga   1500
```

```
caagggccaa accccaaaga acaattcttt gtccatgaag taaaataacg ttttatcttg    1560
aaacaagagt tcaaggccaa atgtggccaa gcgattcgga tgggggggca tgaacacctt    1620
gcaatcattt cctgactcat ttctgaacag tgcccttggc acacgtgtag acctgccaac    1680
ataattaaaa tataatatta gaaaaaaaat ctcccatagt atttagtatt taccaaaagt    1740
cacacgacca ctagacttcc aatttaccca aatcactaac caattttagg ttgaatggaa    1800
aatagaacgc aataatgtcc gacatatttc ctatatttcc gttttcgag agaaggcctg     1860 tcgataagga tgtaatccat ggggcgacgc agtgtgtgga ggagcaggct cagtctcctt    1920
ctcgtgaggg atcgaacgat ggcagccgta gaatgctcag agcaatgacc cagccagctg    1980
tggggaccta tttaagcggg ttatgacgag tctcagactc gcaagtggag agaggatccg    2040
agcgtccagt                                                           2050

<210> SEQ ID NO 36
<211> LENGTH: 663
<212> TYPE: DNA
<213> ORGANISM: Artificial Sequence
<220> FEATURE:
<223> OTHER INFORMATION: Synthetic Polynucleotide

<400> SEQUENCE: 36
ttagggtgca aataattac acatcctaag aattatttat ctacaattta gctccggaca      60
aaattagttc attattcaat cactttaatg ttttcaatgg ccacaaaatg ttttgatcca    120
gatgcacttt tgattcagtc accctagatg cacttttga tccccggcaa aactttagga    180
ctagtgtccg ttcactcacc ttctaataat ctgtgtgacg aaaatataaa gaaaaacagt    240
gacaattatc ctatttgaac aagacctgag ttgctcgttt tactcactag atatgccact    300
aaaaaggtga gaatagtttt cttactactt tggcatttgc cacctaattt cagtgtcaga    360
gtcgactagc cttccattcc ttgtaaatca atgaaaattt gatgaaaact aagaaccttc    420
aataagcgac aaatcgcttc gtttctcctt tgcggataga tggcagacga taagaatgta    480
atccagaaga tgaggccatt gtggaggaga agatgcagtg tccccctctg tagagatcga    540
acaatggcag ccatagaatc cccggagcac tgagacaggg acagacgcca atttaagtgg    600
cccgagaacg gttttagaaa ctcccgaggt gagcaaggat ccggatcgag cgcgaagaag    660
aga                                                                  663

<210> SEQ ID NO 37
<211> LENGTH: 138
<212> TYPE: DNA
<213> ORGANISM: Artificial Sequence
<220> FEATURE:
<223> OTHER INFORMATION: Synthetic Polynucleotide

<400> SEQUENCE: 37
ttactgttga ggggaatgct gtctggctcg aggtcaccgt tctcttcttc tcaatctcct     60
acttccatct atctgaatgg agaagggaat ggaaggagag atctgcctcg gaccaggctt    120
cattcccccc aatcaaag                                                  138

<210> SEQ ID NO 38
<211> LENGTH: 142
<212> TYPE: DNA
<213> ORGANISM: Artificial Sequence
<220> FEATURE:
<223> OTHER INFORMATION: Synthetic Polynucleotide
```

<400> SEQUENCE: 38

```
ccgttgggaa gcttttcctt tgagggggaat gttgtctggc tcgaggtttc tcctttctct    60
ctctggagaa attgcgatgg agaggagaga atgccctcgg accaggcttc attcccctca   120
atcgcagctt ccacaaacct tc                                            142
```

<210> SEQ ID NO 39
<211> LENGTH: 132
<212> TYPE: DNA
<213> ORGANISM: Artificial Sequence
<220> FEATURE:
<223> OTHER INFORMATION: Synthetic Polynucleotide

<400> SEQUENCE: 39

```
gtcgcatgtt gaggctggct tgtggggaat gttgtctggc ctgaggtcaa gcaatggaga    60
tattgtgggt ataaggtctc tagatctcgg accaggcttc attcccctca gccggcatcc   120
acattttctc tc                                                       132
```

<210> SEQ ID NO 40
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 40

```
gcttcgtcgg tgatatggga ggaagagagc ttccttctgt ccactctctg gtggccgcag    60
gactacgcca tctgccgact cattcatcca aatcccaagc cgcggaggat tttcaggttt   120
gggagatgcg tgaatggcgc gggagatagc ccgggttctg cgccggctgt gtttggactg   180
aagggagctc cctcttcttc atctctctct ctctaccg                           218
```

<210> SEQ ID NO 41
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 41

```
ggggacaagt ttgtacaaaa aagcaggctg cccgttggga agcttttcct ttgacagttc    60
attgctacat cttaaggttt ctcctttctc tctctggaga aattgcgatg gagaggagag   120
aatgccctta gaatgtaggt atgaactgtc aatcgcagct tccacaaacc ttctacccag   180
ctttcttgta caaagtggtc c                                             201
```

<210> SEQ ID NO 42
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 42

```
taacaagaag gtacagacca a                                              21
```

<210> SEQ ID NO 43
<211> LENGTH: 148
<212> TYPE: DNA
<213> ORGANISM: Artificial Sequence
<220> FEATURE:
<223> OTHER INFORMATION: Synthetic Polynucleotide
```

<400> SEQUENCE: 43

```
cttctcatta tcggtggtga acatggtatc gtcaccttct ccgtcgaact ttcttcctag      60
atcgtagaga tagagaaagt cgtccatggt gatctccggg gcaaaggaga tcagcttggc     120
tctagcagcc tgcttttttg aactatca                                        148
```

<210> SEQ ID NO 44
<211> LENGTH: 288
<212> TYPE: DNA
<213> ORGANISM: Artificial Sequence
<220> FEATURE:
<223> OTHER INFORMATION: Synthetic Polynucleotide

<400> SEQUENCE: 44

```
tcttcctaga tcgtagagat agagaaagtc gtccatggtg atctccgggg caaaggagat      60
cagcttggct ctagtagcct gcttttttgt acaaacttgt gatatcacta gagcttagct     120
tgagcttgga tcagattgtc gtttcccgcc ttcagtttaa actatctact aagaaagaga     180
gagatctgat cctcgtacct tcttcgacgc gaggtcaagg acaatctcat tgatcatgat     240
tctcaagagc tcatcctcca ggtcaatgcc ccattcaaac gcctcaac                  288
```

<210> SEQ ID NO 45
<211> LENGTH: 137
<212> TYPE: DNA
<213> ORGANISM: Artificial Sequence
<220> FEATURE:
<223> OTHER INFORMATION: Synthetic Polynucleotide

<400> SEQUENCE: 45

```
catctactaa taaagagaga gatctgatct catacccttc ttcgacgcga ggtcaaggac      60
aatctcattg atcatgattc tcaagagctc atcctccagg tcaatgcccc attcaaacgc     120
ctcaacatgg aagtcaa                                                    137
```

<210> SEQ ID NO 46
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 46

```
gtgaaacatg gcaaaactca taatgggaaa gagacccaat aatttcatca agccagcaa      60
acgcagtgtt cggatccgcg aagggcgaat tcgt                                 94
```

<210> SEQ ID NO 47
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 47

```
gtgaaacatg gcaaaactca taatgggaaa gagacccaat aactttcatc aaagccagca     60
aacgcagtgt tcggatccgc gaagggcgaa ttcgt                                95
```

<210> SEQ ID NO 48
<211> LENGTH: 95
<212> TYPE: DNA
<213> ORGANISM: Artificial Sequence
<220> FEATURE:

<223> OTHER INFORMATION: Synthetic Polynucleotide

<400> SEQUENCE: 48
gtgaaacatg gcaaaactca taatgggaaa gagacccaat aacaagaagg tacagaccaa    60
taaattcttc aagatttggc atcatcactt cagct    95

<210> SEQ ID NO 49
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 49
gcgaaacatg gcaaaactca taatgggaaa gagacccaat aacaagaagg tagagaccaa    60
taaattcttc aagatttggc atcatcactt caact    95

<210> SEQ ID NO 50
<211> LENGTH: 95
<212> TYPE: DNA
<213> ORGANISM: Artificial Sequence
<220> FEATURE:
<223> OTHER INFORMATION: Synthetic Polynucleotide

<400> SEQUENCE: 50
gcgaaacatg gcaaaactca taatgggaaa gagacccaat aacaagaagg tagagaccaa    60
taaattcttc aagatttggc atcatcactt caact    95

<210> SEQ ID NO 51
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 51
gagcucgguc uguuguaagg ggag    24

<210> SEQ ID NO 52
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 52
cuccccuuac uucggaccag gcuc    24

<210> SEQ ID NO 53
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 53
gaagucauau uaugugcuag ccag    24

<210> SEQ ID NO 54
<211> LENGTH: 24
<212> TYPE: RNA
<213> ORGANISM: Artificial Sequence
<220> FEATURE:
<223> OTHER INFORMATION: Synthetic Oligonucleotide

```
<400> SEQUENCE: 54
cuggcuagca guugauauaa cuuc                                              24

<210> SEQ ID NO 55
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 55 auugguccugu accuucuugu uauug                                            25

<210> SEQ ID NO 56
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 56
uaacaagaag guacggacca a                                                 21

<210> SEQ ID NO 57
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 57
auuggucucu accuucuugu uauug                                             25

<210> SEQ ID NO 58
<211> LENGTH: 37
<212> TYPE: RNA
<213> ORGANISM: Artificial Sequence
<220> FEATURE:
<223> OTHER INFORMATION: Synthetic Oligonucleotide

<400> SEQUENCE: 58
uguugagggg aaugcugucu ggcucgaggu caccguu                                37

<210> SEQ ID NO 59
<211> LENGTH: 34
<212> TYPE: RNA
<213> ORGANISM: Artificial Sequence
<220> FEATURE:
<223> OTHER INFORMATION: Synthetic Oligonucleotide

<400> SEQUENCE: 59
aucugccucg gaccaggcuu cauuccccc aauc                                    34

<210> SEQ ID NO 60
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 60
cuguugauug guccgguccu ucucguuagg ucaccguu                               38

<210> SEQ ID NO 61
```

```
<211> LENGTH: 34
<212> TYPE: RNA
<213> ORGANISM: Artificial Sequence
<220> FEATURE:
<223> OTHER INFORMATION: Synthetic Oligonucleotide

<400> SEQUENCE: 61
aucugccuaa caagaaggua cggaccaacc aauc                                      34

<210> SEQ ID NO 62
<211> LENGTH: 37
<212> TYPE: RNA
<213> ORGANISM: Artificial Sequence
<220> FEATURE:
<223> OTHER INFORMATION: Synthetic Polynucleotide

<400> SEQUENCE: 62
uguugagggg aaugcugucu ggcucgaggu caccguu                                   37

<210> SEQ ID NO 63
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 63
aucugccucg gaccaggcuu cauuccccc aauc                                       34

<210> SEQ ID NO 64
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 64
cuguugauug guccgguccu ucucguuagg ucaccguu                                  38

<210> SEQ ID NO 65
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 65
aucugccuaa caagaaggua cggaccaacc aauc                                      34
```

TRANSFORMATION OF DUCKWEED AND USES THEREOF

RELATED APPLICATIONS

This application is a national stage filing under 35 U.S.C. § 371 of international application number PCT/US2014/052182, filed Aug. 21, 2014, which was published under PCT Article 21(2) in English and claims the benefit under 35 U.S.C. § 119(e) of U.S. provisional application Ser. No. 61/868,529, filed Aug. 21, 2013, each of which is herein incorporated by reference in its entirety.

GOVERNMENT FUNDING

This invention was made with Government support under contract numbers DE-EE0003298 and DE-ACO2-98CH10886, awarded by the U.S. Department of Energy. The Government has certain rights in the invention.

BACKGROUND

Petroleum availability has become one of the main concerns of the current era. Petroleum consumption during the past decade has increased exponentially, while only few of new oilfields and other sources have been discovered. In fact, according to the annual estimations of the Central Intelligence Agency of the United States (CIA, 2013), it is predicted that with current resources, society will run out of petroleum in less than 50 years. This known scarcity has created the need to develop renewable energy resources.

SUMMARY

Lemnaceae species (e.g., Lemna gibba, Lemna minor and Spirodela polyrhiza), commonly known as duckweeds or water lentils, are the world's smallest aquatic flowering plants. Although they are true monocotyledonous angiosperms, they have a much reduced morphology comprising growing fronds, simple roots and two "pockets" of meristematic stem cells. Lemnaceae in optimal conditions have an exponential growth rate that can double the number of fronds in 30 hours and produce 64 grams of biomass per gram of starting weight in a week, which is far beyond the fastest growing corn rates (2.3 g/g/week) and is unencumbered by secondary products such as lignin. Lemnaceae plants are an attractive option as biofuel feedstocks because of their robust growth in marginal aquatic environments and excellent metabolic characteristics.

Methods of the present disclosure were used, as described herein, to modulate expression of several different categories of genes, including various enzymes (e.g., CH42, PDS, PDAT1 and DGAT1) and transcription factors (e.g., WRI1b). Methods of the present disclosure were also used to stably express in duckweed several different exogenous promoters (e.g., a ubiquitin promoter from maize and a 35S promoter from CaMV) and endogenous promoters (e.g., actin promoter from duckweed).

Thus, various aspects and embodiments of the disclosure provide methods for stably transforming duckweed with a nucleic acid, the methods comprising in the following ordered steps: (a) inoculating, in liquid infection medium that comprises magnesium, a plant metabolizable sugar, and acetosyringone, actively growing duckweed callus with an engineered Agrobacterium that comprises a nucleic acid of interest, a selectable marker gene, and visible reporter gene, thereby producing inoculated callus, (b) culturing inoculated callus on semi-solid nodule production medium that comprises acetosyringone, and then culturing inoculated callus on semi-solid selection medium that comprises a selection substance and antibiotic, thereby producing cultured, inoculated callus; (c) selecting, from cultured, inoculated callus of (b), transformed callus that expresses the visible reporter gene, (d) culturing, in liquid selection medium that comprises the selection substance and the antibiotic, selected callus of (c), and (e) culturing callus cultured in (d) on semi-solid medium, thereby producing genetically engineered progeny duckweed containing the nucleic acid of interest. In some embodiments, the semi-solid medium of (d) is semi solid selection medium that comprises the selection substance and the antibiotic.

In some embodiments, the Agrobacterium is an Agrobacterium tumefaciens. For example, in some embodiments, the Agrobacterium tumefaciens is Agrobacterium tumefaciens GV3101 (referred to in U.S. Provisional Application No. 61/868,527 as CV3101).

In some embodiments, the actively growing duckweed callus is actively growing Lemna minor callus. For example, in some embodiments, the actively growing Lemna minor callus is actively growing Lemna minor 8627 callus.

In some embodiments, the diameter of the actively growing duckweed callus of step (a) is 3 to 5 mm. In some embodiments, step (a) comprises contacting the duckweed callus with the Agrobacterium tumefaciens for 5 minutes.

In some embodiments, the liquid infection medium comprises magnesium sulfate, sucrose and acetosyringone. In other embodiments, the liquid infection medium consists of magnesium sulfate, sucrose and acetosyringone. For example, in some embodiments, the liquid infection medium consists of 10 mM magnesium sulfate, 10 g/L sucrose and 100 µM to 200 µM acetosyringone.

In some embodiments, the selection substance is DL-phosphinothricin.

In some embodiments, the visible reporter gene is green fluorescent protein.

In some embodiments, inoculated callus of step (b) is cultured for 2 to 4 days on the semi-solid nodule production medium. In some embodiments, the semi-solid nodule production medium of step (b) comprises acetosyringone, Murashige and Skoog basal salts, sucrose, 2,4-dichlorophenoxyacetic acid, and 6-benzylaminopurine. In other embodiments, the semi-solid nodule production medium of step (b) comprises or consists of 100 µM acetosyringone, 4.4 g/L Murashige and Skoog basal salts, 30 g/L sucrose, 1 µM 2,4-dichlorophenoxyacetic acid, and 2 µM 6-benzylaminopurine.

In some embodiments, the inoculated callus of step (b) is cultured for 4 to 7 days on the semi-solid selection medium. In some embodiments, the semi-solid selection medium of step (b) comprises the selection substance, the antibiotic, basal salts and sucrose. In some embodiments, the semi-solid selection medium of step (b) comprises DL-phosphinothricin, basal salts, sucrose, carbenicillin and cefotaxamin. In other embodiments, the semi-solid selection medium of step (b) consists of 10 mg/L DL-phosphinothricin, 3.2 g/L Shenk and Hilderbrandt (SH) basal salts, 10 g/L sucrose, 200 mg/L carbenicillin and 500 mg/L cefotaxamin.

In some embodiments, step (c) comprises selecting fluorescent cells using fluorescent microscopy.

In some embodiments, selected callus of step (c) is cultured in liquid selection medium for about 3 to 4 weeks. In some embodiments, the liquid selection medium of step (d) comprises the selection substance, the antibiotic, basal salts and sucrose. In some embodiments, the liquid selection medium of step (d) comprises DL-phosphinothricin, basal salts, sucrose, carbenicillin and cefotaxamin. In other embodiments, the liquid selection medium of step (d) comprises or consists of 10 mg/L DL-phosphinothricin, 3.2 g/L Shenk and Hilderbrandt (SH) basal salts, 10 g/L sucrose, 200 mg/L carbenicillin and 500 mg/L cefotaxamin.

In some embodiments, step (e) comprises culturing callus cultured in (d) on the semi-solid selection medium until genetically engineered progeny duckweeds are visible. In some embodiments, the semi-solid selection medium of step (e) comprises the selection substance, the antibiotic, basal salts and sucrose. In some embodiments, the semi-solid selection medium of step (e) comprises DL-phosphinothricin, basal salts, sucrose, carbenicillin and cefotaxamin. In other embodiments, the semi-solid selection medium of step (e) comprises or consists of 10 mg/L DL-phosphinothricin, 3.2 g/L Shenk and Hilderbrandt (SH) basal salts, 10 g/L sucrose, 200 mg/L carbenicillin and 500 mg/L cefotaxamin.

In some embodiments, the nucleic acid of interest comprises a promoter operably linked to a nucleic acid that encodes a protein of interest. In other embodiments, the nucleic acid of interest comprises a promoter operably linked to a nucleic acid that encodes an artificial microRNA.

Various other aspects and embodiments of the disclosure provide methods for transiently transforming duckweed with a nucleic acid, the methods comprising in the following ordered steps: (a) introducing an incision into the meristem tissue of duckweed, (b) infiltrating the incision with (i) infection medium that comprises magnesium, a plant metabolizable sugar and acetosyringone and (ii) engineered *Agrobacterium tumefaciens*, wherein the engineered *Agrobacterium tumefaciens* comprises a nucleic acid of interest, a selectable marker gene, and a visible reporter gene, thereby producing infiltrated duckweed, (c) culturing the infiltrated duckweed in liquid selection medium that comprises the selection substance and antibiotic, thereby producing cultured, infiltrated duckweed; and (d) identifying the cultured, infiltrated duckweed of (c) that expresses the visible reporter gene.

In some embodiments, the *Agrobacterium tumefaciens* is an *Agrobacterium tumefaciens* GV3101.

In some embodiments, the duckweed is *Spirodela polyrhiza*. For example, in some embodiments, the *Spirodela polyrhiza* is *Spirodela polyrhiza* 6581.

In some embodiments, the infection medium comprises or consists of magnesium sulfate, sucrose and acetosyringone. In some embodiments, the infection medium comprises or consists of 10 mM magnesium sulfate, 10 g/L sucrose and 100 μM acetosyringone.

In some embodiments, the selection substance is DL-phosphinothricin.

In some embodiments, the visible reporter gene is green fluorescent protein.

In some embodiments, the liquid selection medium of step (c) comprises the selection substance, the antibiotic, basal salts and sucrose. In some embodiments, the liquid selection medium of step (c) comprises DL-phosphinothricin, basal salts, sucrose, carbenicillin and cefotaxamin. In other embodiments, the liquid selection medium of step (c) consists of 10 mg/L DL-phosphinothricin, 3.2 g/L Shenk and Hilderbrandt (SH) basal salts, 10 g/L sucrose, 200 mg/L carbenicillin and 500 mg/L cefotaxamin.

In some embodiments, step (c) comprises culturing infiltrated duckweed on liquid selection medium for 2 to 4 days.

In some embodiments, step (d) comprises identifying cultured, infiltrated duckweed of step (c) that expresses the visible reporter gene using fluorescent microscopy.

In some embodiments, the nucleic acid of interest comprises a promoter operably linked to a nucleic acid that encodes a protein of interest. In other embodiments, the nucleic acid of interest comprises a promoter operably linked to a nucleic acid that encodes an artificial microRNA.

BRIEF DESCRIPTION OF THE DRAWINGS

FIG. 2A shows starch accumulation (arrow) under control conditions. FIG. 2B shows starch accumulation diverted into lipid bodies (arrows) under nitrogen deprivation.

FIG. 16A shows a comparison between secondary structures of the endogenous and the modified precursor. The sequences, from top to bottom, correspond to SEQ ID NOs: 62-65. FIG. 16B shows a predicted binding site of amiRNA to the CH42 mRNA. Circle indicates G:U wobble pairing. FIG. 16C shows a schematic diagram of the construct designed to express the amiRNA precursor. The construct contains a selectable marker that confers resistance to DL-phosphinothricin (PPT) as well as an independent GFP expression cassette to track regeneration of the callus. Transcription of the amiRNA precursor is driven by the CaMV 35S promoter.

FIG. 21 shows 5'-RACE (remote analysis computation for gene expression) analysis of the amiR-guided mRNA cleavage. Alignment of the two CH42 sequences present in L. minor genome with the sequences obtained from the cloning of 3 different bands. Ten out of 10 clones from each band present the sequence depicted here. Sequences corresponding to the amiRCH42 target (shaded TAACAAGAAGGTA-CAGACCAA (SEQ ID NO: 42)) and the stop codon (shaded TCA) are highlighted. Stars indicate polymorphisms between the two different gene copies.

FIG. 22A shows GFP expression under the control of the prolD promoter, indicative of Wrinkled 1 (WRI1b) expression under the control of the 35S promoter in a duckweed frond. A schematic of an expression construct is also shown. FIG. 22B shows GFP expression of under the control of the 35S promoter, as a control. FIG. 22C shows GFP expression under the control of the prolD promoter, indicative of LgPDAT1 expression under the control of the 35S promoter.

DETAILED DESCRIPTION

Lemnaceae are a widespread family of small aquatic plants. Efforts to genetically engineer Lemnaceae (e.g., duckweed) plants have been impeded by limits to facile stable transformation of mature plants and difficulties associated with regeneration (e.g., active growth) from calluses. The present disclosure provides, inter alia, highly efficient and cost-effective methods of stable genetic transformation of Lemnaceae species. The disclosure is based, in part, on the discovery that the duckweed transformation efficiency is greatly increased by introducing into actively growing duckweed callus a visible reporter gene, which is then used to aid in the "pre-selection" of transformed duckweed callus in vitro on cell culture plates prior to culturing transformed duckweed in liquid selection medium. This two-part selection step of the disclosure increases the genetic transformation efficiency 10-fold in comparison to existing duckweed transformation protocols. Additionally, in some embodiments, the transformation methods provided herein shorten the whole duckweed transformation and regeneration/growth process to about 4 to 5 weeks, in comparison to the 12 to 16 weeks typical of existing stable duckweed transformation protocols.

Lemnaceae include 37 species of free-floating monocots divided into five different genera: Spirodela, Landoltia, Lemna, Wolffia and Wolffiella (Les et al., 2002). With few exceptions, duckweeds include floating photosynthetic organs forming a single leaf-like structure known as frond. Compared to larger monocots, they present a highly modified structural organization as a result of alteration and simplification of morphological and anatomical features. These masses of tissue lack complex supportive and vascular structures, and while they exhibit roots, the functions of these are merely to stabilize the plant on the surface of water (Landolt, 1986). The body of duckweeds resembles a floating disc, or in the more reduced species, a cylinder or sphere. They often have one to several layers of prominent air spaces (aerenchyma) and one to several veins (nerves). Nutrients are assimilated directly through the ventral part of the frond.

Figure 1:
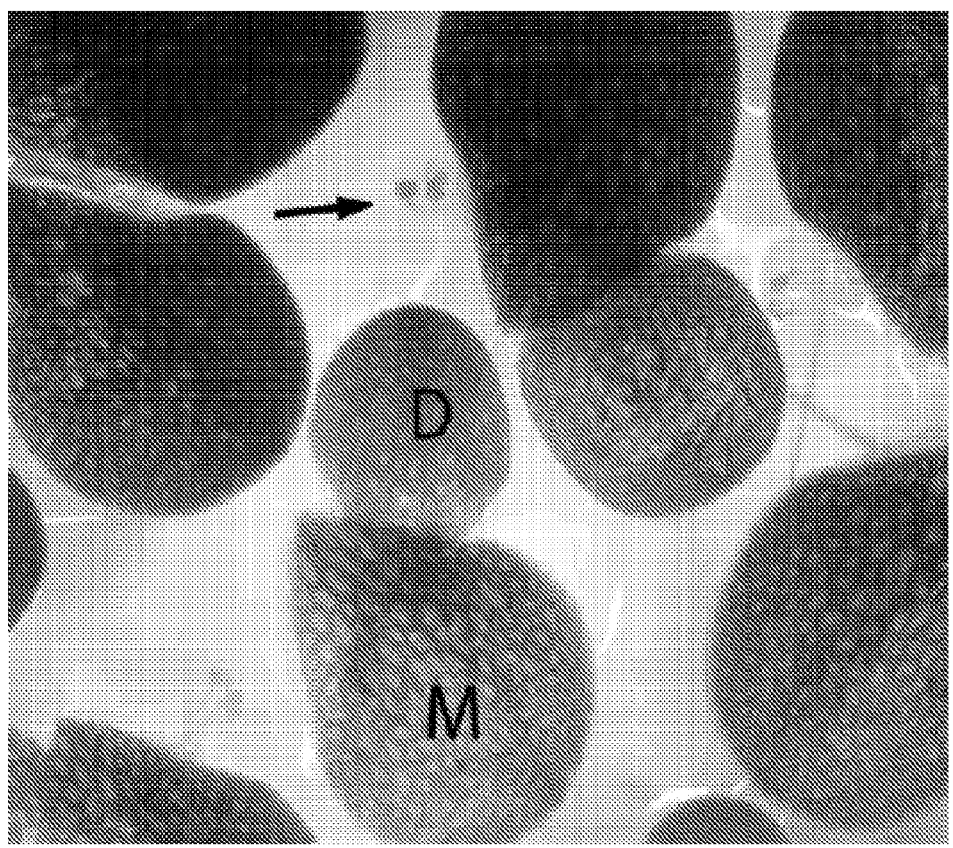
FIG. 1 shows an image of a flowering of *Lemna gibba* (*L. gibba*). Each mother frond (M) has produced a daughter frond (D) from one of the pockets, and some have produced a flower (arrow) from the other.

In terms of reproduction, duckweeds propagate nearly exclusively by asexual division forming dense homogenous clonal populations that cover the surface of quiet freshwater reservoirs. This mode of growth includes vegetative budding of genetically identical daughter fronds from a recessed meristem (also called pocket) situated at the basal end or along the two lateral margins of a parent plant (FIG. 1). These daughter plants often remain attached to the parent plant by a short stipe and after a time they detach, becoming independent fronds with same form and structure as the mother and the ability to produce their own daughter fronds (Landolt and Kandeler, 1987). This strategy is reflected in an interesting characteristic of this species: its growth rate. Under optimal conditions, *Lemnaceae* have an exponential growth rate that can double the number of fronds in 30 hours and produce up to 64 grams of biomass per gram of starting weight in one week. This growth rate surpasses by far any terrestrial crop, including corn (2.3 grams/grams/week). Another interesting characteristic is that the content of secondary products, such as lignin, remains relatively low as compared to land monocots species.

"Duckweed," as used herein, refers to members of the family *Lemnaceae*. There are four known genera and 37 species of duckweed, including the following: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wolfiella* (*Wl. caudata, Wl. denticulata, Wl. gladiata, Wl. hyalina, Wl. lingulata, Wl. repunda, Wl. rotunda*, and *Wl. neotropica*). Other genera or species of *Lemnaceae* are also contemplated herein. In some embodiments, the *Lemnaceae* plant is a *Lemna gibba* (*L. gibba*) plant, while in other embodiments, the *Lemnaceae* plant is a *Lemna minor* (*L. minor*) plant. In some embodiments, the *Lemnaceae* plant is a *Spirodela polyrhiza* (*S. polyrhiza*) plant.

Stable Transformation

In some aspects, provided herein are methods for stably transforming duckweeds (e.g., *Lemna minor*) with a nuclei acid. "Stable transformation," as used herein, refers to the insertion of an engineered (e.g., recombinant or synthetic) nucleic acid into a chromosome of a cell, which will be passed during mitosis to all subsequent daughter cells. Methods for stably transforming duckweeds (e.g., callus cells and/or meristematic stem cells of duckweeds) with a nucleic acid in accordance with the disclosure may comprise inoculating, in liquid infection medium that comprises magnesium (e.g., magnesium sulfate), a plant metabolizable sugar (e.g., sucrose), and acetosyringone, an actively growing duckweed callus with engineered bacteria (e.g., engineered *Agrobacterium* such as *Agrobacterium tumefaciens*) that comprise a nucleic acid of interest, a selectable marker gene, and a visible reporter gene, thereby producing inoculated callus.

The term "engineered bacteria," or "engineered *Agrobacterium*," as used herein, refers to bacteria (e.g., competent bacteria) that contain an engineered (e.g., recombinant or synthetic) nucleic acid. Any suitable method of bacterial transformation may be used to transform the bacterial cells in accordance with the disclosure.

A "callus," as used herein, is a mass of unorganized parenchyma cells derived from duckweed. Generally, callus formation is induced from duckweed tissues after surface sterilization and plating onto in vitro tissue culture medium (e.g., medium comprising basal salts and growth nutrients). Methods of callus induction that may be used in accordance with the disclosure are described by Yamamoto et al. (2001) and Moon and Stomp (1997), each of which is incorporated by reference herein in its entirety. In one embodiment of the disclosure, actively growing duckweeds (e.g., duckweed fronds) from approximately 1-week-old to 3-week-old (e.g., 2-week-old) cultures are placed on callus induction medium plates (e.g., containing basal salts, sucrose, 2,4-dichlorophenoxyacetic acid (2,4-D) and thidiazuron) with the adaxial part of the frond in contact with the medium. Approximately three to four weeks after being placed on the callus induction medium plates, light green masses of unorganized cells are selected and transferred to plates containing nodule production medium (NPM) (e.g., containing Murashige and Skoog (MS) basal salts, sucrose, 2,4-D and 6-Benzylaminopurine (BAP)). Tissue obtained from the NPM plates after about one week are used for transformation or are transferred to fresh media.

In some embodiments, the actively growing duckweed calluses are a *Lemna* species. For example, in some embodiments, the actively growing duckweed calluses are actively growing *Lemna gibba* callus, while in other embodiments, the actively growing duckweed calluses are actively growing *Lemna minor* callus. In some embodiments, the actively growing *Lemna minor* calluses are actively growing *Lemna minor* 8627 callus. Other actively growing duckweed calluses may be used as provided herein.

In some embodiments, the actively growing duckweed callus is about 1 mm to about 5 mm in diameter. For example, in some embodiments, the callus is 1 mm, 2 mm, 3 mm, 4 mm or 5 mm in diameter. In some embodiments, the callus is 3 mm.

The term "inoculating," as used herein, refers to the introduction of bacteria (e.g., engineered bacteria) into a plant (e.g., duckweed frond callus) or culture (e.g., liquid or semi-solid culture). In some embodiments, actively growing duckweed calluses (e.g., having a diameter of 3 mm) are inoculated with engineered bacteria (e.g., engineered *A. tumefaciens*) by contacting the actively growing duckweed calluses with infection medium containing the engineered bacteria. In some embodiments, the actively growing duckweed calluses are submerged, or partially submerged, in the infection medium.

In some embodiments, the actively growing duckweed calluses are contacted with (e.g., submerged in, or partially submerged in) infection medium containing engineered bacteria (e.g., engineered *A. tumefaciens*) for about 3 minutes to about 15 minutes, or about 5 minutes to about 10 minutes. For example, in some embodiments, the actively growing duckweed calluses are contacted with infection medium containing engineered bacteria (e.g., engineered *A. tumefaciens*) for 3, 4, 5, 6, 7, 8, 9, 10, 11, 12, 13, 14 or 15 minutes. In some embodiments, the actively growing duckweed calluses are contacted with infection medium containing engineered bacteria (e.g., engineered *A. tumefaciens*) for 5 minutes about 5 minutes.

"Infection medium" refers to culture medium that comprises magnesium, a plant metabolizable sugar, and acetosyringone.

Examples of magnesium that may be used in the infection medium include, without limitation, magnesium sulfate and magnesium chloride. Other forms of magnesium are contemplated herein including, without limitation, magnesium oxide, magnesium citrate, magnesium orotate, magnesium lactate, magnesium carbonate and magnesium glycinate.

Examples of plant metabolizable sugars that may be used in the infection medium include, without limitation, sucrose, turanose, palatinose and fluoro-Suc. Other metabolizable sugars are contemplated herein.

In some embodiments, the infection medium comprises magnesium sulfate ($MgSO_4$), sucrose and acetosyringone. In some embodiments, the infection medium consists of magnesium sulfate ($MgSO_4$), sucrose and acetosyringone.

In some embodiments, the infection medium comprises or consists of (1) magnesium sulfate, magnesium chloride, magnesium oxide, magnesium citrate, magnesium orotate, magnesium lactate, magnesium carbonate or magnesium glycinate, (2) sucrose, turanose, palatinose or fluoro-Suc, and (3) acetosyringone.

In some embodiments, the infection medium comprises or consists of (1) a combination of two or more of magnesium sulfate, magnesium chloride, magnesium oxide, magnesium citrate, magnesium orotate, magnesium lactate, magnesium carbonate or magnesium glycinate, (2) a combination of two or more of sucrose, turanose, palatinose or fluoro-Suc, and (3) acetosyringone.

In some embodiments, the infection medium comprises about 5 mM to about 15 mM magnesium (e.g., $MgSO_4$). For example, in some embodiments, the infection medium comprises 5 mM, 6 mM, 7 mM, 8 mM, 9 mM, 10 mM, 11 mM, 12 mM, 13 mM, 14 mM or 15 mM magnesium (e.g., $MgSO_4$). In some embodiments, the infection medium comprises 10 mM or about 10 mM magnesium (e.g., $MgSO_4$).

In some embodiments, the infection medium comprises about 5 g/L to about 10 g/L plant metabolizable sugar (e.g., sucrose). For example, in some embodiments, the infection medium comprises 5 g/L, 6 g/L, 7 g/L, 8 g/L, 9 g/L, 10 g/L, 11 g/L, 12 g/L, 13 g/L, 14 g/L or 15 g/L plant metabolizable sugar (e.g., sucrose). In some embodiments, the infection medium comprises 10 g/L or about 10 g/L plant metabolizable sugar (e.g., sucrose).

In some embodiments, the infection medium comprises about 50 μM to about 300 μM, or about 100 μM to about 200 μM acetosyringone. For example, in some embodiments, the infection medium comprises 50 μM, 75 μM, 100 μM, 125 μM, 150 μM, 175 μM, 200 μM, 225 μM, 250 μM, 275 μM or 300 μM acetosyringone. In some embodiments, the infection medium comprises 100 μM acetosyringone. In some embodiments, the infection medium comprises 200 μM acetosyringone.

In some embodiments, the infection medium comprises or consists of 10 mM magnesium (e.g., $MgSO_4$), 10 g/L plant metabolizable sugar (e.g., sucrose) and 100 μM or 200 μM acetosyringone.

Acetosyringone ($C_{10}H_{12}O_4$) is a phenolic natural product, and is a chemical compound related to acetophenone and 2,6-dimethoxyphenol. Acetosyringone is involved in plant-pathogen recognition, in particular, in transforming bacteria such as *Agrobacterium*. The virA gene on the Ti plasmid of *Agrobacterium tumefaciens* and the Ri plasmid of *Agrobacterium rhizogenes* is used by these soil bacteria to infect plants via its encoding for a receptor for acetosyringone and other phenolic phytochemicals exuded by plant wounds.

After the actively growing duckweed calluses are inoculated with engineered bacteria (e.g., engineered *Agrobacterium* such as *A. tumefaciens*), duckweed calluses are cultured on semi-solid nodule production medium (NPM) that comprises acetosyringone. "Nodule production medium" refers to culture medium that comprises acetosyringone, Murashige and Skoog basal salts, plant metabolizable sugar (e.g., sucrose), 2,4-dichlorophenoxyacetic acid, and 6-benzylaminopurine (BAP). In some embodiments, the nodule production medium may be modified. For example, in some embodiments, NPM may include, instead of or in addition to Murashige and Skoog basal salts, other salts and/or macronutrients (e.g., nitrate and/or organic additives such as agar, sugars, vitamins and growth regulators such as IAA (auxin/morphogen) and the Kinetin (cytokinin/cell division promoter)) typically used for plant cell culture (referred to herein as Murashige and Skoog basal salt equivalents). In some embodiments, modified NPM may include an herbicide other than 2,4-dichlorophenoxyacetic acid. In some embodiments, modified NPM may include a plant growth hormone other than 6-benzylaminopurine.

In some embodiments, the NPM, or modified NPM, comprises about 50 μM to about 300 μM, or about 100 μM to about 200 μM acetosyringone or other related compound. For example, in some embodiments, the NPM, or modified NPM, comprises 50 μM, 75 μM, 100 μM, 125 μM, 150 μM, 175 μM, 200 μM, 225 μM, 250 μM, 275 μM or 300 μM acetosyringone or other related compound. In some embodiments, the NPM, or modified NPM, comprises 100 μM acetosyringone. In some embodiments, the NPM comprises 200 μM acetosyringone or other related compound.

Murashige and Skoog medium is a widely used plant tissue culture growth medium. Murashige and Skoog Basal Medium contains macronutrients that include high levels of nitrate and organic additives such as agar, sugars, vitamins and growth regulators. Growth regulators frequently added to M&S include IAA (auxin/morphogen) and the Kinetin (cytokinin/cell division promoter). In some embodiments, the NPM, or modified NPM, comprises about 2 g/L to about 6 g/L Murashige and Skoog basal salts or an equivalent thereof. For example in some embodiments, the NPM, or modified NPM, comprises 2 g/L, 2.5 g/L, 3 g/L, 3.5 g/L, 4 g/L, 4.5 g/L, 5 g/L, 5.5 g/L or 6 g/L Murashige and Skoog basal salts or an equivalent thereof. In some embodiments, the NPM, or modified NPM, comprises 4.4 g/L Murashige and Skoog basal salts or an equivalent thereof.

In some embodiments, the NPM, or modified NPM, comprises about 20 g/L to about 40 g/L plant metabolizable sugar (e.g., sucrose). For example, in some embodiments, the NPM, or modified NPM, comprises 20 g/L, 25 g/L, 30 g/L, 35 g/L or 40 g/L plant metabolizable sugar (e.g., sucrose). In some embodiments, the NPM, or modified NPM, comprises of 30 g/L plant metabolizable sugar (e.g., sucrose).

In some embodiments, the NPM, or modified NPM, comprises about 0.5 μM to about 3 μM 2,4-dichlorophenoxyacetic acid (2,4-D) or other herbicide. For example, in some embodiments, the NPM, or modified NPM, comprises 0.5 μM, 1 μM, 1.5 μM, 2 μM, 2.5 μM or 3 μM 2,4-D. In some embodiments, the NPM comprises 1 μM 2,4-D or other herbicide.

6-Benzylaminopurine, benzyl adenine or BAP is a first-generation synthetic cytokinin that elicits plant growth and development responses, setting blossoms and stimulating fruit richness by stimulating cell division. In some embodiments, the NPM, or modified NPM, comprises about 1 μM to about 4 μM 6-benzylaminopurine (BAP) or other plant growth hormone. For example, in some embodiments, the NPM, or modified NPM, comprises 1 μM, 1.5 μM, 2 μM, 2.5 μM, 3 μM, 3.5 μM or 4 μM BAP or other plant growth hormone. In some embodiments, the NPM, or modified NPM, comprises or consists of 2 μM BAP or other plant growth hormone.

In some embodiments, the NPM comprises or consists of 100 μM or 200 μM acetosyringone, 4.4 g/L Murashige and Skoog basal salts, 30 g/L sucrose, 1 μM 2,4-D and 2 μM BAP.

In some embodiments, the actively growing duckweed calluses are cultured on semi-solid NPM (e.g., plates of NPM) for about 1 to 5 days, or more. For example, in some embodiments, the inoculated actively growing duckweed callus is cultured on semi-solid NPM for 1 day, 2 days, 3 days, 4 days or 5 days. In some embodiments, the actively growing duckweed calluses are cultured on semi-solid NPM for 2 days.

After the actively growing duckweed calluses are cultured on semi-solid NPM, they are subjected to a two-part selection step. In the first "pre-selection" part, the calluses are transferred to semi-solid selection medium, where transformed calluses (or callus cells) that express the visible reporter gene are selected (e.g., using fluorescent microscopy). In the second part of the selection step, following "pre-selection," transformed calluses that express the visible reporter gene are cultivated and subjected to further selection conditions.

"Selection medium" refers to culture medium that comprises a selection substance, antibiotic, basal salts and plant metabolizable sugar (e.g., sucrose). The selection medium may be semi-solid (e.g., an in vitro culture plate) or liquid.

A "selectable marker gene," as used herein, refers to a gene that confers resistance to a "selection substance" and is used to identify transformed duckweed calluses among untransformed calluses. The selection substance may be an herbicide or an antibiotic. In some embodiments, the selection substance is DL-phosphinothricin (PPT). Thus, in some embodiments, an actively growing duckweed callus is transformed with a gene that confers resistance to PPT (e.g., phosphinothricin acetyltransferase). Examples of other selection substances for use in accordance with the disclosure include, without limitation, kanamycin, hygromycin, gentamicin, bleomycin, phleomycin, methotrexate, streptomycin and spectinomycin (Ziemienowicz, A. *Acta Physiologiae Plantarum*, 2001, 23(3):363-374, incorporated by reference herein in its entirety). Other selection substance may be used as provided herein.

In some embodiments, the selection medium (e.g., semi-solid and/or liquid) comprises a selection substance in an amount sufficient to prevent the growth of non-transformed duckweeds/calluses. In some embodiments, the selection medium (e.g., semi-solid or liquid selection medium) comprises about 5 g/L to about 15 g/L PPT. For example, in embodiments, the selection medium (e.g., semi-solid or liquid selection medium) comprises about 5 g/L, 6 g/L, 7 g/L, 8 g/L, 9 g/L, 10 g/L, 11 g/L, 12 g/L, 13 g/L, 14 g/L or 15 g/L PPT or other selection susbtance. In some embodiments, the selection medium (e.g., semi-solid or liquid selection medium) comprises 10 g/L PPT or other selection substance.

In some embodiments, the selection medium (e.g., semi-solid and/or liquid) comprises one or more antibiotic(s) (e.g., carbenicillin and/or cefotaxamin). In some embodiments, the selection medium comprises about 100 mg/L to about 1000 mg/L of one or more antibiotic(s). In some embodiments, the selection medium comprises 100 mg/L, 150 mg/L, 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L or 1000 mg/L of one or more antibiotic(s). In some embodiments, the selection medium comprises about 100 mg/L to about 300 mg/L carbenicillin. For example, in some embodiments, the selection medium comprises 100 mg/L, 150 mg/L, 200 mg/L, 250 mg/L or 300 mg/L carbenicillin. In some embodiments, the selection medium comprises 200 mg/L carbenicillin. In some embodiments, the selection medium comprises about 400 mg/L to about 600 mg/L cefotaxamin. In some embodiments, the selection medium comprises 400 mg/L, 450 mg/L, 500 mg/L, 550 mg/L or 600 mg/L cefotaxamin. In some embodiments, the selection medium comprises 500 mg/L cefotaxamin. Other antibiotics may be used as provided herein.

In some embodiments, the selection medium (e.g., semi-solid and/or liquid) comprises basal salts (e.g., Shenk and Hilderbrandt (SH) basal salts) or other salt mixture typically used in plant cell culture and micropropagation. In some embodiments, the selection medium comprises about 2 g/L to about 5 g/L basal salts or other salt mixture. For example, in some embodiments, the selection medium comprises 2 g/L, 2.5 g/L, 3 g/L, 3.5 g/L, 4 g/L, 4.5 g/L or 5 g/L SH salts or other salt mixture. In some embodiments, the selection medium comprises 3.2 g/L salts or other salt mixture.

In some embodiments, the selection medium (e.g., semi-solid and/or liquid) comprises about 5 g/L to about 15 g/L plant metabolizable sugar (e.g., sucrose). For example, in embodiments, the selection medium comprises about 5 g/L, 6 g/L, 7 g/L, 8 g/L, 9 g/L, 10 g/L, 11 g/L, 12 g/L, 13 g/L, 14 g/L or 15 g/L plant metabolizable sugar (e.g., sucrose). In some embodiments, the selection medium comprises 10 g/L plant metabolizable sugar (e.g., sucrose).

In some embodiments, the selection medium comprises DL-phosphinothricin, carbenicillin, cefotaxamin, Shenk and Hilderbrandt (SH) basal salts and sucrose. In some embodiments, the selection medium consists of DL-phosphinothricin, carbenicillin, cefotaxamin, Shenk and Hilderbrandt (SH) basal salts and sucrose. In some embodiments, the selection medium (e.g., semi-solid and/or liquid) comprises or consists of 10 mg/L DL-phosphinothricin, 200 mg/L carbenicillin, 500 mg/L cefotaxamin, 3.2 g/L SH basal salts and 10 g/L sucrose.

In some embodiments, the actively growing duckweed calluses are cultured on semi-solid selection medium (e.g., plates of selection medium) for about 1 to 5 days, or more. For example, in some embodiments, the inoculated actively growing duckweed calluses re cultured on semi-solid selection medium for 1 day, 2 days, 3 days, 4 days or 5 days. In some embodiments, the inoculated actively growing duckweed calluses are cultured on semi-solid selection medium for 2 days.

As described above, after the actively growing duckweed calluses are cultured on semi-solid selection medium, the calluses, which include transformed and non-transformed masses of unorganized cells, are then subjected to a "pre-selection" step where callus cells expressing the visible reporter gene are selected. Thus, transformed calluses (or callus cells) are selected based on the presence of a visibly detectable signal. The visible reporter gene may be a gene that encodes a visible marker protein that can be visualized without killing the callus. Examples of visible reporters include, without limitation, fluorescent proteins and variants thereof (see, e.g., Patterson, G. H., et al. *Biophys. J.*, 1997, 73, 2782-2790, incorporated by reference herein in its entirety). Particular examples of fluorescent proteins for used herein include, without limitation, TagBFP, mTagBFP2, Azurite, EBFP2, mKalamal, Sirius, Sapphire, T-Sapphire, eCFP, Cerulean, SCFP3A, mTurquoise, mTurquoise2, monomeric Midoriishi-Cyan, TagCFP, mTFP1, eGFP, Emerald, Superfolder GFP, Monomeric Azami Green, TagGFP2, mUKG, mWasabi, Clover, mNeonGreen, eYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, NirFP, TagRFP657, IFP1.4, iRFP, mKeima Red, LSS-mKate1, LSS-mKate2, mBeRFP, PA-GFP, PAmCherry1, PATagRFP, Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange, and Dronpa. In some embodiments, the fluorescent protein is green fluorescent protein (GFP) or enhanced green fluorescent protein (eGFP).

In one embodiment, a plate of semi-solid selection medium containing transformed and non-transformed calluses are placed under a fluorescent microscope, and the calluses that are positive for the visible reporter gene (e.g., express the fluorescent protein) are selected for transfer to liquid selection medium. In some embodiments, at least a third of the calluses (or callus cells) are transformed and selected for transfer to liquid selection medium. In some embodiments, at least 25%, at least 30%, at least 35%, at least 40%, at least 45%, at least 50% or more of the calluses (or callus cells) are transformed and selected for transfer to liquid selection medium.

In this second part of the selection step, which permits simultaneous selection and regeneration/growth, the liquid selection medium contains calluses enriched with transformed cells. The liquid selection medium, in comparison to the semi-solid medium, permits the selection substance (e.g., PPT) and antibiotic (e.g., carbenicillin and cefotaxamin) to contact the entire surface of the calluses, which results in a more reliable selection process, in comparison to semi-solid selection only. In some embodiments, the liquid selection medium does not contain callus production hormones.

In some embodiments, selected transformed calluses are cultured in liquid selection medium (e.g., plates of selection medium) for about 2 to about 5 weeks, or more. For example, in some embodiments, selected transformed calluses are cultured in liquid selection medium for 2 weeks, 2.5 weeks, 3 weeks, 3.5 weeks, 4 weeks, 4.5 weeks or 5 weeks. In some embodiments, selected transformed calluses are cultured in liquid selection medium for 3 to 4 weeks.

In some embodiments, the cultures (e.g., callus induction medium, NPM and/or selection medium) are maintained at about 23° C. (e.g., 23° C.+/−5° C.) at optimum physical conditions of light (e.g., 16 hours of photoperiod).

Once the final selection step is complete, transformed calluses are transferred to semi-solid medium (e.g., selection medium) to boost regeneration/growth. At this point, transformed calluses may be cultured until genetically engineered progeny duckweeds are visible. In some embodiments, transformed calluses are cultured for about 4 to 10 days, or more, to produce engineered progeny duckweed. For example, in some embodiments, transformed calluses are cultured on semi-solid selection medium for 4, 5, 6, 7, 8, 9 or 10 days. In some embodiments, transformed calluses are cultured on semi-solid selection medium for less than a week (e.g., about 2 to 6 days).

Transient Transformation

In other aspects, provided herein are methods for transiently transforming duckweeds with a nucleic acid. "Transient transformation," as used herein, refers to the introduction of an engineered nucleic acid into a cell without insertion into a chromosome of cell. Methods for transiently transforming duckweeds (e.g., duckweed fronds) with a nucleic acid in accordance with the disclosure may comprise introducing an incision into the meristem tissue (containing undifferentiated meristematic cells) of duckweeds. In one embodiment of the disclosure, fronds from a 1-week- to 3-week-old (e.g., 2-week old) axenic culture are placed upside down on an in vitro cell culture plate. A small incision close to the meristem region is made using a needle (e.g., a 20 G×1½ in. needle), and then infection medium is delivered into the incision by using a syringe.

In some embodiments, the duckweeds are $Spirodela$ $polyrhiza$. For example, in some embodiments, the $Spirodela$ $polyrhiza$ are $Spirodela$ $polyrhiza$ 6581.

After the incision is made, the incision is infiltrated with (i) infection medium that comprises magnesium, a plant metabolizable sugar and acetosyringone and (ii) engineered $Agrobacterium$ $tumefaciens$, wherein the engineered $Agrobacterium$ $tumefaciens$ comprises a nucleic acid of interest, a selectable marker gene and a visible reporter gene, thereby producing infiltrated duckweeds. The term "infiltrating," as used herein refers to the forced introduction of bacteria (e.g., engineered bacteria) into a plant through a small opening in the plant (e.g., duckweed frond).

The "infection medium" used in the transient transformation methods of the disclosure is similar the infection medium used for the stable transformation methods, described above. Thus, the infection medium of the transient transformation methods comprises magnesium, a plant metabolizable sugar, and acetosyringone. In some embodiments, the infection medium comprises magnesium sulfate ($MgSO_4$), sucrose and acetosyringone. In some embodiments, the infection medium consists of magnesium sulfate ($MgSO_4$), sucrose and acetosyringone. In some embodiments, the infection medium comprises or consists of 10 mM $MgSO_4$, 10 g/L sucrose and 100 µM or 200 µM acetosyringone.

Following infiltration of the duckweeds, the duckweeds are cultured in liquid selection medium that comprises the selection substance and antibiotic, thereby producing cultured, infiltrated duckweed.

The "selection medium" used in the transient transformation methods of the disclosure is similar the selection medium used for the stable transformation methods, described above. Thus, the liquid selection medium of the transient transformation methods comprises a selection substance, antibiotic, basal salts and a plant metabolizable sugar (e.g., sucrose). In some embodiments, the selection medium comprises DL-phosphinothricin, carbenicillin, cefotaxamin, Shenk and Hilderbrandt (SH) basal salts and sucrose. In some embodiments, the selection medium consists of DL-phosphinothricin, carbenicillin, cefotaxamin, Shenk and Hilderbrandt (SH) basal salts and sucrose. In some embodiments, the selection medium comprises or consists of 10 mg/L DL-phosphinothricin, 200 mg/L carbenicillin, 500 mg/L cefotaxamin, 3.2 g/L SH basal salts and 10 g/L sucrose.

Duckweeds that have been successfully infiltrated and transformed express the visible reporter gene, and thus, may be identified based on the presence of a visibly detectable signal (e.g., fluorescent signal) in the cells of the duckweed. The visible reporter gene, as discussed above with regard to the stable transformation methods, may be a gene that encodes a visible marker protein that can be visualized without killing the duckweed. Examples of visible reporters are described above.

Nucleic Acids

A "nucleic acid of interest," as used herein, refers to any nucleic acid that can be introduced into an *Agrobacterium* (e.g., amiRNA and/or gene encoding a protein). As used herein, the term "nucleic acid" refers to at least two nucleotides covalently linked together, and in some instances, may contain phosphodiester bonds (e.g., a phosphodiester "backbone"). In some embodiments, a nucleic acid of the disclosure may be considered to be a nucleic acid analog, which may contain other backbones comprising, for example, phosphoramide, phosphorothioate, phosphorodithioate, O-methylphophoroamidite linkages, and/or peptide nucleic acids. Nucleic acids (e.g., components, or portions, of the nucleic acids) of the disclosure may be naturally occurring or engineered. "Engineered nucleic acids" include recombinant nucleic acids and synthetic nucleic acids. Engineered nucleic acids are not naturally-occurring nucleic acids, through it should be understood that they may contain naturally-occurring nucleic acid portions. "Recombinant nucleic acids" refer to molecules that are constructed by joining nucleic acid molecules (naturally-occurring or non-naturally occurring) and, in some embodiments, can replicate in a living cell. Recombinant nucleic acids, as a whole, are not naturally occurring. "Synthetic nucleic acids" refer to molecules that are chemically or by other means synthesized or amplified, including those that are chemically or otherwise modified but can base pair with, but are not themselves, naturally occurring nucleic acid molecules. Recombinant and synthetic nucleic acids also include those molecules that result from the replication of either of the foregoing.

The nucleic acids may be single-stranded (ss) or double-stranded (ds), as specified, or may contain portions of both single-stranded and double-stranded sequence (and, thus, may be considered partially single-stranded or partially double-stranded). The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xanthine, hypoxanthine, isocytosine, and isoguanine.

As used herein, a "promoter" refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive, inducible, activatable, repressible, tissue-specific or any combination thereof.

A promoter drives expression or drives transcription of the nucleic acid that it regulates. Herein, a promoter is considered to be "operably linked" when it is in a correct functional location and orientation in relation to a nucleic acid it regulates to control ("drive") transcriptional initiation and/or expression of that nucleic acid.

Target Genes

Aspects of the present disclosure are directed to modulating gene expression in duckweed. For example, target genes of interest may be downregulated (expression decreased), upregulated (expression increased) or misexpressed (expressed where the gene is not normally expressed) using methods as provided herein. In some embodiments, the present disclosure contemplates transforming duckweed with gene silencing constructs, including, without limitation, micro RNA constructs such as artificial micro RNA (amiRNA) constructs. In some embodiments, the present disclosure contemplates transforming duckweed with gene expression constructs, including, without limitation, those that include regulatory sequences such as promoters, enhancers, those that encode transcription factors (e.g., activators and/or repressors) and the like. An "activator" refers to a gene that activates (e.g., facilitates) gene transcription, and a "repressor" refers to a gene that represses (e.g., inhibits) gene transcription. Other regulatory sequences are known in the art and are contemplated herein.

Examples of transcription factors that may be used in accordance with the present disclosure include, without limitation, AP2, ARF, ARR-B, B3, BBR-BPC, BES1, C2H2, C3H, CAMTA, CO-like, CPP, DBB, Dof, E2F/DP, EIL, ERF, FAR1, G2-like, GATA, GRAS, GRF, GeBP, HB-PHD, HB-other, HD-ZIP, HRT-like, HSF, LBD, LFY, LSD, M-type, MIKC, MYB, MYB_related, NAC, NF-X1, NF-YA, NF-YB, NF-YC, NZZ/SPL, Nin-like, RAV, S1Fa-like, SAP, SBP, SRS, STAT, TALE, TCP, Trihelix, VOZ, WOX, WRKY, Whirly, YABBY, ZF-HD, bHLH and bZIP. Other transcription factors are known in the art and are contemplated herein.

Modulating the expression of enzymes, transport proteins and metabolic proteins is also contemplated herein.

Examples of enzymes that may be used in accordance with the present disclosure include, without limitation, oxidoreductases, transferases, hydrolases, lyases, isomerases, and ligases. In some embodiments, expression of one or more of the following enzymes is modulated: ADP-glucose pyrophosphorilase (AGP), monoacyglycerol acyltransferase 1 (MGAT1), MGAT2, MGAT3, diacylglycerol acyltransferase 1 (DGAT1), DGAT2, G-3-P by glycerol-3-phosphate acyltransferase (GPAT), LPA acyltransferase (LPAAT), phosphatidic acid phosphorylase (PAP), acetyl-CoA carboxylase, diaglycerol cholinephosphotransferase (CPT), phosphatidylcholine:diacylglycerol cholinephosphotransferase (PDCT), fatty acid desaturase 1 (FAD1), or fatty acid desaturase 2 (FAD2). Other enzymes are known in the art and are contemplated herein.

Examples of transport proteins that may be used in accordance with the present disclosure include, without limitation, peroxisomal ABC transporter1 (PXA1), trigalactosyldiacylglycerol 1 (TGD1), and sugar-dependent 1 (SDP1). Other transport proteins are known in the art and are contemplated herein.

Duckweed as System for Biofuel Production

Duckweeds are ideal candidates for biofuel production because of their robust growth in open culture and marginal aquatic environments, in addition to the relative ease of harvesting dry material. The dry weight biomass of duckweeds yields of 12-15 grams per square meter per day when grown on municipal wastewater in open ponds, with a starch content as high as 31% or 75% in some tissues. High-starch duckweeds have proven to be 50% more efficient than corn in ethanol production after enzymatic hydrolysis and yeast fermentation (Xu et al., 2011).

Provided herein, in various aspects and embodiments of the disclosure, are low-cost biofuel production methods using engineered duckweeds (e.g., duckweeds containing engineered nucleic acid). The stable genetic transformation methods of the disclosure may be used to produce engineered duckweeds that are useful for artificially controlling (e.g., modifying) the expression of genes such as, for example, those involved in metabolic pathways (e.g., fatty acid biosynthesis). In some embodiments, the engineered duckweeds may be used to identify and/or modify key genes for the production of triacylglycerides. The disclosure contemplates redirecting duckweed starch accumulation metabolism into triacylglycerol (TAG) synthesis by, for example, manipulating the expression of metabolic genes using the stable transformation methods provided herein.

As used herein, the term "engineered duckweed" refers to duckweed that is modified to contain a nucleic acid (e.g., exogenous and/or engineered nucleic acid) and to any progeny thereof, which progeny are not modified and which are descended from a modified duckweed produced by a method of the disclosure (e.g., a genetic transformation method).

Figures 2A, 2B:
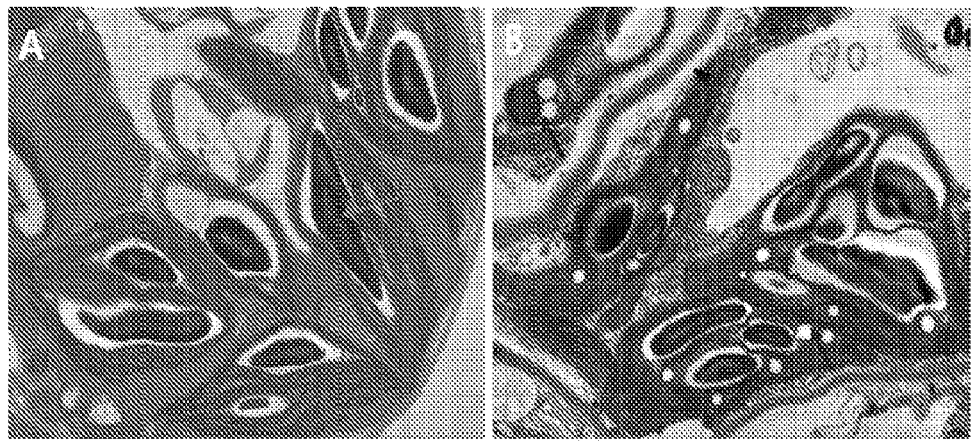
FIGS. 2A and 2B show transmission electron microscopy (TEM) images of *L. gibba* chloroplasts.

Natural synthesis and sequestration of TAG into cytosolic lipid bodies (FIG. 2) appear to be a protective mechanism by which duckweed cope with stress conditions, and thus the genes that are triggered in these pathways can be targeted and subjected to alterations in their expression to increase TAG production. In some embodiments, increased TAG accumulation may be achieved by blocking starch biosynthesis and thereby altering carbon partitioning. For example, TAG accumulation may be achieved by suppressing the gene that catalyzes the first committed step of the process and ectopically expressing a gene involved in the regulation of oil biosynthesis.

Artificial microRNA (amiRNA) for Genetic Manipulation

Figure 3:
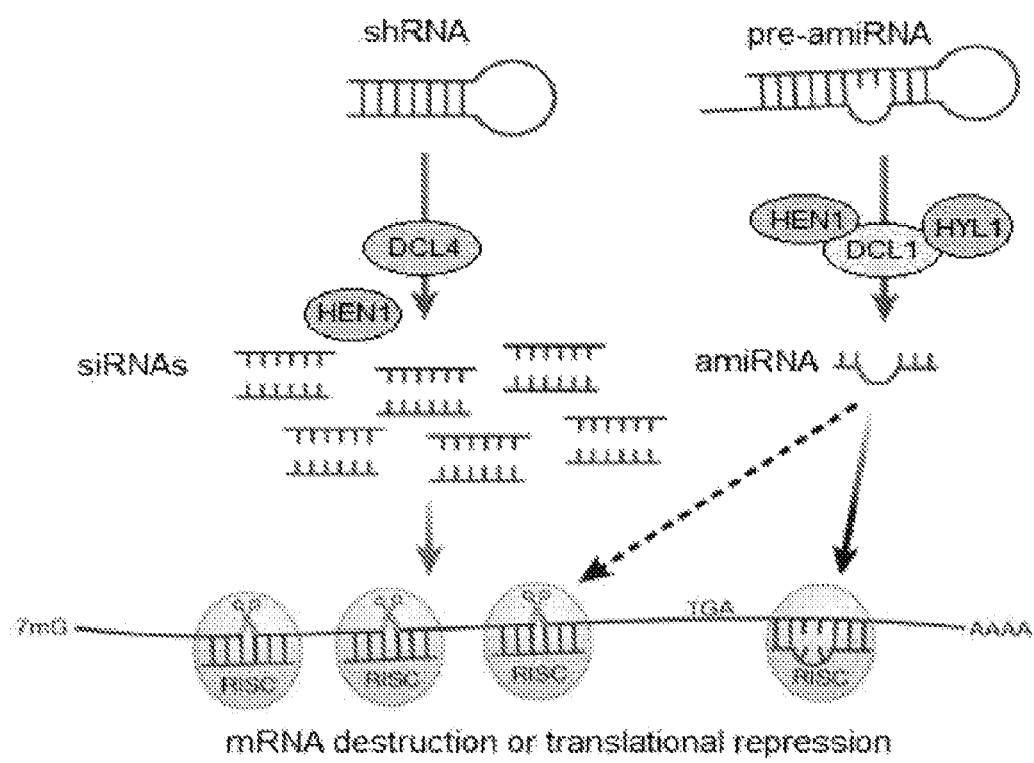
FIG. 3 shows a schematic of post transcriptional RNA silencing pathways by artificial constructs in plants. Dicer-like (DCL) 4 may be the preferred enzyme for production of 21-nt siRNAs from a shRNA. For pre-amiRNA, the combined nuclear action of DCL1, Hyponastic-leaves (HYL) 1 and HUA-enhancer (HEN) 1 produces a mature, methylated amiRNA. One siRNA or amiRNA strand incorporates into Argonaut 1 (AGO1)-loaded RNA-induced silencing complex (RISC) to guide cleavage of homologous RNA, leading to its degradation.

A microRNA (miRNAi) is a small non-coding RNA found in plants and animals and functions in transcriptional and post-translational regulation of gene expression. An artificial microRNA (amiRNA) is derived by replacing native miRNA duplexes from a natural miRNA precursor. An artificial precursor microRNA (pre-amiRNA) is normally processed such that one single stable small RNA is preferentially generated (FIG. 3), which facilitates the prediction of the complete spectrum of the amiRNA targets (Ossowski et al., 2008). amiRNAs technology has been successfully developed and adapted in several plant model systems (Warthmann et al., 2008a, Schwab et al., 2006, Molnar et al., 2009) and is an efficient and reproducible tool for highly specific gene silencing among different plant species.

Thus, various aspects and embodiments of the disclosure provide methods of silencing gene expression in duckweeds by expressing amiRNAs targeted against a gene of interest (e.g., a gene involved in TAG biosynthesis).

EXAMPLES

The Examples below describe experiments associated with the stable and transient transfection methods described in the present disclosure and in Canto-Pastor, et al. *Plant Biol.*, Jul. 2, 2014 (doi: 10.1111/plb.12215, Epub ahead of print), incorporated by reference herein in its entirety.

Example 1—Duckweed Transformation Methods

Construction of Expression Vectors for Duckweed Transformation

*Lemna gibba* (*L. gibba*) putative promoter sequences were isolated and amplified, and then they were cloned into a pENTR221 using the GATEWAY® cloning system. Sequences were later confirmed by sequencing with M13Fw and Rv oligonucleotide primers.

The efficiency of common exogenous promoters present in many widely used expression vectors was also tested. Exogenous *Zea mays* (*Z.* Mays) Ubiquitin promoter (ZmUB1p) and Cauliflower mosaic virus 35S promoter (CaMV 35Sp) were selected for this purpose. Both promoters were amplified from existing vectors and cloned as described for the endogenous promoters. Oligonucleotides ZmUB1pFw and ZmUB1pRv were used to amplify the *Z. mays* UB1p promoter, and oligonucleotides 35S Fw and 35S Rv were used to amplify the CaMV 35Sp promoter.

Figure 4:
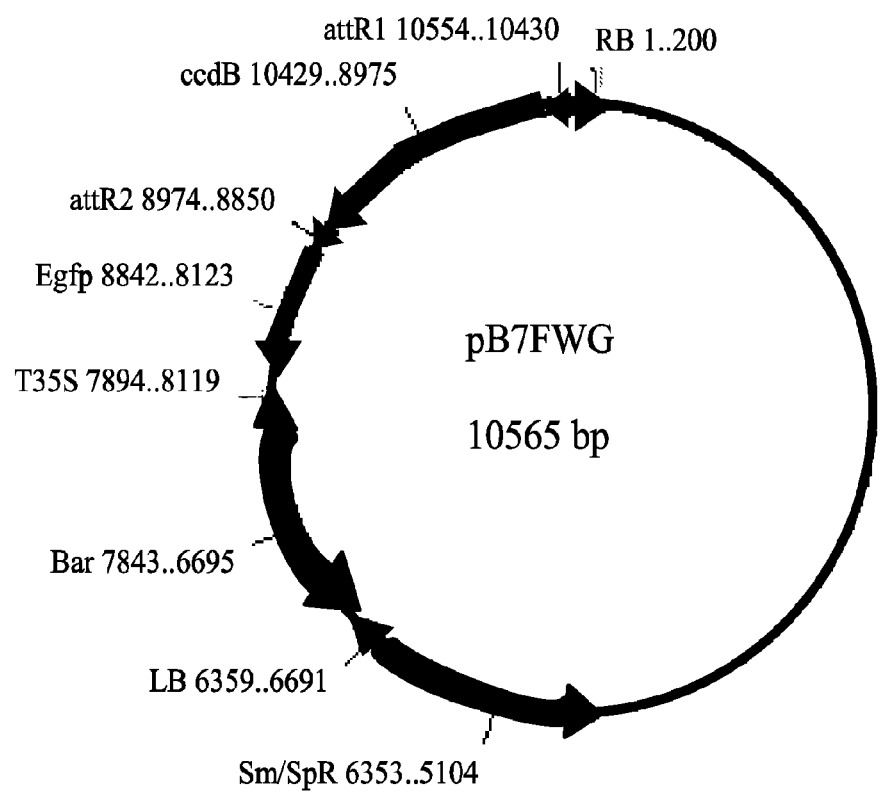
FIG. 4 shows a vector map of pB7FWG.

After all sequences were introduced into the GATEWAY® cloning system, a second reaction was performed to introduce the sequences into the destination vector, pB7FWG (FIG. 4) (Hajdukiewicz et al., 1994). After the constructs were correctly assembled, each was introduced into and transiently expressed in *Agrobacterium tumefaciens* (*A. tumefaciens*) strain GV3101. All promoters were successfully used in transformation assays, showing evident differences in expression levels in embryogenic tissue (FIGS. 14A-14E).

Transient Genetic Transformation of *Spirodela* Polyrhiza

An *Agrobacterium*-infiltration approach was developed and used for transient expression. *Agrobacterium* cells containing the vector of interest was grown overnight in 5 mL YEB media with selective antibiotics using an aliquot from the glycerol stock. A new culture of 50 mL of YEB was prepare using the same antibiotics with the addition of 100 μM final concentration of acetosyringone and 100 μL of the fresh *Agrobacterium* culture as a starter culture. The culture was then grown at 28° C. with shaking at 250 rpm until its $OD_{600}$ reached approximately 1.0. Subsequently, the solution was centrifuged for 15 minutes at 5000 rpm at 4° C. The supernatant was discarded, and the pellet was resuspended in infection medium with a 200 μM final concentration of acetosyringone and incubated at room temperature for approximately an hour.

*Spirodela polyrhiza* (*S. polyrhiza*) fronds were taken from a two-week old axenic culture and placed upside down on a plate. A small incision near meristem tissue (containing meristem stem cells that give rise to clonal progeny) located in a pocket (e.g., a recessed meristem) of the frond was made using a 20 G×1½ inch needle. Infection medium (10 mM magnesium sulfate $MgSO_4$ and 10 g/L sucrose) containing the infective *Agrobacterium* cells was infiltrated in the *Spirodela* frond by using a syringe that pressured the liquid inside the leafy structure through the previously-made incision. After the infiltration, the fronds were washed once with distilled water and then passed to half-strength SH medium for two days to permit transformation. Finally, the fronds were transferred to SH medium containing 200 mg/L carbenicillin and/or 500 mg/L cefotaxamin to restrain the undesired overgrowth of *Agrobacterium* and with 10 mg/L of DL-phosphinothricin (PPT) to block the growth rate of non-transformed fronds. Fluorescence was visible after 3 to 5 days of selection.

Figure 5:
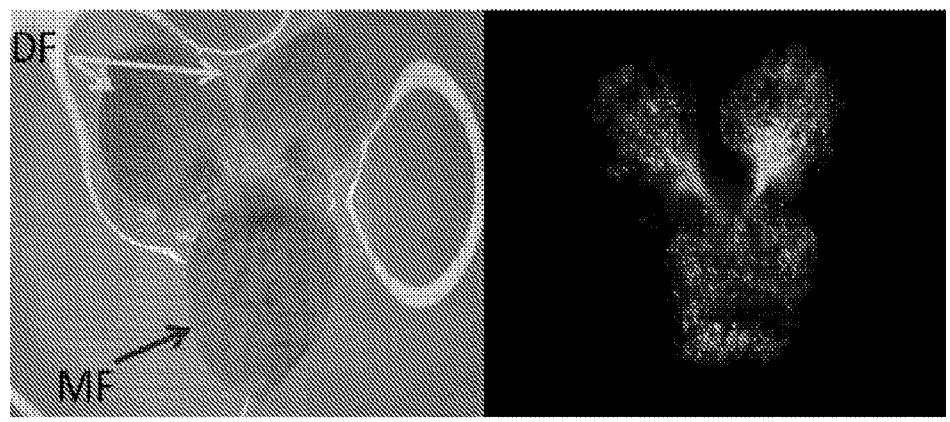
FIG. 5 shows images of expression of 35S:GFP (green fluorescent protein) in fronds of *Spirodela polyrhiza* (*S. polyrhiza*) 40 days after transformation. A mother frond (MF) and two daughter fronds (DF) connected by the stipe are shown. Mosaic expression in cell clusters across the fronds.

For each expression vector, GFP expression was detectable 3-4 days after inoculation and peaked after 5-6 days in more than 80% of the transformed fronds. Levels of GFP expression varied consistently among different promoters. The fluorescent signal was transmitted from the mother fronds to daughter fronds and detected in up to 18 successive generations (FIG. 5). Despite the initial success of the transformation, some unexpected characteristics arose during the process. GFP was not equally distributed throughout the fond, but was localized. Furthermore, potentially due to damage during the *Agrobacterium* infiltration process, fronds showed some developmental phenotypes such as cell damage and/or permanent infusion of the intercellular regions. These characteristics were surprisingly inherited and transported to progeny. Due to this damaged phenotype, the fluorescent signal was not transmitted completely to the subsequent generation, and the percentage of descendant fronds expressing GFP was reduced in successive generations. After 3 months, the GFP signal was undetectable or the growth of the fronds was arrested.

As described above, to restrain the undesired overgrowth of *Agrobacterium*, two days after transformation, the fronds were transferred to Shenk and Hilderbrandt (SH) medium containing antibiotics. Occasionally, severe contamination occurred in the culture after several weeks of selection, though before loss of GFP signal or growth arrest of the frond. Several PCRs performed on aliquots of the contaminated medium indicated that at least one of the bacteria growing in the media supplemented with antibiotics was the *Agrobacterium* used in the transformation assay, demonstrating that the selection medium was unable to eliminate the bacteria completely.

Figure 6:
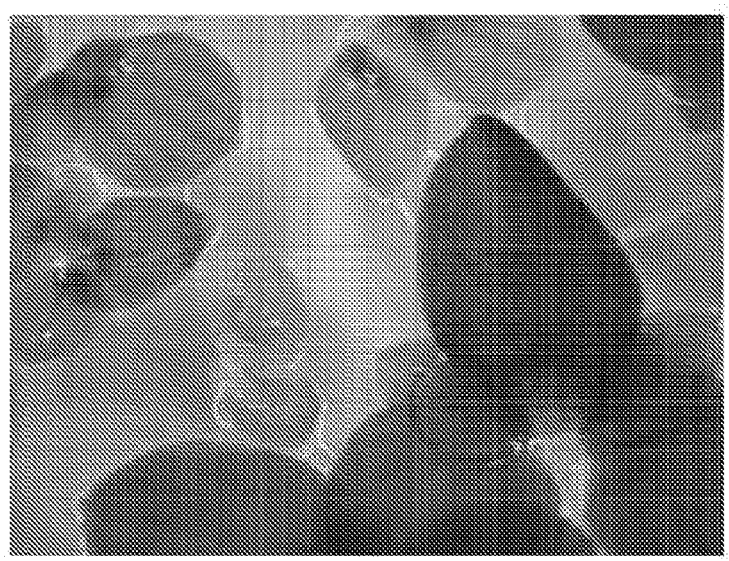
FIG. 6 shows an image of fronds injected with $H_2O$. After several generations, some of the fronds still inherited a sickly phenotype (e.g., permanent infusion can be seen in upper fronds as compared to lower ones).
Figures 7A, 7B, 7C, 7D, 7E:
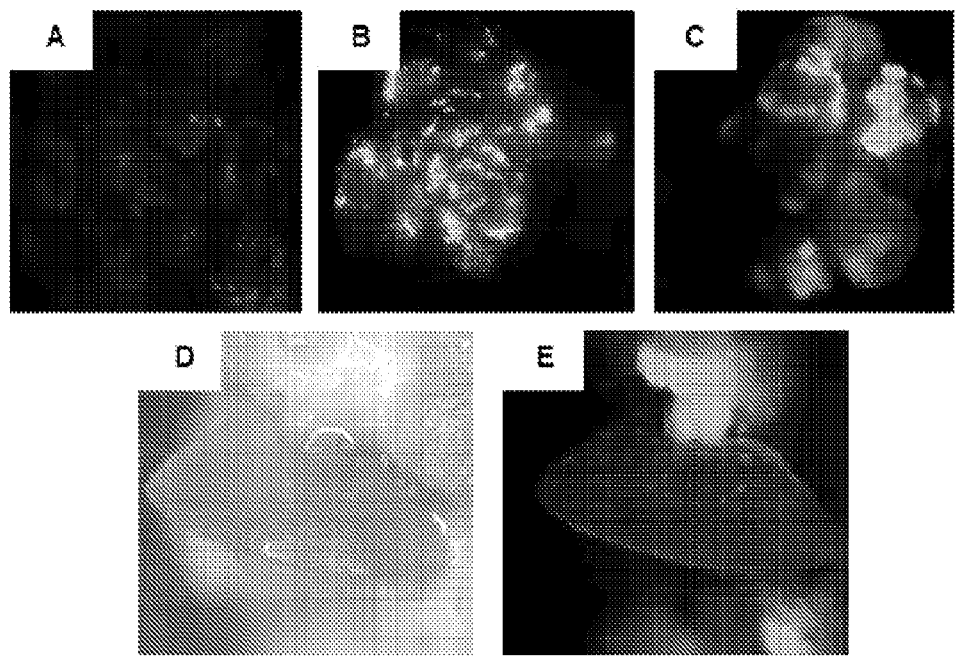
FIGS. 7A-7E show images of simultaneous selection and regeneration of stably transformed *L. minor* fronds expressing LgACTp:GFP. (A) Single cells expressing GFP, 5 days after co-cultivation. (B) Clusters of cells expressing GFP, 2 weeks after co-cultivation. (C) Whole regions of callus expressing GFP, 4 weeks after co-cultivation. (D and E) Transformed frond emerging from callus, 5 weeks after co-cultivation.
Figures 8A, 8B, 8C, 8D:
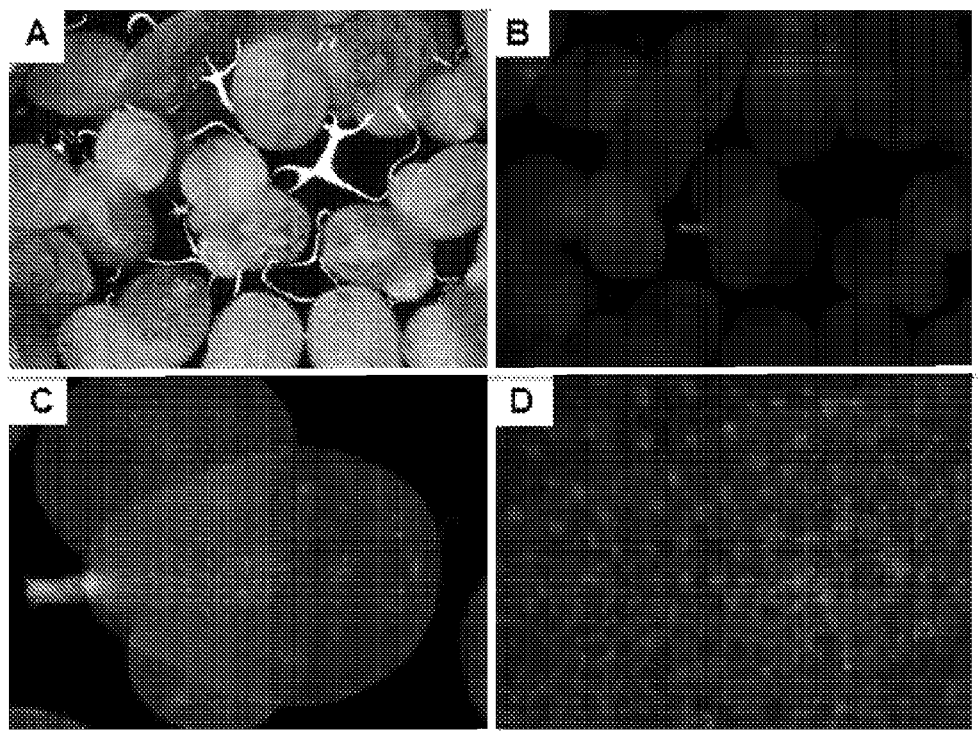
FIGS. 8A-8D show images of a transgenic line from *L. minor* expressing 35S:GFP. (A and B) All descendants from one single frond express GFP. (C) Meristematic tissue is transformed, and thus daughter fronds arising from a pocket express GFP. Homogeneous expression across all the cells with sparkles indicating accumulation inside certain regions of the tissue (D).
Figures 9A, 9B, 9C, 9D:
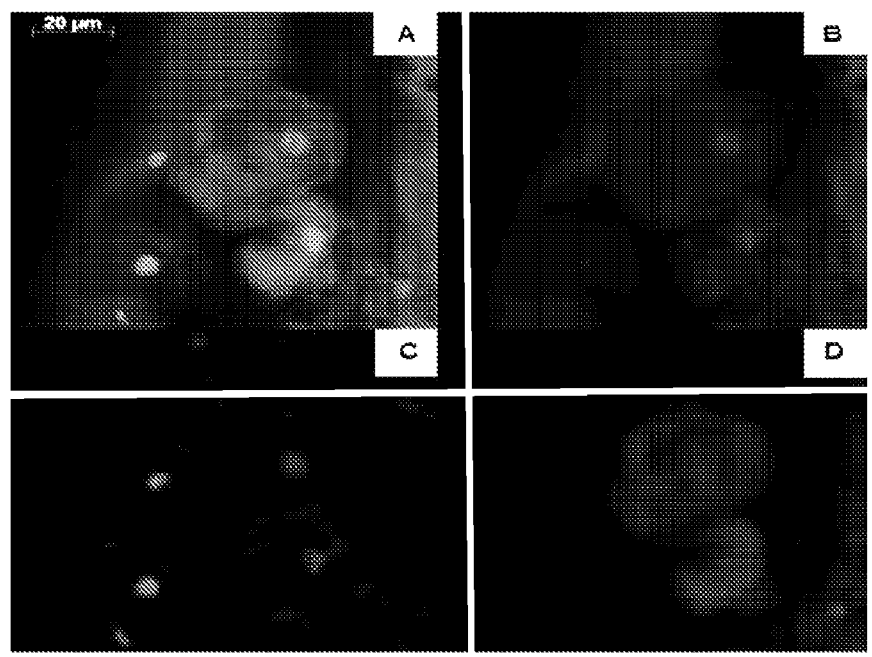
FIGS. 9A-9D show images of localization of GFP in epidermis and mesophyl cells. (A) Superimposed image shows ubiquitous presence of GFP in both epidermis and mesophyl cells. (B) Higher magnification reveals stronger fluorescence signal from nucleus, as revealed by (C) DAPI staining. (D) The presence of chlorophyll signal in mesophyll cells discards any trace of auto-florescence in GFP images.

To identify the cause of the developmental phenotypes that occur after transformation, an infiltration assay was performed using only sterile water (FIG. 6). Results showed the same pattern of permanent infusion of fronds inherited at the same ratio, indicating that the reason for the phenotype was not the presence of *Agrobacterium*, but rather the phenotype was likely a result of physical damage caused during the infiltration assay. Less aggressive infiltrations reduced the damage to the fronds, but transformation efficiency consequently decreased.

Callus Induction and Production of *Lemna minor*

Even after several attempts, callus could not be obtained from *L. gibba*. However, vigorous calluses from *L. minor* were produced and maintained for several weeks and were discarded and substituted for fresher cultures only to avoid the risk of acute somaclonal variation when regenerated.

Nine *L. minor* fronds from approximately 2-week-old cultures were placed on Callus Induction Medium (CIM) plates with the adaxial part of the frond in contact with the medium. The medium was refreshed whenever necessary. Three to four weeks later, light green masses of unorganized cells were selected and transferred to plates containing Nodule Production Medium (NPM). Tissue obtained from NPM after one week was used for transformation or partially transferred to fresh media. All tissue cultures were maintained at 25° C. under a 16 hour photoperiod of approximately 30 µmol/m² per second of white florescent light. The ease of growth of *L. minor* callus may permit a reduction in the time spent in induction stages, e.g., shortening the process to 4 weeks instead of the 6 weeks that is typically required using other methods.

Stable Callus Transformation and Selection of Transgenic *Lemna minor*

*Lemna minor* (*L. minor*) calluses were stably transformed using *Agrobacterium tumefaciens* (*A. tumefaciens*) GV3101 containing a vector of interest. The *Agrobacterium* cells containing the vector of interest was grown overnight in 5 mL YEB media with selective antibiotics using an aliquot from the glycerol stock. A new culture of 50 mL of YEB was prepare using the same antibiotics with the addition of 100 µM final concentration of acetosyringone and 100 µL of the fresh *Agrobacterium* culture as a starter culture. The culture was then grown at 28° C. with shaking at 250 rpm until its $OD_{600}$ reached approximately 1.0. Subsequently, the solution was centrifuged for 15 minutes at 5000 rpm at 4° C. The supernatant was discarded, and the pellet was resuspended in infection medium with a 200 µM final concentration of acetosyringone and incubated at room temperature for approximately an hour.

Calluses of approximately 3 mm in diameter were submerged in the culture with infection medium (10 mM magnesium sulfate $MgSO_4$ and 10 g/L sucrose) containing the *Agrobacterium* cells for 5 minutes. Without washing, calluses were then placed on nodule production medium (NPM) (4.4 g/L Murashige and Skoog (MS) basal salts, 30 g/L sucrose, 1 µM 2,4-dichlorophenoxyacetic acid, and 2 µM 6-benzylaminopurine) plates containing 100 µM acetosyringone, co-cultivated for two days, and then transferred to Shenk and Hilderbrandt (SH) (3.2 g/L SH basal salts) plates with 10 g/L sucrose, 200 mg/L carbenicillin, 500 mg/L cefotaxamin and 10 mg/L of DL-phosphinothricin (PPT) for two more days. Both cultivations were performed at 23° C. and 16 hours light conditions.

After the four days of co-cultivation with *Agrobacterium*, calluses presenting the greatest number of transformed cells were selected and transferred individually to 75 cm² cell culture flasks with vented caps containing liquid selective media without any callus production hormones (50 mL of SH medium 10 g/L sucrose, 200 mg/L carbenicillin, 500 mg/L cefotaxamin and 10 mg/L of PPT) and cultured in agitation at 100 rpm and 23° C. and with 16 hours light conditions. This selection process lasted for about 3 to 4 weeks, refreshing the media weekly. Once the selection was over, the liquid media was retired and the calluses were placed back on the same kind of SH plates to boost regeneration. In less than a week, the first regenerated fronds arose from the calluses (FIGS. 7A-7E). Transformed fronds were picked up and transferred to normal growth media. Generally, among non-fully transformed callus, non-transformed fronds appeared before any transgenic material was retrieved. Several transgenic plants representing individual clonal lines were generated from each flask containing rapidly growing callus nodules.

Characterization of Transgenic Lines and Analysis of Genomic DNA

Figures 17A, 17B, 17C, 17D, 17E, 17F, 17G, 17H, 17I:
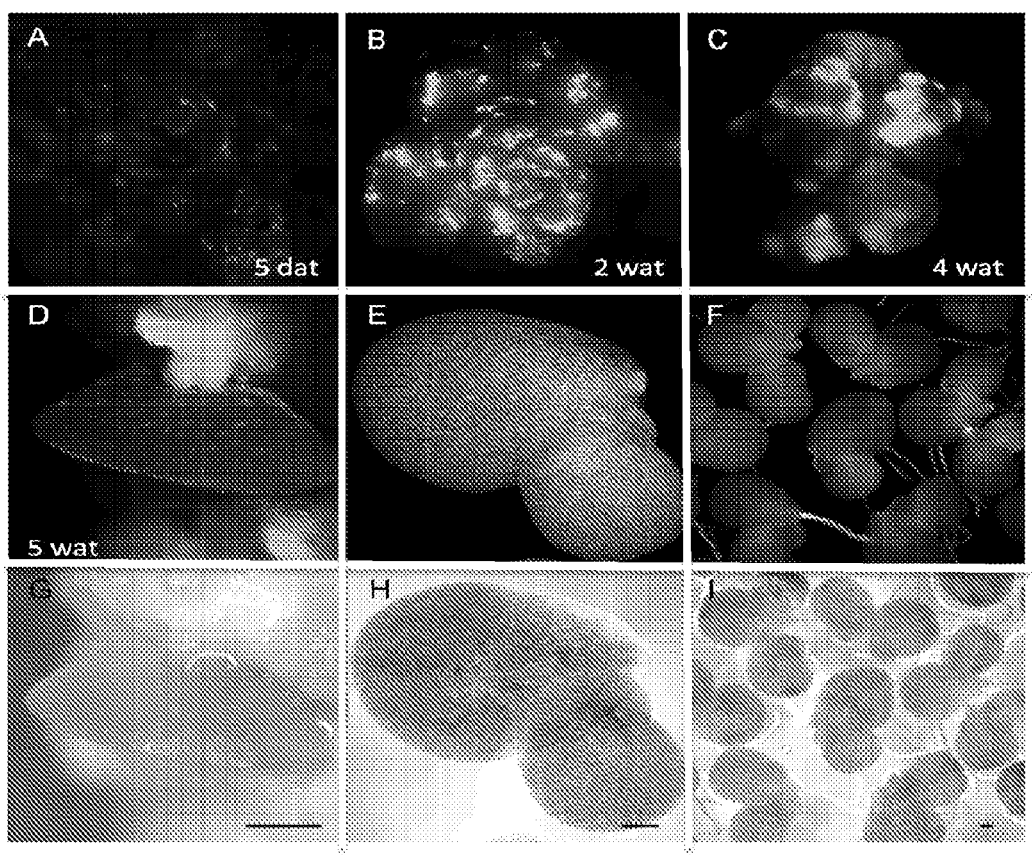
FIGS. 17A-17C show stable transformation and regeneration of L. minor callus with a GFP expression construct. Green fluorescence protein detected at various stages of selection in liquid media (A-C). Five weeks after transformation transgenic fronds began to regenerate from callus (D,G). Transformed fronds expressing GFP were regenerated with no phenotypic abnormalities (E,H), and the transgenes were stably maintained through generations (F,I). dat=days after transformation; wat=weeks after transformation. Scale bars: 1 mm.

In order to visually assist the selection process, eGFP was included as an in vivo reporter gene. Transgenic *Lemna* plants were maintained in normal growth conditions and screened regularly to confirm the stable maintenance of GFP expression in all descendants from individual clonal lines (FIGS. 8A-8D). The presence of speckles prompted an investigation of the pattern of protein accumulation inside the cells. For this purpose, samples were visualized with confocal microscopy. These studies revealed that, although there is ubiquitous intracellular presence of GFP, accumulation in certain regions such as cell walls and nucleus was observed in some cells (FIGS. 9A-9D). Transgenic calluses presenting the greatest number of cells expressing GFP after co-cultivation with *A. tumefaciens* were transferred to selective liquid media (FIG. 17A). Progressive growth of GFP positive cells was observed (FIG. 17A-17C). After five weeks in selection media, transgenic fronds began to regenerate from transformed calluses (FIG. 17D). Individual fronds regenerated from callus were transferred to standard growth media, and normal morphological characteristics were observed after the first frond generation (FIG. 17E). Transgenic lines had ubiquitous expression of GFP that was stably maintained for generation after generation (FIG. 17F).

Figures 18A, 18B, 18C:
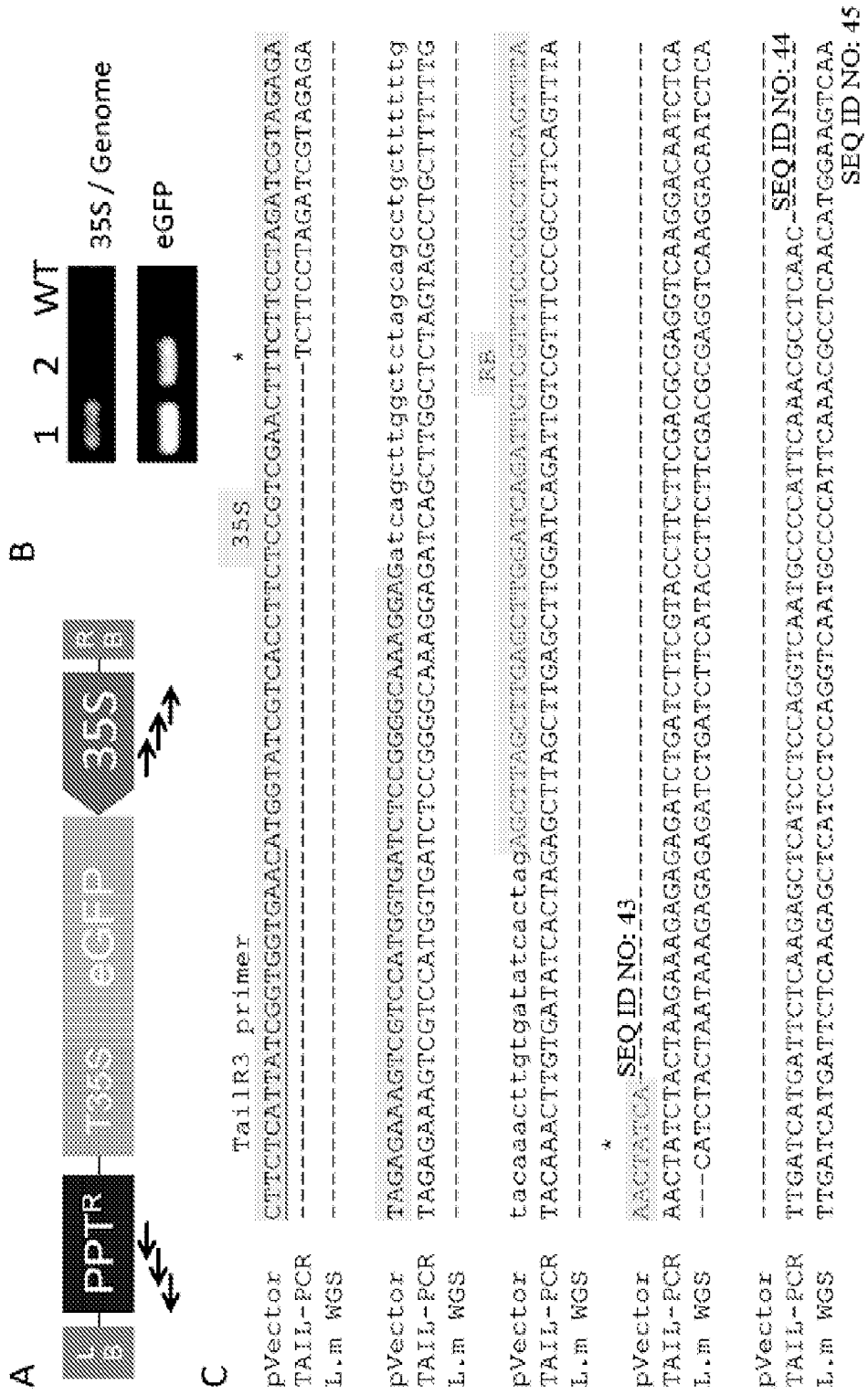
FIGS. 18A-18C show verification of T-DNA integration by thermal asymmetric interlaced polymerase chain reaction (TAIL-PCR). Primer locations for mapping genomic sequences flanking T-DNA insertions are depicted by arrows (A). Integration in two independently recovered lines and a L. minor wild type was verified with PCR (B). Alignments of TAIL-PCR right junction sequences of transgenic L. minor with de novo assembled whole-genome shotgun contigs (C).

The integration of T-DNA in the *L. minor* genome was tested using a Thermal Asymmetric Interlaced PCR (Tail PCR) assay. Tail PCR permits the identification of the unknown sequence flanking the T-DNA, revealing the insertion sites. The transgenic duckweed cultures used for Tail PCR were generated from various fronds (4 to 7) in fresh SH medium under optimal conditions and permitted to grow for two weeks before genomic DNA extraction. Using random degenerate and T-DNA specific primers, individual transformation events were screened (FIG. 18A). Several different border sequences were detected and then validated using a primer from the T-DNA and another from the flanking genome region. Internal cassette primers were used as a control for unique T-DNA insertions (FIG. 18B). The results from sequencing revealed that 50% of the lines tested contained at least two insertion events in their genome, while the others corresponded to single events. The sequences were maintained through different fronds, indicating that the integration was stable and no new integration events happened later. The recovered *L. minor* sequences were then reviewed in greater detail. With this technique several single insertion sites were recovered and efficiently mapped to preliminary sequence contigs of the *L. minor* genome (FIG. 18C). Localization of the insertion sequence was possible due to the identity present between known *L. gibba* genomic sequences and the recovered *L. minor* sequences.

Four days after *Agrobacterium* inoculation, 45 out 76 fresh calluses had clusters of transformed cells expressing GFP (59%). This transformation efficiency is significantly higher when compared to other studies (Chhabra et al., 2011) based on the original protocol (Yamamoto et al., 2001), where the efficiency obtained was 10% (34 transformed calluses out of 338 co-cultivated with *Agrobacterium*). The overall transformation duration (after callus induction) was also reduced from 6-7 weeks to 5 weeks.

Example 2—Artificial miRNA (amiRNA) in Lemnaceae gibba

The use of amiRNAs for the specific down-regulation of genes in *Lemnaceae* species was developed, in order to develop a functional platform of highly specific post translational gene silencing (PTGS).

Prediction and Amplification of Endogenous *Lemnaceae gibba* microRNA Precursors.

The transcriptomic and genomic sequencing data previously obtained (Ernst and Martienssen, 2012) was used to predict *L. gibba* microRNA (miRNA) sequences and their precursor sequenced. Predicted miRNA sequences were retrieved using technology developed for studies in soybean (Joshi et al., 2010). The combined sequencing and bioinformatics analyses identified initially 114 miRNA precursors, and then an additional 38 miRNA precursors, for a total of 152 miRNA precursors based on hairpin secondary structure features in the predicted precursors. Among these candidates, 9 miRNAs matched known miRNAs in *A. thaliana*, while 105 novel miRNAs were identified based on the general criteria for annotating plant miRNA (Meyers et al., 2008). Shared characteristics with previously validated precursors in other species make the predictions more reliable. Consequently, the orthologs of *A. thaliana* miR166a and miR319a were chosen for further studies. MiR166 is one of the few miRNAs present in both seed plants and mosses, therefore, its fidelity of processing should be more robustly conserved, which is a determining factor when it comes to designing miRNA/amiRNA substitutions. The sequence of the predicted precursor produced a short hairpin of 138 nt with imperfect complementarity of the passenger sequence (*miR166) in 3 different positions. *L. gibba* (Lg) pre-miR319 was also selected preliminary because, for years, it has been the backbone of choice to develop amiRNA libraries due to its extensive characterization (Schwab et al., 2006). However, it was discovered in *Physcomitrella patens* that the pre-miR319 contains a long loop that was subsequently shown to encode a second miRNA (Axtell et al., 2007). Lg miR319 was thus kept as a backup scaffold in case of failure of the adaptation of Lg miR166.

The sequences of several predicted precursors were isolated for each mature miRNA (lmn-0450, lmn-0631 and lmn-0697 for miR166; and lmn-0748 for miR319) from the genome; Specific oligonucleotides were designed to amplify the sequences from genomic DNA.

To evaluate the usefulness of the miR166 amiRNA backbone, a silencing assay targeting the duckweed homolog of *A. thaliana* CHLORINA 42 (CH42) was performed. CH42 encodes a magnesium chelatase subunit (CHLI), which is required for chlorophyll biosynthesis (Apchelimov et al., 2007). Its inactivation in *Arabidopsis* causes yellow-pale green tissue (Koncz et al., 1990). amiRNA knockdown approaches in *Arabidopsis* have been evaluated by targeting this gene due to this easily recognizable bleaching phenotype (Felippes et al., 2011; Felippes and Weigel, 2009; Werner et al., 2010). For *Lemna*, WMD3 with the *L. gibba* transcript assembly database was used to select candidate amiRNAs that would potentially lead to PTGS of CH42. Secondary structure of the miRNA precursor Lg-miR166 was predicted by RNAfold (ViennaRNA package 2). Both the miRNA and the *miRNA from the miR166 precursor were substituted with the amiRNA/*amiRNA. For the *amiRNA the structural and energetic features of the endogenous pairing, considered to be important for correct processing (FIG. 16A), were taken into account. The resulting amiR_CH42 targets the 3' UTR of the *L. minor* CH42. However, *L. minor* has two copies of CH42 with several single nucleotide polymorphisms (SNPs). One of these is located specifically in the binding region, opposite of position 13 of the small RNA (FIG. 16B). Overlapping PCR was used to generate the amiRNA-containing precursor, and then introduced into pB7WG2D using Gateway®-assisted cloning (FIG. 16C).

Figures 22A, 22B, 22C:
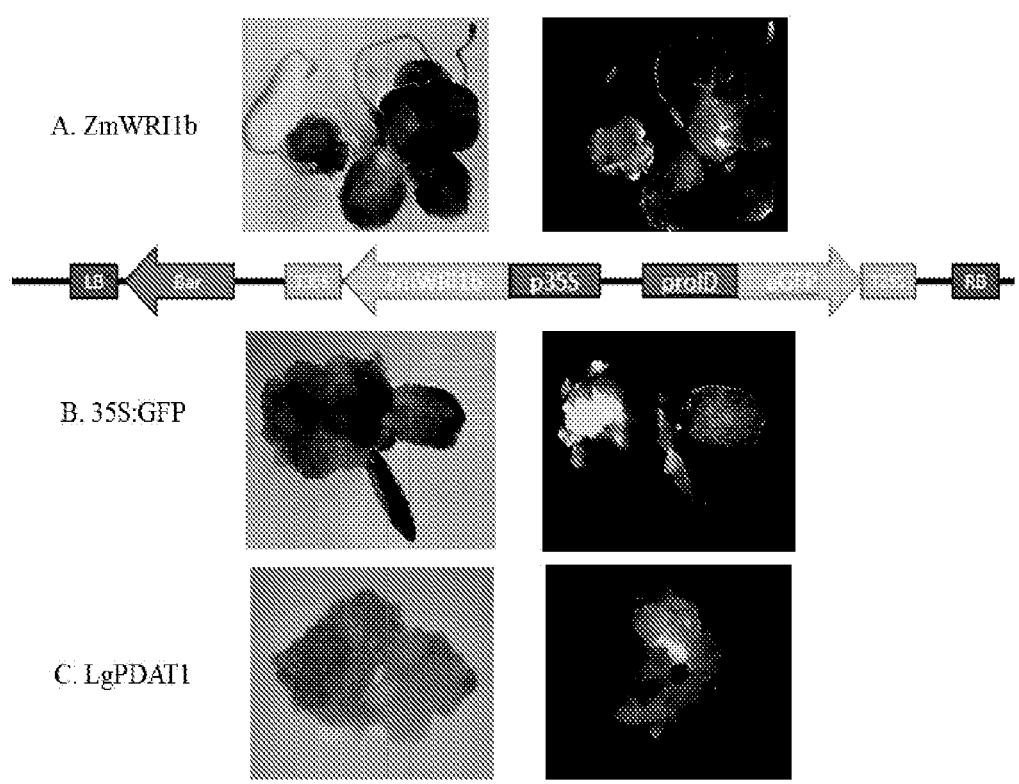
FIGS. 22A-22C show GFP expression in transformed duckweed (bright field images on the right and fluorescent images on the left).

Duckweeds were also transformed with constructs expressing PDAT1, DGAT1 (FIGS. 22C and 22B (control)) and WRI1b (FIG. 22A). Further, duckweeds were transformed with several different promoters, including a ubiquitin promoter, an actin promoter and a 35S promoter (FIGS. 22A-22C).

Construction of Expression Vectors and Plant Transformation.

Figure 10:
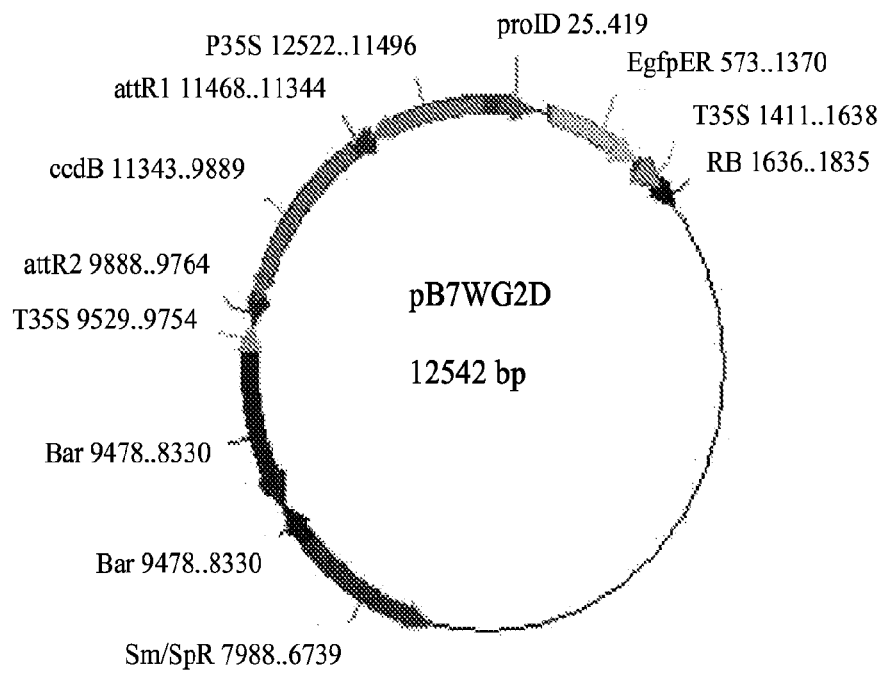
FIG. 10 shows a vector map of pB7WG2D. Virtual map using ApE-A plasmid Editor v2.

Once the correct isolation and amplification of the *L. gibba* predicted miRNA precursors was achieved, a strategy similar to that used to clone the promoters was used to clone the miRNA precursors. Sequences were introduced into the destination vector pB7WG2D (FIG. 10). The reporter gene (GFP) in this vector is in a location in an expression cassette that is different from the location of the inserted sequence of interest. Thus, any interference with folding and secondary structure of the precursor is avoided while maintaining, in the transformed cell, expression of a visible reporter gene.

Correctly assembled constructs were transformed into *A. tumefaciens* GV3101 and into *L. minor* callus to generate transgenic plants containing each of the described miRNA precursors.

Detection of miRNA Accumulation in Transgenic Lines.

Homologs of both miRNAs are well known in *A. thaliana*. Ath_miR166 and its targets regulate an array of developmental processes, including shoot apical and lateral meristem formation, leaf polarity, floral development and vascular formation (Kidner and Martienssen, 2004, Jung and Park, 2007). Ath_miR319, in particular, regulates TCP transcription factors, which have a role in leaf and petal growth and development (Nath et al., 2003, Nag et al., 2009). No abnormal phenotypes were observed in plants with increased expression of predicted ortholog precursors. Therefore, to test their functionality, an analysis was conducted to determine whether the increased expression of the generated constructs leads to a higher accumulation of the corresponding mature miRNA. For effective miRNA detection, a Northern blot analysis was performed. Total RNA was extracted from tissue of clonal lines grown in optimal conditions for two weeks.

Figure 11:
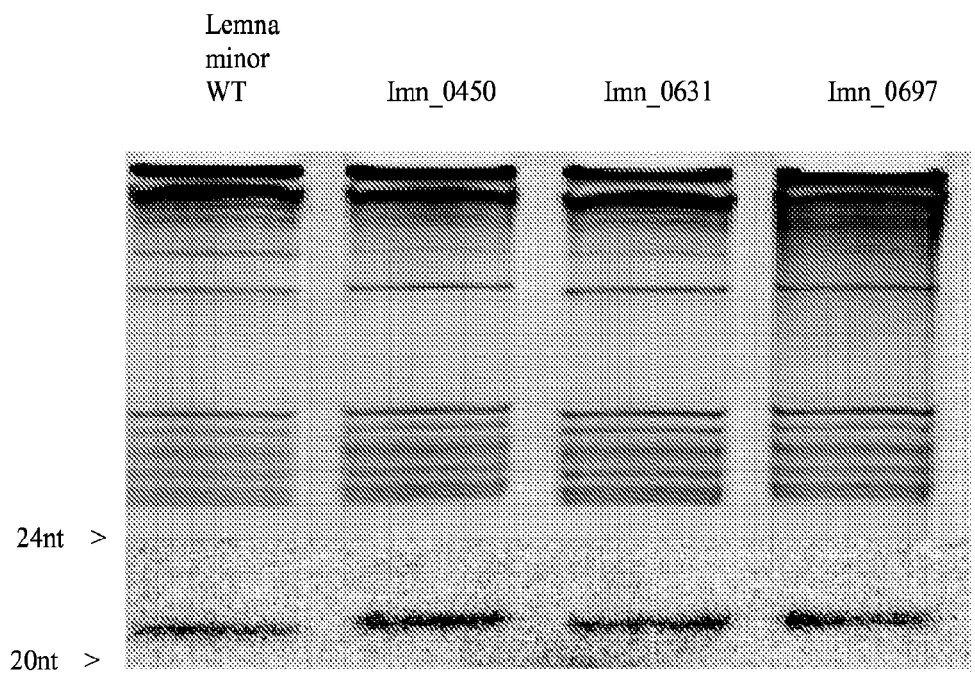
FIG. 11 shows a Northern blot of *L. minor* sRNAs (I). One wild type line and three lines overexpressing different predicted precursors of microRNAs using miR166 probe. The gel loading controls are shown stained with ethidium bromide; the bands correspond to the rRNAs and mRNAs (upper panel).
Figure 12:
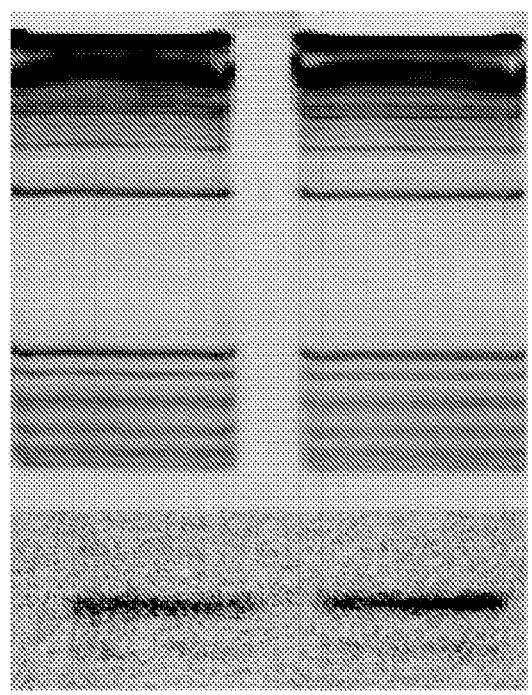
FIG. 12 shows a Northern blot of L. minor sRNAs (II). One wild type line and three lines overexpressing different predicted precursors of microRNAs using miR319 probe. The gel loading controls are shown stained with ethidium bromide; the bands correspond to the rRNAs and mRNAs (upper panel).

In the case of miR166, all three lines showed differential accumulation when compared to wild type. In addition, expression levels also varied among them, with the highest expression observed in Imn-0450 and Imn-0697 (FIG. 11). Therefore, the Imn-0697 precursor was selected as the first option for the design of an artificial miRNA precursor. The predicted precursor for miR319 also showed higher accumulation than wild type, validating it as a functional pre-miRNA (FIG. 12). However, as it might produce a second mature miRNA from a different loop, efforts focused on the miR166 approach.

Design of an Artificial microRNA

Before aiming for silencing any metabolic genes, it was necessary to check the functionality of the modified precursor. An assay was designed to target the *Lemna gibba* Phytoene desaturase (PDS) homolog. PDS catalyzes an early step in the carotenoid biosynthesis pathway. The absence of protective carotenoids results in bleaching through photo-oxidation of chlorophyll, making it a convenient gene for proof-of-principle applications. This strategy has been previously used in *Oryza sativa* because of its albino phenotype (Warthmann et al., 2008a).

The amiRNA design process used the parameters described below and was validated in preliminary studies (Schwab et al., 2006). The first step is to find candidate target regions in the selected gene that match amiRNA positional biases. The WMD platform (Web MicroRNA Designer; wmd3.weigelworld.org); developed by Dr Detlef Weigel and collaborators, Max Plank Institute) was used for this purpose. This tool automates amiRNA design, and only requires selection of candidates according to a small set of criteria. WMD was initially implemented for *Arabidopsis thaliana*, but has now been extended to several additional species for which genome or extensive EST information is available (Ossowski et al., 2008). It is designed to optimize both intrinsic small RNA properties, as well as specificity within the given transcriptome.

Figure 13A:
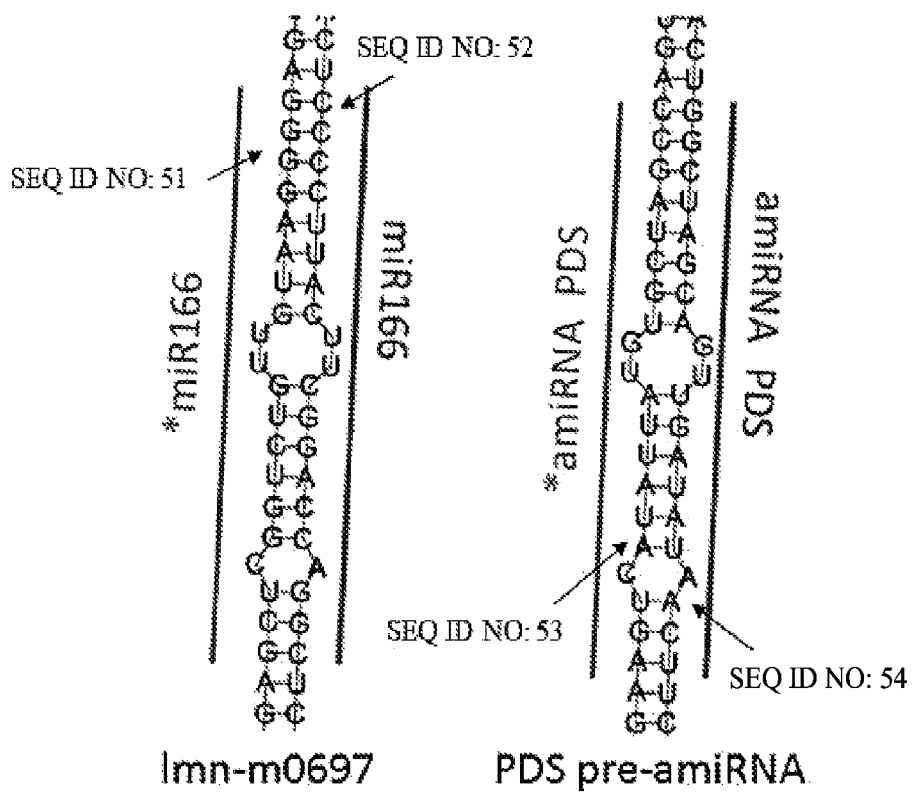
FIGS. 13A and 13B show schematics of the design of an amiRNA targeting phytoene desaturase gene (PDS) using lmn-0697 precursor as the scaffold. (A) Sequences substituted from the endogenous precursor conserve all required traits for correct processing. (B) Final secondary structure remains the same in both the endogenous and the amiRNA precursor. Folding of RNA by rna.tbi.univie.ac.at/cgi-bin/RNAfold.cgi.
Figure 13B:
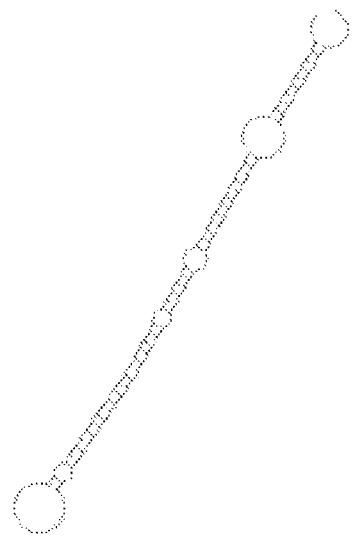
Figures 14A, 14B, 14C, 14D, 14E:
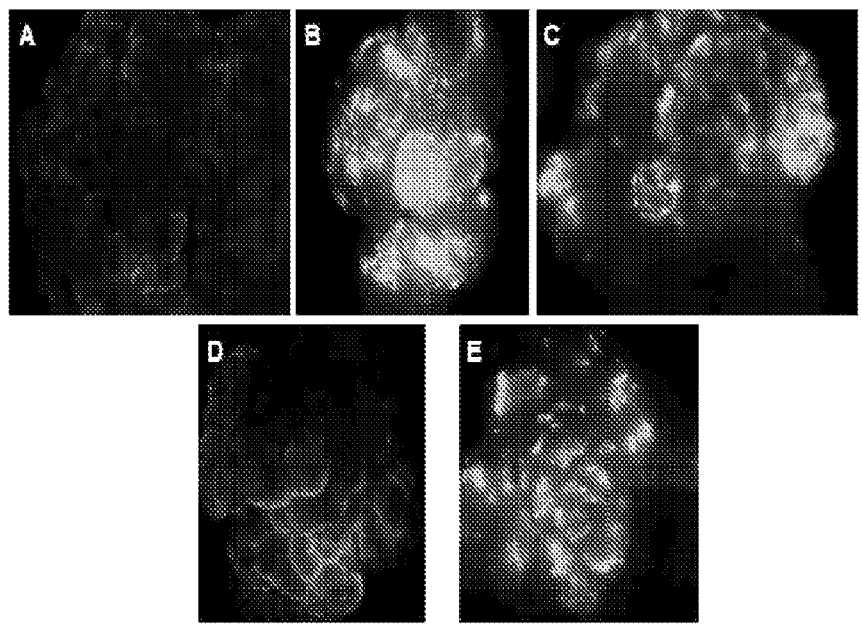
FIGS. 14A-14E show images of calluses transformed with different vectors and expressing GFP two weeks after co-cultivation with Agrobacterium tumefaciens. Callus transformed with pOXAC4, which contains LgSSU5Ap (A); with pOXAC1, which contains CaMV35Sp (B); with pOXAC2, which contains ZmUBIp (C); with pOXAC5 which, contains LgSSU5Bp (D); and with pOXAC3, which contains LgACTp (E).

The top amiRNA candidate design was selected for LgPDS to be engineered into the Imn-0697 backbone. Designing the complementary sequence (*amiRNA) required a study of the consensus characteristics of miRNA processing and the secondary structure of the precursor to ensure correct cleavage (FIGS. 13A and 13B). The whole modified precursor was synthesized by SGI-DNA (subsidiary of Integrated DNA Technologies).

Transformation and Silencing of Phytoene Desaturase (PDS) in Duckweed

Figure 15:
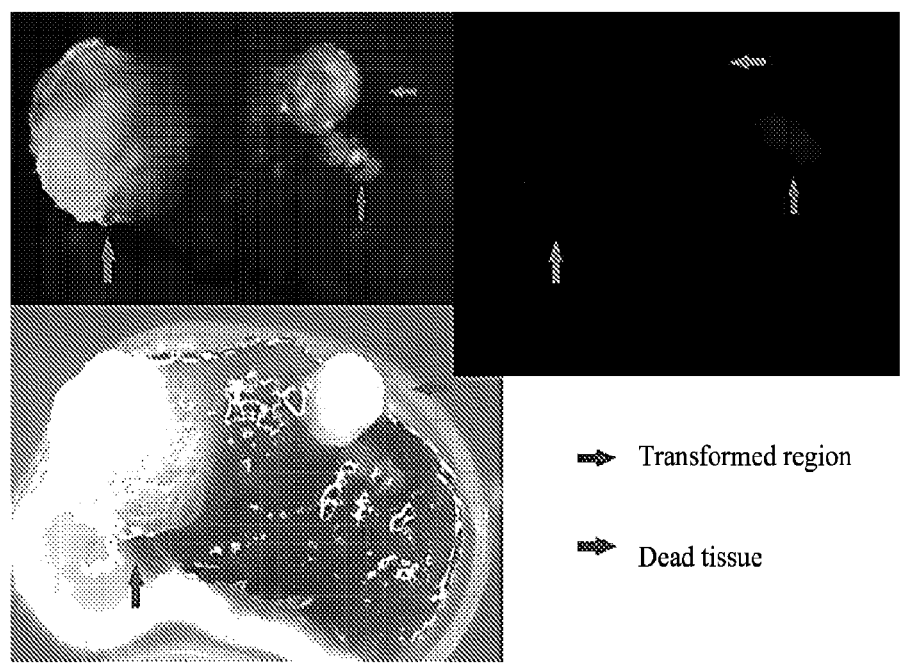
FIG. 15 shows images of inhibition of PDS by RNAi in transgenic callus (white, with GFP).

The synthetic pre-amiRNA was inserted in a pB7WG2D vector as described for the endogenous precursors. After introducing the final construct into *A. tumefaciens*, it was used to transform duckweed (FIG. 15). FIG. 15 shows images of inhibition of the phytoene desaturase gene (PDS) by RNAi in transgenic callus (white, with GFP).

Testing the Functionality of the amiRNA

Figures 19A, 19B, 19C:
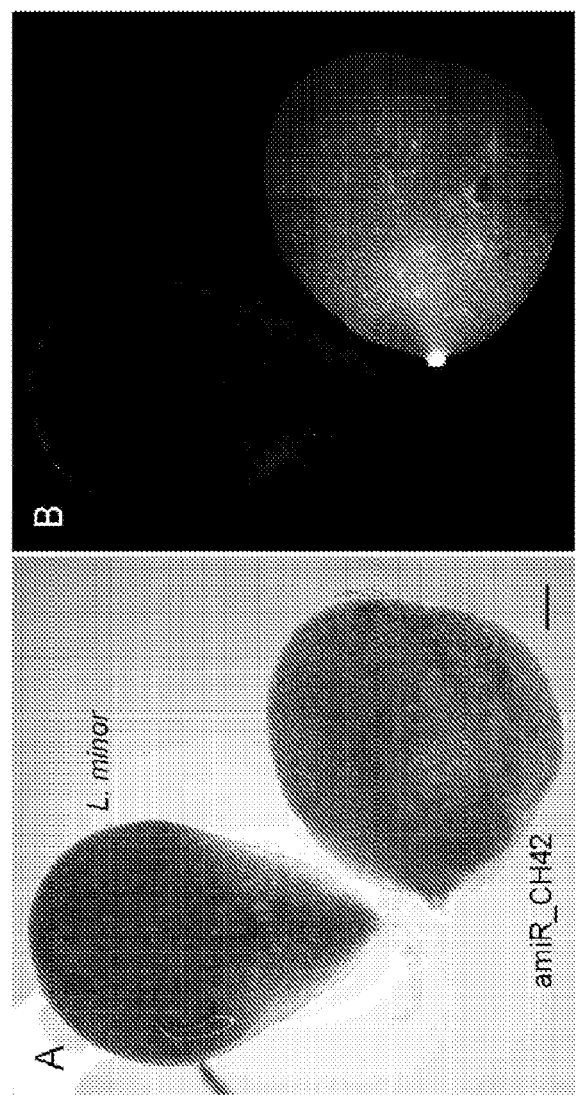
FIGS. 19A-19C show the phenotype of L. minor expressing amiRNA targeting CH42. Wild type L. minor and transformed amiR_CH42 fronds were observed under bright field (A) and fluorescence (B) conditions. Quantification of the chlorophyll content in L. minor and amiR_CH42 (C). standard deviation values are shown, n=3. Stars indicate significance in two-tailed z-test, ***P<0.0001. Scale bar: 1 mm.

To assess the silencing potency of the artificial precursor, transgenic lines containing the amiRNA construct described above for targeting CH42 (FIG. 19A-19C) were generated. Expression of the amiRNA resulted in reduced frond pigmentation (FIG. 19A-19B), resembling that observed in *A. thaliana* knockdown lines (Felippes et al., 2011). To confirm the bleaching phenotype was due to a decrease in chlorophyll content, chlorophyll was extracted from wild type and a transformed regenerant using 3 biological replicates. A significant decrease of approximately 40% in chlorophyll content was observed (FIG. 19C), consistent with previously reported observations in CH42-defective *Arabidopsis* mutants (Apchelimov et al., 2007; Soldatova et al., 2005).

Figure 20A:
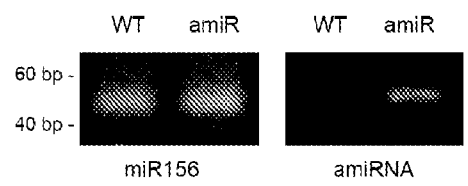
FIGS. 20A-20B show the expression of the amiR_CH42 and down-regulation of CH42. Stem-loop end-point real time PCR (RT-PCR) amplification of miRNAs, using endogenous miRNA (miR156) was used as an internal control (A). Changes in relative expression levels of CH42 mRNA were measured by quantitative RT-PCR (qRT-PCR) and normalized to Tubulin a mRNA (B). The standard deviation values for the qRT-PCR are shown, n=9. Stars indicate statistical significance in two-tailed Student's t-test, **P<0.002
Figure 20B:
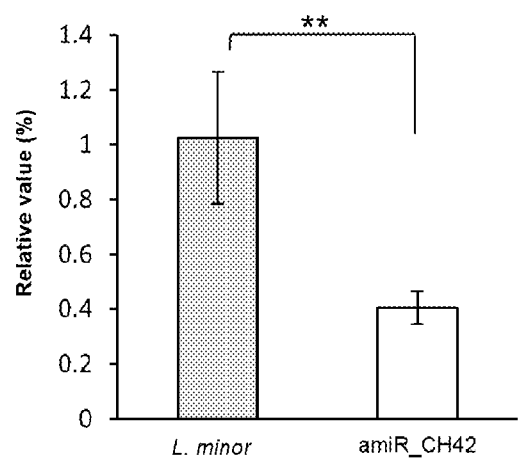

To estimate the degree of gene silencing, the accumulation levels of the amiRNA and the expression changes of CH42 were quantified. Using stem-loop end-point RT-PCR amplification, it was demonstrated that the transgenic lines accumulated amiRNA at significant levels (FIG. 20A). Once the presence of the amiRNA was confirmed, the extent of gene silencing was further characterized using quantitative reverse-transcription PCR (qRT-PCR) analysis. A significant decrease of approximately 60% in transcript abundance (FIG. 20B) was observed. Expression level of CH42, relative to α-Tubulin mRNA, was reduced by more than half; which was consistent with the phenotypic observations.

Numerous factors impact the degree of amiRNA-mediated silencing (Alvarez et al., 2006; Schwab et al., 2006) including mismatches at the binding site of the amiRNA, which could reduce or abolish endonucleolytic cleavage of mRNA targets by Argonaute-miRNA endoribonucleases (Molnar et al., 2009). To ensure that amiRNA expression resulted in gene down-regulation, 5'-rapid amplification of cDNA ends (RACE) analysis was performed in order to detect cleaved mRNA. The RACE products mapped to only one of the CH42 gene copies (CH42A), very close to the predicted cleavage site (FIG. 21). All 20 cleavage products mapped a few nucleotides downstream of nucleotide position 10/11 of the amiRNA, where Argonaute typically cleaves its targets, which could indicate secondary degradation of cleaved RNAs.

The mismatch at position 14 of the target site in the second copy CH42B seems to have a strong negative impact on the amiRNA-mediated silencing as no CH42B cleavage products were detected by RACE-PCR (FIG. 21). Similar mismatches have been shown to reduce silencing efficiency in rice (Warthmann et al., 2008). These data confirm the high specificity of the amiRNA silencing platform, as the amiRNA could specifically direct cleavage of only one of the two copies of the gene.

Materials and Methods

The following materials and methods were used in the experiments described in the above Examples.

Biological Material

The clones used in this study were *Lemna gibba* G3 DWC131 and *Lemna minor* 8627. Bacterial strains include *Escherichia coli* TOP10 (Invitrogen) for cloning purposes, and chemically competent *Agrobacterium tumefaciens* strain GV3101 with pSOUP carrying the different insertion vectors for callus transformation of *Spirodela polyrhiza* and *Lemna minor*. Chemically competent *Escherichia coli* strains ONE SHOT®MACH1™ T1® and ONE SHOT® TOP10 were used for plasmids amplification (INVITROGEN™ LIFE TECHNOLOGIES™). To assess the transformation efficiency, the pB7FWG,0 vector carrying the CaMV 35S promoter was introduced, and for the silencing assays, the pB7WG2D carrying the amiRNA precursor was introduced.

Plant and Tissue Culture Conditions

All duckweed species, including fronds of both *Lemna* species, were cultivated for 2-3 weeks in 50 mL liquid Schenk and Hildebrandt (SH) medium with 10 g/L sucrose at pH 5.6 (Schenk and Hildebrandt, 1972). In some instances, fronds and calluses were maintained at 23° C. under a 16-hour photoperiod of approximately 30 µmol/m$^2$ per second of white florescent light. Axenic cultures were refreshed when arrived to a confluent growth.

Tissue cultures were induced from *L. minor* fronds using a modification of existing protocols (Moon and Stomp, 1997). Fronds were incubated on Induction Medium (IM) containing 4.4 g/L Murashige and Skoog (MS) basal salts, 30 g/L sucrose, 5 µM 2,4-dichlorophenoxyacetic acid (2,4-D) and 0.5 µM Thidiazuron (TDZ) and 5 g/L of bacteriological agar (FISCHER SCIENTIFIC®) at pH 5.6. Medium was refreshed weekly. After three to four weeks, light green masses of unorganized cells were selected and transferred to solid Propagation Medium (PM) containing 4.4 g/L Murashige and Skoog (MS) basal salts, 30 g/L sucrose, 1 µM 2,4-D and 2 µM 6-benzylaminopurine (BAP) and 5 g/L of Agar at pH 5.6. After 7 to 10 days, the fastest growing calluses were propagated in fresh PM media and used in transformation assays.

Bacterial Media

All media used herein was autoclaved prior to use. The pH was adjusted to 7.2 using sodium hydroxide (NaOH), potassium hydroxide (KOH) and hydrochloric acid (HCl). For the preparation of selective media or agro-transformation media, 1/1000 volume of antibiotic or acetosyringone stock solutions were added, respectively, to the media when temperatures were below 55° C. because of heat sensitive stability of the compounds. For the preparation of plates, 15 g/L of Agar Bacteriological (Affimetrix(D)) was added.

Luria broth (LB-Lennox): 25 g/L LB-Lennox granulated (FISCHER SCIENTIFIC®)

Yeb Medium:

1 g/L yeast extract (FISCHER SCIENTIFIC®), 5 g/L beef extract (SIGMA-ALDRICH®), 5 g/L sucrose, 5 g/L peptone, and 0.5 g/L magnesium chloride $MgCl_2$.

Infection Medium:

10 mM magnesium sulfate $MgSO_4$ and 10 g/L sucrose (with addition of 100 µM or 200 µM acetosyringone).

Plant Media

All plant media was autoclaved prior to use. The pH was adjusted to 5.6 using sodium hydroxide (NaOH), potassium hydroxide (KOH) and hydrochloric acid (HCl). For the preparation of selection media or *agrobacterium* co-cultivation media, 1/1000 of antibiotic, herbicide, acetosyringone and/or some plant hormones stock solutions were added, respectively, to the media when temperatures were below 55° C. because of heat sensitive stability of the compounds. For the preparation of plates, 4.5 g/L to 5 g/L of Agar Bacteriological and optionally 1.5 g/L of PHITAGEL™ (SIGMA_ALDRICH®) were added.

Shenk and Hilderbrandt (SH):

3.2 g/L SH basal salts (GOLD BIOTECHNOLOGY®) Nodule Production Medium (NPM): 4.4 g/L Murashige and Skoog (MS) basal salts (SIGMA-ALDRICH®), 30 g/L sucrose, 1 µM 2,4-dichlorophenoxyacetic acid (2,4-D), and 2 µM 6-benzylaminopurine (BAP) (added after autoclaving).

Callus Induction Medium (CIM):

4.4 g/L MS basal salts, 30 g/L sucrose, 5 µM 2,4-dichlorophenoxyacetic acid (2,4-D), and 0.5 µM thidiazuron (TDZ).

Plasmids

All the constructs developed herein were obtained using the Gateway® cloning system. Thus, all the sequences were first cloned in a pDONR™ 221 vector and then transferred to the different destination vectors.

Oligonucleotides

The oligonucleotides provided herein (see, e.g., Table 2) were synthesized by Integrated DNA Technologies® and dissolved in UltraPure™ Distilled Water (Life Technologies®) to 100 mM concentration for stock storage. They were then further diluted to 10 mM for their use in polymerase chain reaction (PCR) assays. Additional oligonucleotides for the BP recombination reaction were designed by adding, to the corresponding sequences, the respective attB1/2 sites for cloning into a pDONR™ vector.

Polymerase Chain Reaction (PCR)

PCR is based on using a thermostable polymerase and a pair of oligonucleotides as primers for the subsequent amplification of a DNA sequence. This assay, in its different variations, permits a sensitive, fast and quantitative approach for the detection, characterization and duplication of DNA.

Nucleic Acid Isolation from *L. Gibba* Genome

For the cloning of *L. gibba* nucleic acid sequences into expression vectors, a previous amplification from a genomic extraction was necessary. Due to the complexity of the genome, a two-step PCR reaction was carried out.

Genomic DNA Extraction.

For the genomic DNA extraction of *L. gibba*, a slightly modified method from an existent protocol of CTAB extraction (Murray and Thompson, 1980) was used. Mixed Buffer was prepared with 10 mL of Extraction Buffer, 10 mL of Nuclei Lysis, 4 mL of Sarkosyl and 0.038 g of Sodium Bisulfite (Sigma Aldrich®) and was kept in continuous agitation. After 2 hours, 200 µL of the Mixed Buffer was added to the collected plant tissue and then ground with a pestle. After adding 500 µL more of Mixed Buffer, the solution was incubated at 65° C. for 15 minutes. Then, 700 µL of chloroform/isoamylalcohol (24:1) was added and inverted gently 10 times. The mixture was spun down (1 min at 13,000 rpm), and the supernatant was transferred to a new tube. A 2/3 volume of isopropanol was then added and mixed. The mixture was spun again (5 min at 13,000 rpm), and the supernatant was discarded. The pellet was washed with 70% ethanol and then dried on a heat block (65° C.) until the ethanol completely evaporated. Finally, the pellet was resuspended in 30 µL of ultrapure $H_2O$.

For extraction of total RNA from *L. minor*, DIRECT-ZOL™ RNA MiniPrep Kit (Zymo Research) was used following instructions of the manufacturer.

First PCR Reaction.

An initial amplification of the sequence of interest was performed. A 50 µL reaction was made using 1 ng of Genomic DNA as template and a set of designed primers (each about 50 bp upstream of the desired sequence). The reaction was performed following the specific instructions provided by New England Biolabs® for its Phusion® High-Fidelity DNA Polymerase. The annealing temperature of the reaction was set up using the TM-calculator of NEB® webpage (neb.com/tools-and-resources/interactive-tools/tm-calculator).

Agarose Gel Electrophoresis and Extraction.

For separation of amplified DNA fragments, an agarose gel electrophoresis was performed. Gels containing 1% w/v LE Agarose (BioExpress®) in TAE buffer were used for this assay. For visualization of DNA fragments under ultraviolet light, ethidium bromide (Sigma-Aldrich®) was added prior to polymerization of the gel. DNA samples were mix with 6× Loading Dye Solution (Thermo Fisher Scientific®), and electrophoresis was performed at a voltage of around 80 to 100 V/cm.

Due to the complexity of the *L. gibba* genome, the first PCR reaction usually led to amplification of several fragments. This may have been a consequence of nonspecific annealing of the primers with highly similar sequences around the genome. The band that corresponded with size to that expected from the PCR was then cut out of the gel and extracted using MinElute® Gel Extraction Kit (QIAGEN®).

Second PCR Reaction.

The final amplification reaction was performed using specific primers of the regions that were used to add the attB sites for introducing the sequence into the Gateway® cloning system. The second reaction was similar to that of the first, discussed above, with the exception that 1 ng of the gel extraction product was used as a template. The annealing temperature of the reaction was established using primer sequences without the attB sites.

After the second amplification reaction, the amplified PCR product was cleaned of reagents using QIAquick® PCR Purification Kit (QIAGEN®) and stored at −20° C.

Thermal Asymmetric Interlaced PCR (TAIL-PCR)

The purpose of this variation of the PCR is the isolation of an unknown sequence flanking a known one. Using this technique, it is possible to identify the insertion sites of the T-DNA within the genome of *L. minor*. To identify the insertion sites of the T-DNA, TAIL-PCR was performed as described (Liu et al., 1995), except that Ex Taq Polymerase (TaKaRa) was used in the first amplification to increase sensitivity.

First, an extraction of *L. minor* genomic DNA following the steps described in Polymerase Chain Reaction (above) was performed. Then, a series of three consecutive different PCR reactions were performed on the different samples using both specific primers of the inserted T-DNA and degenerated primers (AD) that will anneal randomly inside the genome.

Products of the second and third amplification were later analyzed running an agarose gel as described above in the section entitled Polymerase Chain Reaction, and different bands obtained in the third amplification were compared to those of the second. Only bands that changed size according to distance between T-DNA primers 2 and 4 inside the construct were rescued from the gel using MinElute® Gel Extraction Kit and sequenced using the T-DNA oligonucleotide from the third amplification (SB3-41SB5-4) as primer.

Northern Blot for Detection of Small RNAs

For the detection of mature microRNA from *Lemna gibba* and *Lemna minor*, a slightly modified version of an already existent protocol (Várallyay et al., 2008) was used.

RNA Extraction from *Lemna minor* and *Lemna gibba*:

RNA from the desired sample was extracted as described in the section entitled Quantitative Reverse Transcription PCR (qRT-PCR).

Polyacrylamide Gel Electrophoresis:

A polyacrylamide gel was used for separating RNA sequences in relation to their size. For preparation of the gel, a solution containing 15% of (19:1) acryl:bisacryl and 7 M urea in 0.5×TBE was made. The solution was placed at 65° C. until the urea was completely dissolved, and then the solution was poured to a new recipient to remove dissolved air.

For polymerization of the gel, 250 µL of 10% ammonium persulfate (APS) and 20 µL of tetramethylethylenediamine (TEMED) were added to 50 mL of the previous solution, and it was poured inside a vertical slab assembly for gels. After 1 hour, the gel was fully polymerized. The comb (to make wells) was then removed, and the wells were washed with 0.5×TBE to reduce urea seepage into the wells. The gel was pre-run at 300 V for more than 30 minutes in 0.5×TBE.

RNA samples were brought to the final amount (e.g., µg) desired to load with UltraPure™ Distilled Water, and then an equal volume of Ambion® RNA Gel Loading Dye II was added. The mixture was heated for 5 minutes at 65° C. to disrupt secondary structure and then placed on ice.

After the pre-run of the gel, the wells were washed again. Then, RNA samples were loaded and run at 100-300 V until lower dye (Bromophenol blue (BPB)) from the loading buffer was close to the bottom. In this gel, BPB runs at 10 nucleotides while xylene cyanol (XC), which should be at the middle, runs at about 40 nucleotides. The upper part of the gel containing high-weight RNAs was cut out, stained with ethidium bromide, and used as a loading control.

Blotting:

For this step, six pieces of Whatman® 3MM Chr Blotting Paper and a single piece of GeneScreen Plus® Hybridization Transfer Membrane (Perkin Elmer®) were cut to fit gel. RNA was transferred to the nylon membrane using Trans-Blot® SD Semi-Dry Transfer Cell (BioRad®). Soaked papers were placed on the transfer block, followed by the soaked membrane, the gel, and the rest of soaked papers on top. All air bubbles were then removed to ensure a perfect transfer. After the setup of the apparatus, the transfer was done at max power for 45 minutes. Finally, the RNA was bonded covalently to the membrane with shortwave 254 nm UV light from a CL-1000Crosslinker (UVP, LLC).

Hybridization:

The nylon membrane was rinsed with water to remove salts and urea and then pre-hybridized with 20 mL of Ambion® ULTRAhybO-Oligo buffer (Invitrogen™) at 40° C. for at least 1 hour. For detecting miRNAs, a complementary oligonucleotide was designed as probe. For probe preparation, 1 µL of 10 µM oligo, 16.5 µL of UltraPure™ Distilled Water, 2.5 µL of 10×T4 Polynucleotide Kinase buffer (NEB®), 3 µL of ATP N-32P1-3000 Ci/mmol 5 mCi/ml (Perkin Elmer®) and 2 µL of T4 Polynucleotide Kinase were mixed, and the labeling reaction proceeded for 1 hour at 37° C. Then, 200 µL of hybridization buffer were added to the probe and heated to 95° C. for 5 minutes. After the incubation, the probe was chilled in ice for 20 seconds and then added directly to the pre-hybridizing blot. The blot was left overnight at 40° C.

Washing and Revelation:

Nylon blot was washed twice with 2×SSC buffer with 0.2% SDS (Sigma Aldrich®) for 15 minutes and then wrapped in plastic wrap to avoid drying of the membrane while exposing. Northern blot was exposed overnight on an imaging plate BAS-MS2040 (FujiFilm®) and signal was analyzed with a FLA-5100 Fluorescent Image Analyzer (FujiFilm®).

GATEWAY™ Cloning of Sequences into Expression Vectors

All the expression vectors were elaborated using the GATEWAY™ cloning system designed by Invitrogen™.

BP Reaction:

The first step was the introduction of the sequence of interest inside the system by creating a Gateway® entry clone. Once the sequence was amplified by PCR with flanking attB sites as described above, the product was recombined into a pENTR221 using a Gateway® BP Clonase®, following the manufacturer's instructions. After recombination, the product was then cloned into *E. coli* as discussed elsewhere herein.

First Plasmid DNA Extraction and Sequencing:

After incubating overnight the resistant, an extraction of total plasmid DNA was performed on the cultures using QIAprep® Spin Miniprep Kit (QIAGEN®), following the manufacturer's instructions. Once extracted, the samples were quantified using a NanoDrop ND-1000® Spectrophotometer, and an aliquot of the sample was sent for sequence using M13Fw/Rv primers to confirm that the sequence has been amplified and introduced correctly into the vector.

LR Reaction:

After confirming that the sequences were correct, the sequences were introduced into the desired destination vector (pB7FWG,O/pBWG2D) by recombination using a Gateway® LR Clonase®, following the manufacturer's instructions. After recombination, the product was then cloned into *E. coli* as described elsewhere herein.

Second Plasmid DNA Extraction and Checking:

Extraction of total plasmid DNA and quantification was again performed on the cultures as described elsewhere herein. Confirming correct recombination was achieved by sequencing or by PCR. Oligonucleotide sequences specific for the destination vector (eGFP5'Rv for pB7FWG,0/ 35S3'Fw for pBWG2D) and for the introduced sequence were used as primers. Plasmids were stored at −20° C.

Transformation of *Escherichia coli*

Use of *Escherichia coli* for amplification of the desired DNA constructs is a well-established tool that permits fast and easy multiplication of specific plasmids for further experiments. Taking advantage of a specific resistance conferred by the plasmid to the bacteria, transformed cells were selected exclusively.

ONE SHOT® TOP10 and MATCH1™ T1® Chemically Competent *Escherichia coli* strains were transformed following manufacturer's instructions. After transformation, the cells were plated in LB media containing appropriate antibiotic for selection and incubated overnight at 37° C. Colonies that Grew in presence of the antibiotic were selected and individually cultured overnight at 37° C. in 5 mL of LB with the corresponding antibiotic. The final culture was used to perform further experiments.

Production of *Agrobacterium tumefaciens* Competent Cells

Chemically competent *Agrobacterium tumefaciens* cells were grown in 5 mL of YEB with rifampicin and gentamicin (selection antibiotic for the strain of *A. tumefaciens*—GV3101 with pSoup) overnight at 28° C. with shaking at 250 rpm. This culture was diluted in 100 mL of LB and cultured until the $OD_{600}$ was between 0.5 and 1. The culture was then chilled on ice and centrifuged for 5 min at 5000 rpm at 4° C. The pellet was resuspended with 1 mL of 20 mM $CaCl_2$ and 20% glycerol. Finally, 100 µL aliquots were made and thawed in liquid $N_2$. Samples were stored at −80° C.

Transformation of *Agrobacterium tumefaciens*

To introduce the gene of interest in the chemically competent *Agrobacterium tumefaciens* strain, the competent cells were thawed on ice for 10 minutes. Next, 1 µL of plasmid DNA of interest was added to the cells and incubated for 30 minutes on ice. The cells were then frozen in liquid $N_2$ for a minute. The cells were then heat shock at 37° C. for 5 minutes with occasional mixing. Subsequently, 1 mL of YEB medium was added to the cells, and the cell culture was incubated for at least 1 hour at 28° C. with shaking at 250 rpm. The cells were then pelleted, resuspended in 100 µL, and plated in YEB with the selective antibiotic at 28° C. until colonies were visible. For *Escherichia coli* transformations, colonies that grew in the presence of the antibiotic were selected and cultured individually in 5 mL of YEB overnight at 28° C. with the specific antibiotic. The final culture was used to perform further experiments.

Transformation and Regeneration of *Lemna minor*

*A. tumefaciens* GV3101 carrying the vector of interest was cultured in LB with selective antibiotics and 100 µM acetosyringone at 28° C. to an OD600 of 1.0. Cells were resuspended in 10 mM magnesium sulfate, 10 g/L sucrose and 200 µM acetosyringone and incubated at room temperature for 1 hour. Calluses of approximately 3 mm in diameter were submerged in the bacterial suspension for 5 min. Calluses were then placed on NPM with 100 µM acetosyringone and co-cultivated for two days. Transformed calluses were transferred to solid Regeneration Medium (RM) containing 10 g/L sucrose, 200 mg/L carbenicillin, 500 mg/L cefotaxamin, 10 mg/L of phosphinothricin (PPT) and 5 g/L of bacteriological agar at pH 5.6 for two more days.

All the transformations performed in this study use eGFP as a reporter gene, driven by the CaMV 35S promoter in the pB7WG,0 and by the *Agrobacterium* rolD promoter (promoter present in *Agrobacterium rizhogenes* T-DNA for high expression of an oncogene in the host). Calluses with the greatest number of GFP expressing cells were transferred individually to 75 $cm^2$ cell culture flask with vented cap containing 50 mL of liquid RM and cultured in a shaking incubator at 100 rpm. After 4 weeks, refreshing the media weekly, calluses were placed back on solid Regeneration media. Regenerated fronds arising from the callus were transferred to liquid standard growth media and screened for fluorescence.

*Lemna gibba* miRNA precursor prediction

Total RNA was isolated from frozen *L. gibba* G3 tissue by grinding in a mortar and pestle under liquid nitrogen followed by TRIzol (Invitrogen) reagent extraction as recommended by the manufacturer. Small RNA libraries were prepared and sequenced by Fasteris. Briefly, 10 µg total RNA was size selected twice by acrylamide gel electrophoresis, before and after RNA adapter ligation. Adapter-tagged RNA fragments shorter than 30 bp were then reverse transcribed, PCR amplified, and gel purified. 74M reads were obtained from a single HiSeq 2000 1×100 bp run. 3' adapters were trimmed from the raw reads. Subsequently, *L. gibba* small RNA sequences were mapped to genomic scaffolds from the *L. gibba* v0.1 assembly (http://www.lemna.org), and filtered to remove t/r/sn/snoRNA, redundant and high copy reads. The sRNAs that passed this filter were tested for their precursor structure using miREAP. Precursors were defined by extending from the potential miRNA on either side, up to 200 nt. After this, two additional filters (strand-bias and top1+top2 ratio) were applied to distinguish miRNA from siRNA loci. Strand-bias is the sum of sRNA abundance on sense strand divided by the total abundance on both strands. Top1+top2 is the proportion of the abundance of top two abundant tags, also referred as the "distribution filter". The cut-off was picked based on known miRNAs from *Arabidopsis* and rice. During each step, the remaining number of known Ath-miRNA (miRBase v17) was tracked as an indicator of the efficiency of the filtering. The miRNA prediction pipeline here described with further details of the filters explained can be found in a previously published protocol (Thai et al., 2011).

Artificial microRNA Construct Design

To automate the amiRNA design process, the WMD3 web-service was installed on the lemna.org server for use with *L. gibba* de novo transcriptome assemblies. After identifying transcripts of target genes by homology with *A. thaliana*, WMD3 was used to generate candidate 21nt mature amiRNA sequences that resemble natural miRNAs while minimizing possible off-target effects to other transcripts (Ossowski et al., 2008).

The 21nt candidates were introduced into a *L. gibba* pre-miR166a backbone as described (Schwab et al., 2006) and then cloned into a pB7WG2D vector (Karimi et al., 2002) using the Gateway system (Invitrogen).

Quantitative RT-PCR Analysis

Gene expression was analyzed by quantitative PCR using the iQ SYBR-Green (Bio Rad). An *L. minor* α-Tubulin gene was used as a standard control. Primers were tested to ensure equivalent values of PCR efficiency. The threshold cycle (Ct) values of PCR reactions were obtained from three independent biological replicates with three technical replicates each. The relative quantification of expression levels was performed using the comparative Ct method (Livak and Schmittgen, 2001).

RT-PCR Detection of microRNAs

RT-PCR analyses of miRNAs and amiRNAs was carried out as described (Varkonyi-Gasic et al., 2007).

Chlorophyll Quantification

Chlorophyll was extracted in ethanol and quantified by spectrophotometry (Ritchie, 2006) using three biological replicates.

5'-RACE PCR

The RACE PCR was performed using a standard protocol for non-capped RNA. 2-5 μg of total RNA were used for the 5'RACE adapter ligation reaction (T4 RNA ligase 5 U/μl from Ambion). After the ligation an RT PCR was performed using SuperScript® III First-Strand Synthesis SuperMix (Invitrogen™) following the manufacturer indications. Two rounds of nested PCRs were performed using Taq DNA polymerase (NEB). The bands obtained were gel extracted (QIAquick Gel Extraction Kit—QIAGEN®), cloned using TOPO® TA Cloning Kit (INVITROGEN™) and transformed into ONESHOT® TOP10 Competent Cells (INVITROGEN™) following the manufacturer indications. White colonies were selected for amplification in liquid medium and plasmid was extracted using the QIAprep Spin Miniprep Kit (QIAGEN®). Plasmid DNA was sequenced using a gene specific primer.

TABLE 2

Oligonucleotides

| Name | Sequence |
| --- | --- |
| SB3-4 | CTTCTCATTATCGGTGGTGAAC (SEQ ID NO: 1) |
| SB3-2 | CTCTCTAACCATCTGTGGGTC (SEQ ID NO: 2) |
| SB3-1 | CTGGAGATTATTACTCGGGTAGATC (SEQ ID NO: 3) |
| SB5-1 | ATGATTAGAGTCCCGCAATTATAC (SEQ ID NO: 4) |
| SB5-2 | GCAAACTAGGATAAATTATCGCGC (SEQ ID NO: 5) |
| SB5-4 | GTTACTAGATCGACCGGCATG (SEQ ID NO: 6) |
| SSU5A Fw | CAATCGCCAGAAATGTCAGA (SEQ ID NO: 7) |
| SSU5A Rv | GCCTCCCTCTCTCTTCCTCT (SEQ ID NO: 8) |
| SSU5B Fw | TTTGAGCCAGTTTAGGGTGC (SEQ ID NO: 9) |
| SSU5B Rv | CGCGCTTTCCCTCTTTCTCT (SEQ ID NO: 10) |
| 0748 Fw | GAGAGATAAGCCAAAGACGAGA (SEQ ID NO: 11) |
| 0748 Rv | CGTTGTGGAGAATTGAAGAGC (SEQ ID NO: 12) |
| 0450 Fw | ATGTAGGGGGATGGAAGGAG (SEQ ID NO: 13) |
| 0450 Rv | TCGCTCTAGGAAACCAAAACA (SEQ ID NO: 14) |
| 0631 Fw | CCGGTAGAGCGAGAGAAGAA (SEQ ID NO: 15) |
| 0631 Rv | GATCGTCGGCGAGAAGAA (SEQ ID NO: 16) |

TABLE 1

Different plasmids used herein

| Name | Description | Reference |
| --- | --- | --- |
| pB7WG2D | Over expression together with a visible marker (GFP) in a different cassette | (Karimi at al., 2002) |
| pB7FWG,0 | Promoter study with a visible marker (GFP) | (Hajdukiewicz et al., 1994) |
| pENTR221 | Gateway ® type (lambda att-type) recombinational cloning entry (master) vector | Invitrogen ™ |
| pOXAC1 | CaMV 35S promoter inserted in a pB7FWG,0 backbone | This work |
| pOXAC2 | *Zea mays* UBI promoter inserted in a pB7FWG,0 backbone | This work |
| pOXAC3 | *Lemna gibba* ACT promoter inserted in a pB7FWG,0 backbone | This work |
| pOXAC4 | *Lemna gibba* SSU5A promoter inserted in a pB7FWG,0 backbone | This work |
| pOXAC5 | *Lemna gibba* SSU5B promoter inserted in a pB7FWG,0 backbone | This work |
| pMRAC1 | lmn_m0450 precursor inserted in a pB7WG2D backbone | This work |
| pMRAC2 | lmn_m0631 precursor inserted in a pB7WG2D backbone | This work |
| pMRAC3 | lmn_m0697 precursor inserted in a pB7WG2D backbone | This work |
| pMRAC4 | lmn_m0748 precursor inserted in a pB7WG2D backbone | This work |
| pARAC1 | amiRNA_LgPDS precursor inserted in a pB7WG2D backbone | This work |

TABLE 2-continued

Oligonucleotides

| Name | Sequence |
|---|---|
| 0697 Fw | TCTACATGCTAAGAGGGTGGTG (SEQ ID NO: 17) |
| 0697 Rv | TCCCATTGAGACGAAGAAGG (SEQ ID NO: 18) |
| miR166 | GGGGAATGAAGCCTGGTCCGA (SEQ ID NO: 19) |
| eGFP 5'Rv | GAACTTGTGGCCGTTTACGT (SEQ ID NO: 20) |
| 35S 3'Fw | GCTCCTACAAATGCCATCA (SEQ ID NO: 21) |
| miR319 | AGGGAGCTCCCTTCAGTCCAA (SEQ ID NO: 22) |
| 35S Fw | ACTAGAGCCAAGCTGATCTC (SEQ ID NO: 23) |
| 35S Rv | TTGTGATATCACTAGTGCGG (SEQ ID NO: 24) |
| ZmUBIp Fw | GACCCGGTCGTGCCCCTCT (SEQ ID NO: 25) |
| ZmUBIp Rv | GTAACACCAAACAACAGGGT (SEQ ID NO: 26) |
| LgACTp Fw | TATTTAATATATGTTTGCGAT (SEQ ID NO: 27) |
| LgATCp Rv | TGTGCGCAGTTCTGCAAAGA (SEQ ID NO: 28) |
| AD1 | NTCGASTWTSGWGTT (SEQ ID NO: 29) |
| AD2 | NGTCGASWGANAWGAA (SEQ ID NO: 30) |
| AD4 | STTGNTASTNCTNTGC (SEQ ID NO: 31) |
| M13 Fw | GTTTTCCCAGTCACGAC (SEQ ID NO: 32) |
| M13 Rv | AACAGCTATGACCATG (SEQ ID NO: 33) |

Kits, Chemicals, Buffers and Enzymes

TABLE 3

Kits and enzymes

| Name | Company |
|---|---|
| QIAprep ® Spin Miniprep Kit | QIAGEN ® |
| OneTaq ™ DNA Polymerase | New England Biolabs ® Inc. |
| Gateway ® BP Clonase ™ | Invitrogen ™ by Life Technologies ™ |
| Gateway ® LR Clonase ™ | Invitrogen ™ by Life Technologies ™ |
| SuperScript ® III First-Strand Synthesis | Invitrogen ™ by Life Technologies ™ |
| Phusion ® High-Fidelity DNA Polymerase | New England Biolabs ® Inc. |
| Different restriction enzymes | New England Biolabs ® Inc. |
| T4 Polynucleotide Kinase | New England Biolabs ® Inc. |
| QUIAquick ® PCR Purification Kit | QIAGEN ® |
| MinElute ® Gel Extraction Kit | QIAGEN ® |
| DNA Clean and Concentrator ™ | ZYMO RESEARCH Corp. |
| Direct-zol ™ RNA MiniPrep | ZYMO RESEARCH Corp. |

TABLE 4

Additional reagents and markers

| Name | Company |
|---|---|
| 6X Loading Dye Solution | Thermo Fisher Scientific Inc. |
| GeneRuler ™ 1 kb DNA Ladder | Thermo Fisher Scientific Inc. |
| UltraPure ™ Distilled Water | Invitrogen ™ by Life Technologies ™ |

TABLE 4-continued

Additional reagents and markers

| Name | Company |
|---|---|
| 200 Proof Ethyl Alcohol ACS/USP Grade | Ultra Pure, LLC. |
| Ethidium Bromide | Sigma-Aldrich ® |
| Paraformaldehyde | Sigma-Aldrich ® |
| Triton ™ X-100 | Sigma-Aldrich ® |
| iQ ™ SYBR Green | BioRad ® |
| ATP, [γ-32P]-3000 Ci/mmol 5 mCi/ml | Perkin Elmer ® |
| GeneMate LE Agarose | BioExpress ® |
| 4',6-diamidino-2-phenylindole (DAPI) dihydrochloride | Sigma-Aldrich ® |
| Sodium dodecyl sulfate (SDS) | Sigma-Aldrich ® |
| 40% (19:1) Acryl:BisAcryl | BioRad ® |
| Urea | BioRad ® |
| Tetramethylethylenediamine (TEMED) | Sigma-Aldrich ® |
| Ammonium persulfate (APS) | Sigma-Aldrich ® |
| GeneScreen Plus ® Hybridization Transfer Membrane | Perkin Elmer ® |
| Ambion ®ULTRAhyb ®-Oligo | Invitrogen ™ by Life Technologies ™ |
| Ambion ® RNA Gel Loading Dye II | Invitrogen ™ by Life Technologies ™ |
| Ambion ® RNaseZap ® | Invitrogen ™ by Life Technologies ™ |

TABLE 5

Chemicals for biological cultures

| Name | Stock concentration | Company |
|---|---|---|
| Cefotaxamin | 500 mg/mL (H2O) | Gold Biotechnology ® |
| Carbenicillin | 200 mg/mL (H2O) | Gold Biotechnology ® |
| Kanamiyin | 50 mg/mL (H2O) | Gold Biotechnology ® |
| Ampicyllin | 100 mg/mL (H2O) | Gold Biotechnology ® |
| Rifampicin | 100 mg/mL (DMSO) | Gold Biotechnology ® |
| Gentamicin | 50 mg/mL (H2O) | Gold Biotechnology ® |
| Acetosyringone | 100 mM (EtOH) | Sigma-Aldrich ® |
| Spectinomycin | 100 mg/mL (H2O) | Gold Biotechnology ® |
| Streptinomycin | 50 mg/mL (H2O) | Gold Biotechnology ® |
| 2,4-Dichlorophe-noxyacetic acid(2,4-D) | 10 mM (H2O) | Sigma-Aldrich ® |
| Thidiazuron (TDZ) | 5 mM (EtOH) | Sigma-Aldrich ® |
| 6-Benzylaminopurine (BAP) | 20 mM (H2O) | Sigma-Aldrich ® |
| DL-Phosphinothricin (PPT) | 10 mg/mL (H2O) | Gold Biotechnology ® |
| Glycerol solution | 50% v/v (H2O) | Sigma-Aldrich ® |

TABLE 6

Buffers and their composition at use concentration

| Name | Composition |
|---|---|
| Tris-acetate-EDTA (TAE) | 40 mM Tris-Acetate, 0.1 mM EDTA |
| Tris/Borate/EDTA (TBE) | 89 mM Tris Base, 89 mM Boric Acid, 2 mM EDTA |
| Phosphate Buffered Saline (PBS) | 138 mM NaCl, 2.7 mM KCl, 10 mM Na2HPO4, 2 mM KH2PO4 |
| Saline-Sodium Citrate (SSC) 2X | 0.03M sodium citrate, pH approx. 7.0, containing 0.3M NaCl |
| Tris-HCl 1M | 1M Trizma ® Base, adjust pH 7.6 with 1M HCl |
| Extraction Buffer (1 L) | 63.77 gr Sorbitol, 12.1 gr Trizma ® Base, 1.69 gr EDTA, adjust pH 7.5 with 1M HCl |
| Sarkosyl | 5% of N-lauryl Sarcosine |
| Nuclei Lysis Buffer (1 L) | 200 mL Tris 1M pH 7.5, 200 mL EDTA 0.25M, 400 mL NaCl 5M, 20 gr Hexadecyl-trimethil-ammonium bromide (CTAB) |

TABLE 7

Consumables

| Name | Company |
|---|---|
| Rattle Platting Beads (5 mm) Sterile | ZYMO RESEARCH Corp. |
| 1 mL/20 mL Syringe | Becton Dickinson ® |
| 20 G × 1 ½ inch Needle | Becton Dickinson ® |
| 75 cm² Cell Culture Flask, 250 ml, tissue-culture treated polystyrene, canted neck, vented cap | Becton Dickinson ® |
| 15 mL/50 mL Falcon Tubes | Becton Dickinson ® |
| 6 well/24 well Corning ® Costar ® cell culture plates | Sigma-Aldrich ® |
| ProbeOn ™ Plus Microscope Slides | Fisher scientific ® |
| BioExcell ® 0.2 mL Thin Wall PCR tubes | WW Medical Products Inc. |
| 1.7 mL Microtubes | WW Medical Products Inc. |
| BioExcell ® Pipet tips | WW Medical Products Inc. |
| 10 mL/25 mL Serological Pipettes | Fisher scientific ® |

TABLE 8

Equipment

| Name | Company |
|---|---|
| Nikon Zoom Stereomicroscope SMZ 1500 | Nikon ® |
| Zeiss LSM 710 Confocal Microscope Carl | Zeiss ® |
| NanoDrop ND-1000 Spectrophotometer | Thermo Scientific ® |
| DNA Engine Tetrad ® 2 Peltier Thermal Cycler | BioRad ® |
| Trans-Blot ® SD Semi-Dry Transfer Cell | BioRad ® |
| CL-1000 Crosslinker | UVP, LLC |
| CFX96 ® Real Time System | BioRad ® |
| FLA-5100 Fluorescent Image Analyzer | FujiFilm ® |
| Imaging Plate BAS-MS2040 | FujiFilm ® |

TABLE 8-continued

Equipment

| Name | Company |
|---|---|
| Environ-Shaker Chamber | Lab-Line Instrument Inc. |
| QIAxcel Advanced | QIAGEN ® |
| Genesys 20 Spectrophotometer | Thermo Scientific ® |
| Centrifuges 5417C/5810R | Eppendorf ® |
| Leica VT1000 S Vibrating Blade Microtome | Leica ® |
| HB-1000 Hybridizer | UVP, LLC |
| I 26 Incubator Shaker | New Brunswick Scientific ® |
| Molecular Imager ® Gel Doc ™ XR | BioRad ® |
| AR-41L3 Arabidopsis chamber | Percival Scientific Inc. |

TABLE 9

Reaction mix composition for different Tail-PCR stages

| Reagent | 1st Amplification | 2nd Amplification | 3rd Amplification |
|---|---|---|---|
| 10x OneTaq ™ Buffer | 2 μL | 2 μL | 3 μL |
| dNTPs (2 mM) | 2 μL | 2 μL | 3 μL |
| AD1/AD2/AD4 (20 μM) | 3 μL | 2 μL | 3 μL |
| T-DNA primer (20 μM) | 2 μL (SB3-1/SB5-1) | 2 μL (SB3-2/SB5-2) | 3 μL (SB3-4/SB5-4) |
| OneTaq ™ Polymerase | 0.2 μL | 0.2 μL | 0.3 μL |
| dH2O | 11 μL | 12 μL | 18 μL |
| Template | 1 μL of Genomic DNA | 1 μL of a 1:50 dilution of 1st amplification | 1.5 μL of a 1:10 dilution of 2nd amplification |
| Total | 21.2 μL | 21.2 μL | 31.8 μL |

TABLE 10

Reaction programs for different Tail-PCR stages

| 1st Amplification | 2nd Amplification | 3rd Amplification |
|---|---|---|
| 1. 94° C. for 1 min | 1. 94° C. for 10 sec | 1. 94° C. for 15 sec |
| 2. 94° C. for 10 sec | 2. 64° C. for 1 min | 2. 44° C. for 1 min |
| 3. 62° C. for 1 min | 3. 72° C. for 2:30 min | 3. 72° C. for 2:30 min |
| 4. 72° C. for 2:30 min | 4. 94° C. for 10 sec | 4. Go to Step 1, 19 times |
| 5. Go to Step 2, 4 times | 5. 64° C. for 1 min | 5. 72° C. for 5 min |
| 6. 94° C. for 10 sec | 6. 72° C. for 2:30 min | 6. 4° C. Forever |
| 7. 25° C. for 3 min | 7. 94° C. for 10 sec | |
| 8. 0.2° C./s to 72° C. | 8. 44° C. for 1 min | |

TABLE 10-continued

Reaction programs for different Tail-PCR stages

| 1st Amplification | 2nd Amplification | 3rd Amplification |
|---|---|---|
| 9. 72° C. for 2:30 min | 9. 72° C. for 2:30 min | |
| 10. 94° C. for 10 sec | 10. Go to Step 1, 11 times | |
| 11. 68° C. for 1 min | 11. 72° C. for 5 min | |
| 12. 72° C. for 2:30 min | 12. 4° C. Forever | |
| 13. 94° C. for 10 sec | | |
| 14. 68° C. for 1 min | | |
| 15. 72° C. for 2:30 min | | |
| 16. 94° C. for 10 sec | | |
| 17. 44° C. for 1 min | | |
| 18. 72° C. for 2:30 min | | |
| 19. Go to Step 10, 14 times | | |
| 20. 72° C. for 5 min | | |
| 21. 4° C. Forever | | |

Additional Sequences

The sequencing results for each endogenous promoter and microRNA precursor isolated described herein are presented below.

Lg ACTp
SEQ ID NO: 34
TATTTAATATATGTTTGCGATTTTATTTATTTGTTTTAATAGAATTATTT

GAGTCCTTAATTATTTAAGTGGGAAGACGTTTTTTCTTGTAGTAGAAAAT

TGAAATTTGGTTTTCTAGAAATTTGTATTGTATTGGTGTTCCATTTCACT

CGGTGACAGCTCGCTTATGCTCACGCATAAGACATAAGCTACGTGGAGAT

CGTGGGTTGTTTTTTCCAGCGAACTTTTTCGCTCGATCCATGGAAAATAT

CAAAATATACAACATATTTGCAGGAAATTGCATGATCATCAACAGTGTTA

AATTCTTTTTCTTCTGTTTACAATTTGTTTTAAAGTAAAAACAAAACTAT

TTTTATCATCCGGAAACGAGAAAATAAAAGATAGTGAATTTCTTCGGTTT

TTCAACTTCTTATATAAATAATTTAAATATTCACGTGAGAATGGATGACC

CGGTCCATTGACCGACCAATGGGTTGAGTCAGCAAAGGGGAAAAATATGG

GCCTCATATTTGACACGGCTCTCTCTCTCTCTCTCTCTCTCTCTCTCTCT

CTCTCTCTCCCTCTCTCTCTCTCTCTCTCTCTCTCTCTCTCTCTCTCTCT

CTCTCTCTCAGTCTCACTCCCCATCATCTCTCCTCTCACAAACAGGTCTA

TCTGTCTATCTCTCCTCCGCCAGCCACAGGTCTGAATGAATTAGCTTT

AAATTTTGAGAAGGGAGTGAGTGGTTGTGTAGCCACCTCATTTGACCACT

ACCATGAGACTTTATGTAGAATAAAATTAGTTTTATTTTTTAATATAATT

ATTCCGTTTCCATTTAGGATTTAGAATAAAAGTGGGAGGGGTTTATTTAT

TGGAGAATATTGTAATTTGTTATTTTTGGAGTGAATGGAAGTTTCATTTG

TGTTTCATTTGTGTTTCATTTCGTGCGGTGACAGCTCGCTTATGCTGACG

CATCCTAGCTTTAAAAGGAAAGGCTGAGCCAGCGGCTGCTTTGTTGGACG

CCCTCAGACCGCTGCTCTTCTTCCACGCTACTTTTCTTCCGGCGGAGAAG

AGGTAAAGCTCGACCGCGGCATCCTCGGAATCTCGGAGAGCAGGTAGAGA

TCTATGCTGGTTTTCTCATAGATCGGTCTTCTCGAAACCTGTAAAATCTT

CTGATTGCTTGTCTGATACCATTTTCTTCCCGATCGTAGCATTTCGCATG

CTGTTTATTCGTGTTTTTTGTTTTCTCGGCTTGCAATCTTTGAGATGTTC

AGATCTTATGTCTTCTCGTGTCGCATCTTGTAGATCTGGTTTCTTTTTGT

GCGCCGATCTGTTCACTCGATCCTCTTTTCTCGTCAATCGCCAGCGATCT

TTATTAACTTGTTCTCCGAGGAGGATTCCCTGCTTTCCATGGCGATTATC

AACATCTCGGGTGCTTGCGTGAAGTTCTTTTTCTGATTTCCCGTTGTAGA

ACATAAGTTACCATTTCTTTCATTATCTGTATTTTTCTTTCGTATCAGAT

GCATTTCCTCTACTGTTTCTGCTGCTTTCTGTACTTCTCCGATTGGAGGC

TCGATTTCCTGATATTTGGAGACAACTACAGGAAGCATTACGTATTTCCA

ACTGTAGATTAACATTTCTTTTTGGTTCATCGATCTGTCATCCTCATTTT

TCATCATTTTTCGTGGAAAGTACTAAAAGATTAACTGGTCTAGGTCCTGG

CGAATAACTGTGATGGAAAAAATGACATTACTAATATAATTTAACCTAAT

TTCGTTGACACGATCATTTATGGTTTTTTATTTAAACAAATACTACGAGA

CTTCGGAGTCTATATTGTCATTTTTTTATATGGGAGGTAAACTGGTCAAT

TTCCAGTTTCTTTTGTCATGTCTTCTATCTAAATATGTAACATCTATCGG

AATTATTCCCCTGAATTATCATCCCTTTCTACTTATCTTAATTTCATTTT

CTGTCCTCTCTAGCTATCTTAATTAACTCATCTTTGCAGAACTGCGCACA

Lg SSU5Ap
SEQ ID NO: 35
CAATCGCCAGAAATGTCAGAAGAGGCTGGCCTCTAGAGGCCCCGCAAGGC

CTCACCCAGAGTTGGCGCAGCCTCGCCGCGTCCGAGGCATGTGCAGCTCA

CTAAACGGGAAATTTCCAACAGTCAACCCGCAGACAAGGGCCAAACCCCA

AAGAACAATTCTTTGTCCATGAAGTAAAATAACGTTTTATCTTGAAACAA

GAGTTCAAGGCCAAATGTGGCCAAGCGATTCGGATGGGGGGCATGAACA

CCTTGCAATCATTTCCTGACTCATTTCTGAACAGTGCCCTTGGCACACGT

GTAGACCTGCCAACATAATTAAAATATAATATTAGAAAAAAAATCTCCCA

TAGTATTTAGTATTTACCAAAAGTCACACGACCACTAGACTTCCAATTTA

CCCAAATCACTAACCAATTTTAGGTTGAATGGAAAATAGAACGCAATAAT

GTCCGACATATTTCCTATATTTCCGTTTTTCGAGAGAAGGCCTGTCGATA

AGGATGTAATCCATGGGCGACGCAGTGTGTGGAGGAGCAGGCTCAGTCT

CCTTCTCGTGAGGGATCGAACGATGGCAGCCGTAGAATGCTCAGAGCAAT

GACCCAGCCAGCTGTGGGACCTATTTAAGCGGGTTATGACGAGTCTCAG

ACTCGCAAGTGGAGAGAGGATCCGAGCGTCCAGTGAGAGGAAGAGAGAGG

GAGGC

Lg SSU5Bp
SEQ ID NO: 36
TTAGGGTGCAAAATAATTACACATCCTAAGAATTATTTATCTACAATTTA

GCTCCGGACAAAATTAGTTCATTATTCAATCACTTTAATGTTTTCAATGG

CCACAAAATGTTTTGATCCAGATGCACTTTTGATTCAGTCACCCTAGATG

CACTTTTTGATCCCCGGCAAAACTTTAGGACTAGTGTCCGTTCACTCACC

TTCTAATAATCTGTGTGACGAAAATATAAAGAAAAACAGTGACAATTATC

CTATTTGAACAAGACCTGAGTTGCTCGTTTTACTCACTAGATATGCCACT

AAAAAGGTGAGAATAGTTTTCTTACTACTTTGGCATTTGCCACCTAATTT

```
                        -continued
CAGTGTCAGAGTCGACTAGCCTTCCATTCCTTGTAAATCAATGAAAATTT

GATGAAAACTAAGAACCTTCAATAAGCGACAAATCGCTTCGTTTCTCCTT

TGCGGATAGATGGCAGACGATAAGAATGTAATCCAGAAGATGAGGCCATT

GTGGAGGAGAAGATGCAGTGTCCCCCTCTGTAGAGATCGAACAATGGCAG

CCATAGAATCCCCGGAGCACTGAGACAGGGACAGACGCCAATTTAAGTGG

CCCGAGAACGGTTTTAGAAACTCCCGAGGTGAGCAAGGATCCGGATCGAG

CGCGAAGAAGAGA

Imn-0450
                                          SEQ ID NO: 37
TTACTGTTGAGGGGAATGCTGTCTGGCTCGAGGTCACCGTTCTCTTCTTC
TCAATCTCCTACTTCCATCTATCTGAATGGAGAAGGGAATGGAAGGAGAG
ATCTGCCTCGGACCAGGCTTCATTCCCCCCAATCAAAG

Imn-0631
                                          SEQ ID NO: 38
CCGTTGGGAAGCTTTTCCTTTGAGGGGAATGTTGTCTGGCTCGAGGTTTC
TCCTTTTCTCTCTGGAGAAATTGCGATGGAGAGGAGAGAATGCCCTCGGA
CCAGGCTTCATTCCCCTCAATCGCAGCTTCCACAAACCTTC

Imn-0697
                                          SEQ ID NO: 39
GTCGCATGTTGAGGCTGGCTTGTGGGGAATGTTGTCTGGCCTGAGGTCAA
GCAATGGAGATATTGTGGGTATAAGGTCTCTAGATCTCGGACCAGGCTTC
ATTCCCCTCAGCCGGCATCCACATTTTCTCTC

Imn-0748
                                          SEQ ID NO: 40
GCTTCGTCGGTGATATGGGAGGAAGAGAGCTTCCTTCTGTCCACTCTCTG

GTGGCCGCAGGACTACGCCATCTGCCGACTCATTCATCCAAATCCCAAGC

CGCGGAGGATTTTCAGGTTTGGGAGATGCGTGAATGGCGCGGGAGATAGC

CCGGGTTCTGCGCCGGCTGTGTTTGGACTGAAGGGAGCTCCCTCTTCTTC

ATCTCTCTCTCTCTACCG

The sequence of an artificial microRNA precursor
designed and synthesize herein.
pre-amiPDS
                                          SEQ ID NO: 41
GGGGACAAGTTTGTACAAAAAAGCAGGCTGCCCGTTGGGAAGCTTTTCCT

TTGACAGTTCATTGCTACATCTTAAGGTTTCTCCTTTCTCTCTGGAGA

AATTGCGATGGAGAGGAGAGAATGCCCTTAGAATGTAGGTATGAACTGTC

AATCGCAGCTTCCACAAACCTTCTACCCAGCTTTCTTGTACAAAGTGGTC

C
```

REFERENCES

ALVAREZ, J. P., PEKKER, I., GOLDSHMIDT, A., BLUM, E., AMSELLEM, Z., and ESHED, Y. (2006). Endogenous and synthetic microRNAs stimulate simultaneous, efficient, and localized regulation of multiple targets in diverse species. *The Plant Cell Online* 18, 1134-1151.

ANDERSSON, D. I. 2006. The biological cost of mutational antibiotic resistance: any practical conclusions? *Current opinion in microbiology*, 9, 461-465.

ANDRIANOV, V., BORISJUK, N., POGREBNYAK, N., BRINKER, A., DIXON, J., SPITSIN, S., FLYNN, J., MATYSZCZUK, P., ANDRYSZAK, K. & LAURELLI, M. 2010. Tobacco as a production platform for biofuel: overexpression of *Arabidopsis* DGAT and LEC2 genes increases accumulation and shifts the composition of lipids in green biomass. *Plant biotechnology journal*, 8, 277-287.

APCHELIMOV, A., SOLDATOVA, O., EZHOVA, T., GRIMM, B., and SHESTAKOV, S. (2007). The analysis of the ChlI 1 and ChlI 2 genes using acifluorfen-resistant mutant of *Arabidopsis thaliana*. *Planta* 225, 935-943.

AXTELL, M. J., SNYDER, J. A. & BARTEL, D. P. 2007. Common functions for diverse small RNAs of land plants. *The Plant Cell Online*, 19, 1750-1769.

BAO, X. & OHLROGGE, J. 1999. Supply of fatty acid is one limiting factor in the accumulation of triacylglycerol in developing embryos. *Plant physiology*, 120, 1057-1062.

BAUD, S., WUILLEME, S., TO, A., ROCHAT, C. & LEPINIEC, L. 2009. Role of WRINKLED1 in the transcriptional regulation of glycolytic and fatty acid biosynthetic genes in *Arabidopsis*. *The Plant Journal*, 60, 933-947.

BRAIN, R. A. & SOLOMON, K. R. 2007. A protocol for conducting 7-day daily renewal tests with *Lemna gibba*. *Nature protocols*, 2, 979-987.

BROWN, C., BROOKS, F. J., PEARSON, D. & MATHIAS, R. J. 1989. Control of embryogenesis and organogenesis in immature wheat embryo callus using increased medium osmolarity and abscisic acid. *Journal of Plant Physiology*, 133, 727-733.

BUZBY, J. S., YAMADA, T. & TOBIN, E. M. 1990. A light-regulated DNA-binding activity interacts with a conserved region of a *Lemna gibba* rbcS promoter. *The Plant Cell Online*, 2, 805-14.

CASES, S., SMITH, S. J., ZHENG, Y. W., MYERS, H. M., LEAR, S. R., SANDE, E., NOVAK, S., COLLINS, C., WELCH, C. B. & LUSIS, A. J. 1998. Identification of a gene encoding an acyl CoA: diacylglycerol acyltransferase, a key enzyme in triacylglycerol synthesis. *Proceedings of the National Academy of Sciences*, 95, 13018-13023.

CASTEL, S. E. & MARTIENSSEN, R. A. 2013. RNA interference in the nucleus: roles for small RNAs in transcription, epigenetics and beyond. *Nature Reviews Genetics*, 14, 100-112.

CHHABRA, G., CHAUDHARY, D, SAINGER, M. and JAIWAL, P. K. 2001. Genetic transformation of Indian isolate of *Lemna minor* mediated by *Agrobacterium tumefaciens* and recovery of transgenic plants. *Physiol. Mol. Biol. Plants*, 17(2), 129-136.

CIA 2013. *The World Factbook*, Directorate of Intelligence.

COX, K. M., STERLING, J. D., REGAN, J. T., GASDASKA, J. R., FRANTZ, K. K., PEELE, C. G., BLACK, A., PASSMORE, D., MOLDOVAN-LOOMIS, C. & SRINIVASAN, M. 2006. Glycan optimization of a human monoclonal antibody in the aquatic plant *Lemna minor*. *Nature biotechnology*, 24, 1591-1597.

CHENG, J. J. & STOMP, A. M. 2009. Growing duckweed to recover nutrients from wastewaters and for production of fuel ethanol and animal feed. Clean—Soil, Air, Water, 37, 17-26.

CHISTI, Y. 2008. Biodiesel from microalgae beats bioethanol. Trends in biotechnology, 26, 126-131, DEHESH, K., TAI, H., EDWARDS, P., BYRNE, J. & JAWORSKI, J. G. 2001. Overexpression of 3-ketoacyl-acyl-carrier protein synthase Ills in plants reduces the rate of lipid synthesis. *Plant Physiology*, 125, 1103-1114.

DURRETT, T. P., BENNING, C. & OHLROGGE, J. 2008. Plant triacylglycerols as feedstocks for the production of biofuels. *The Plant Journal*, 54, 593-607.

ERNST, E & MARTIENSSEN, R A. 2012. Available: lemna.org.

FARGIONE, J., HILL, J., TILMAN, D., POLASKY, S. & HAWTHORNE, P. 2008. Land clearing and the biofuel carbon debt. *Science*, 319, 1235-1238.

FARRELL, A. E., PLEVIN, R. J., TURNER, B. T., JONES, A. D., O'HARE, M. & KAMMEN, D. M. 2006. Ethanol can contribute to energy and environmental goals. *Science*, 311, 506-508.

FELIPPES, F. F., OTT, F., and WEIGEL, D. (2011). Comparative analysis of non-autonomous effects of tasiRNAs and miRNAs in *Arabidopsis thaliana*. *Nucleic acids research* 39, 2880-2889.

FELIPPES, F. F., and WEIGEL, D. (2009). Triggering the formation of tasiRNAs in *Arabidopsis thaliana*: the role of microRNA miR173. *EMBO reports* 10, 264-270.

FIRE, A., XU, S. Q., MONTGOMERY, M. K., KOSTAS, S. A., DRIVER, S. E. & MELLO, C. C. 1998. Potent and specific genetic interference by double-stranded RNA in *Caenorhabditis elegans*. *nature*, 391, 806-811.

HAJDUKIEWICZ, P., SVAB, Z. & MALIGA, P. 1994. The small, versatile pPZP family of *Agrobacterium* binary vectors for plant transformation. *Plant Molecular Biology*, 25, 989-994.

HAMILTON, A. J. & BAULCOMBE, D. C. 1999. A Species of Small Antisense RNA in Posttranscriptional Gene Silencing in Plants. *Science*, 286, 950-952.

HANNON, G. J. 2002. RNA interference. *nature*, 418, 244-251.

HANSEN, G. & WRIGHT, M. S. 1999. Recent advances in the transformation of plants. *Trends in Plant Science*, 4, 226-231.

HILL, J., NELSON, E., TILMAN, D., POLASKY, S. & TIFFANY, D. 2006. Environmental, economic, and energetic costs and benefits of biodiesel and ethanol biofuels. *Proceedings of the National Academy of Sciences*, 103, 11206-11210, HILLMAN, W. S. 1961. The *Lemnaceae*, or duckweeds. *The Botanical Review*, 27, 221-287.

HILLMAN, W. S. 1966. Photoperiodism in *Lemna*: Reversal of Night Interruption Depends on Color of the Main Photoperiod. *Science*, 154, 1360-2.

HU, Q., SOMMERFELD, M., JARVIS, E., GHIRARDI, M., POSEWITZ, M., SEIBERT, M. & DARZINS, A. 2008. Microalgal triacylglycerols as feedstocks for biofuel production: perspectives and advances. *The Plant Journal*, 54, 621-639.

JACKSON, A. L., BARTZ, S. R., SCHELTER, J., KOBAYASHI, S. V, BURCHARD, J., MAO, M., LI, B., CAVET, G. & LINSLEY, P. S. 2003. Expression profiling reveals off-target gene regulation by RNAi. *Nature biotechnology*, 21, 635-637.

JACKSON, M. A., ANDERSON, D. J. & BIRCH, R. G. 2013. Comparison of *Agrobacterium* and particle bombardment using whole plasmid or minimal cassette for production of high-expressing, low-copy transgenic plants. *Transgenic Research*, 22, 143-151.

JAIN, R. K., JAIN, S. & WU, R. 1996. Stimulatory effect of water stress on plant regeneration in aromatic indica rice varieties. *Plant Cell Reports*, 15, 449-454.

JOSHI, T., YAN, Z., LIBAULT, M., JEONG, D. H., PARK, S., GREEN, P. J., SHERRIER, D. J., FARMER, A., MAY, G., MEYERS, B. C., XU, D. & STACEY, G. 2010. Prediction of novel miRNAs and associated target genes in *Glycine max*. *BMC Bioinformatics*, 11, S14.

JUNG, J. H. & PARK, C. M. 2007. MIR166/165 genes exhibit dynamic expression patterns in regulating shoot apical meristem and floral development in *Arabidopsis*. *Planta*, 225, 1327-1338.

KARIMI, M., INZE, D. & DEPICKER, A. 2002. GATEWAY'm vectors for *Agrobacterium*-mediated plant transformation. *Trends in Plant Science*, 7, 193-195.

KIDNER, C. A. & MARTIENSSEN, R. A. 2004. Spatially restricted microRNA directs leaf polarity through ARGONAUTE1. *Nature*, 428, 81-84.

KONCZ, C. S., MAYERHOFER, R., KONCZ-KALMAN, Z., NAWRATH, C., REISS, B., REDEI, G. P., and SCHELL, J. (1990). Isolation of a gene encoding a novel chloroplast protein by T-DNA tagging in *Arabidopsis thaliana*. *The EMBO journal* 9, 1337.

LANDESMAN, L., PARKER, N. C., FEDLER, C. B. & KONIKOFF, M. 2005. Modeling duckweed growth in wastewater treatment systems. *Livestock Research for Rural Development*, 17.

LANDOLT, E. 1986. Biosystematic investigations in the family of duckweeds (*Lemnaceae*)(vol. 2.) Veroff, *Geobot, Inst., Rubel*, 1, 566p.

LANDOLT, E. & KANDELER, R. 1987. Biosystematic investigations in the family of duckweeds (*Lemnaceae*), Vol. 4: The family of *Lemnaceae*-a monographic study, Vol. 2 (phytochemistry, physiology, application, bibliography). *Veroeffentlichungen des Geobotanischen Instituts der ETH, Stiftung Ruebet*

LES, D. H., CRAWFORD, D. J., LANDOLT, E., GABEL, J. D. & KIMBALL, R. T. 2002 Phylogeny and systematics of *Lemnaceae*, the duckweed family. *Systematic Botany*, 27, 221-240.

LI, J., JAIN, M., VUNSH, R., VISHNEVETSKY, J., HANANIA, U., FLAISHMAN, M., PERL, A. & EDELMAN, M. 2004. Callus induction and regeneration in *Spirodela* and *Lemna*. *Plant Cell Rep*, 22, 457-64.

LIU, J., HUA, W., ZHAN, G., WEI, F., WANG, X., LIU, G. & WANG, H. 2010. Increasing seed mass and oil content in transgenic *Arabidopsis* by the overexpression of wril-like gene from *Brassica napus*. *Plant Physiology and Biochemistry*, 48, 9-15.

LIU, Y. G., MITSUKAWA, N., OOSUMI, T. & WHITTIER, R. F. 1995. Efficient isolation and mapping of *Arabidopsis thaliana* T-DNA insert junctions by thermal asymmetric interlaced PCR. *The Plant Journal*, 8, 457-463.

LIVAK, K. J., and SCHMITTGEN, T. D. (2001). Analysis of Relative Gene Expression Data Using Real-Time Quantitative PCR and the $2^{(-\Delta\Delta CT)}$. Method. *Methods* 25, 402-408.

MANSFIELD, J., GENIN, S., MAGORI, S., CITOVSKY, V., SRIARIYANUM, M., RONALD, P., DOW, M. A. X., VERDIER, V., BEER, S. V., MACHADO, M. A., TOTH, I. A. N., SALMOND, G. & FOSTER, G. D. 2012. Top 10 plant pathogenic bacteria in molecular plant pathology. *Molecular Plant Pathology*, 13, 614-629.

MATA, M., MARTINS, A. A. & CAETANO, N. S. 2010. Microalgae for biodiesel production and other applications: a review. *Renewable and Sustainable Energy Reviews*, 14, 217-232.

MEYERS, B. C., AXTELL, M. J., BARTEL, B., BARTEL, D. P., BAULCOMBE, D. C., BOWMAN, J. L., CAO, X., CARRINGTON, J. C., CHEN, X., GREEN, P. J., GRIFFITHS-JONES, S., JACOBSEN, S., MALLORY, A. C., MARTIENSSEN, R. A., POETHIG, R. S., 01, Y., VAUCHERET, H., VOINNET, O., WATANABE, Y., WEIGEL, D. & ZHU, J. K. 2008. Criteria for annotation of plant MicroRNAs. The Plant Cell Online, 20, 3186-3190.

MOLNAR, A., BASSETT, A., THUENEMANN, E., SCHWACH, F., KARKARE, S., OSSOWSKI, S., WEIGEL, D. & BAULCOMBE, D. C. 2009. Highly specific gene silencing by artificial microRNAs in the unicellular alga *Chlamydomonas reinhardtii*. *The Plant Journal*, 58, 165-174.

MOON, H. K. & STOMP, A, M. 1997. Effects of medium components and light on callus induction, growth, and frond regeneration in *Lemna gibba* (Duckweed). *In Vitro Cellular & Developmental Biology—Plant*, 33, 20-25.

MURRAY, M. G. & THOMPSON, W. F. 1980. Rapid isolation of high molecular weight plant DNA. *Nucleic Acids Research*, 8, 4321-4326.

NAG, A., KING, S. & JACK, T. 2009. miR319a targeting of TCP4 is critical for petal growth and development in *Arabidopsis*. *Proceedings of the National Academy of Sciences*, 106, 22534-22539.

NATH, U., CRAWFORD, B. C., CARPENTER, R. & COEN, E. 2003. Genetic control of surface curvature. *Science Signaling*, 299, 1404.

NGUYEN, L. V., COX, K. M., KE, J. S., PEELE, C. G. & DICKEY, L. F. 2012. Genetic engineering of a *Lemna* isoleucine auxotroph. *Transgenic Research*, 21, 1071-1083.

ORON, G., PORATH, D. & JANSEN, H. 1987. Performance of the duckweed species *Lemna gibba* on municipal wastewater for effluent renovation and protein production *Biotechnology and bioengineering*, 29, 258-268.

OSSOWSKI, S., SCHWAB, R. & WEIGEL, D. 2008. Gene silencing in plants using artificial microRNAs and other small RNAs. *The Plant Journal*, 53, 674-690.

OZENGIN, N. & ELMACI, A. 2007. Performance of Duckweed (*Lemna minor* L.) on different types of wastewater treatment. *Journal of Environmental Biology*, 28, 307-314.

PDXLEITNER, M., ROGERS, S. W., LACEY, S. A. & ROGERS, J. C. 2006. A role for caleosin in degradation of oil-body storage lipid during seed germination. *The Plant Journal*, 47, 917-933.

RITCHIE, R. J. (2006). Consistent sets of spectrophotometric chlorophyll equations for acetone, methanol and ethanol solvents. *Photosynthesis Research* 89, 27-41.

RIVAL, S., WISNIEWSKI, J. P., LANGLAIS, A., KAPLAN, H., FREYSSINET, G., VANCANNEYT, G., VUNSH, R., PERL, A. & EDELMAN, M. 2008. *Spirodela* (duckweed) as an alternative production system for pharmaceuticals: a case study, aprotinin. *Transgenic Research*, 17, 503-513.

ROLFE, S. A. & TOBIN, E. M. 1991. Deletion analysis of a phytochrome-regulated monocot rbcS promoter in a transient assay system. *Proceedings of the National Academy of Sciences*, 88, 2683-2686.

RYLOTT, E. L., ROGERS, C. A., GILDAY, A. D., EDGELL, T., LARSON, T. R. & GRAHAM, I. A. 2003. *Arabidopsis* mutants in short- and medium-chain acyl-CoA oxidase activities accumulate acyl-CoAs and reveal that fatty acid 13-oxidation is essential for embryo development. *Journal of Biological Chemistry*, 278, 21370-21377.

SANJAYA, DURRETT, T. P., WEISE, S. E. & BENNING, C. 2011. Increasing the energy density of vegetative tissues by diverting carbon from starch to oil biosynthesis in transgenic *Arabidopsis*. *Plant biotechnology journal*, 9, 874-883.

SCHENK, R, U. & HILDEBRANDT, A. C. 1972. Medium and techniques for induction and growth of monocotyledonous and dicotyledonous plant cell cultures. *Canadian Journal of Botany*, 50, 199-204.

SCHWAB, R., OSSOWSKI, S., RIESTER, M., WARTHMANN, N. & WEIGEL, D. 2006. Highly specific gene silencing by artificial microRNAs in *Arabidopsis*. *The Plant Cell Online*, 18, 1121-1133.

SEARCHINGER, T., HEIMLICH, R., HOUGHTON, R. A, DONG, F., ELOBEID, A., FABIOSA, J., TOKGOZ, S., HAYES, D. & YU, T. H. 2008. Use of U.S. Croplands for Biofuels Increases Greenhouse Gases Through Emissions from Land-Use Change. *Science*, 319, 1238-1240.

SHANKLIN, J., SCHWENDER, J. & MICHAEL, T. P. 2009. Project proposal. *Community Sequencing Program*.

SOLDATOVA, O., APCHELIMOV, A., RADUKINA, N., EZHOVA, T., SHESTAKOV, S., ZIEMANN, V., HEDTKE, B., and GRIMM, B. (2005). An *Arabidopsis* mutant that is resistant to the protoporphyrinogen oxidase inhibitor acifluorfen shows regulatory changes in tetrapyrrole biosynthesis. *Molecular Genetics and Genomics* 273, 311-318.

STOMP, A. M. 2005. The duckweeds: a valuable plant for biomanufacturing. *Biotechnology Annual Review*, 11, 69-99.

STOMP, A. M. & RAJBHANDARI, N. 2011. genetically engineered duckweed: EP Patent 1,037,523.

TABEI, Y., NISHIO, T., KURIHARA, K. & KANNO, T. 1994. Selection of Transformed Callus in a Liquid Medium and Regeneration of Transgenic Plants in Cucumber (*Cucumls salvus* L.). *Breeding Science*, 44, 47-51.

TILMAN, D., HILL, J. & LEHMAN, C. 2006. Carbon-negative biofuels from low-input highdiversity grassland biomass. *Science*, 314, 1598-1600.

TOPFER, R., MARTINI, N. & SCHELL, J. 1995. Modification of Plant Lipid Synthesis. *Science*, 268, 681-686.

URBANSKA-WORYTKIEWICZ, K. 1975. Cytological variation within *Lemna* L. *Aquatic Botany*, 1, 377-394.

VARALLYAY, E., BURGYAN, J. & HAVELDA, Z. 2008. MicroRNA detection by northern blotting using locked nucleic acid probes. *Nature protocols*, 3, 190-196.

VARKONYI-GASIC, E., WU, R., WOOD, M., WALTON, E. F., and HELLENS, R. P. (2007). Protocol: a highly sensitive RT-PCR method for detection and quantification of microRNAs. *Plant Methods* 3, 12.

VIGEOLAS, H., MOHLMANN, T., MARTINI, N., NEUHAUS, H. E. & GEIGENBERGER, P. 2004. Embryo-specific reduction of ADP-Glc pyrophosphorylase leads to an inhibition of starch synthesis and a delay in oil accumulation in developing seeds of oilseed rape. *Plant physiology*, 136, 2676-2686.

WANG, R. & BRATTAIN, M. G. 2007. The maximal size of protein to diffuse through the nuclear pore is larger than 60 kDa. *FEBS letters*, 581, 3164-3170.

WANG, W., KERSTETTER, R. A. & MICHAEL, T. P. 2011. Evolution of Genome Size in Duckweeds (*Lemnaceae*). *Journal of Botany*, 2011.

WARTHMANN, N., CHEN, H., OSSOWSKI, S., WEIGEL, D. & NERVE, P. 2008a. Highly specific gene silencing by artificial miRNAs in rice. *PloS One*, 3, e1829.

WARTHMANN, N., LANZ, C. & WEIGEL, D. 2008b. Comparative analysis of the MIR319a microRNA locus in *Arabidopsis* and related Brassicaceae. *Molecular biology and evolution*, 25, 892-902.

WERNER, S., WOLLMANN, H., SCHNEEBERGER, K., and WEIGEL, D. (2010). Structure Determinants for Accurate Processing of miR172a in *Arabidopsis thaliana*. *Current Biology* 20, 42-48.

WESLEY, S. V., HELLIWELL, C. A., SMITH, N. A., WANG, M. B., ROUSE, D. T., LIU, Q., GOODING, P. S., SINGH, S. P., ABBOTT, D. & STOUTJESDIJK, P. A.

2001. Construct design for efficient, effective and high-throughput gene silencing in plants. *The Plant Journal*, 27, 581-590.

XU, J., CUI, W., CHENG, J. & STOMP, A. M. 2011. Production of high-starch duckweed and its conversion to bioethanol. *Biosystems engineering*, 110, 67-72.

XU, J., ZHAO, H., STOMP, A. M. & CHENG, J. J. 2012. The production of duckweed as a source of biofuels. *Biofuels*, 3, 589-601.

YAMAMOTO, Y. T., RAJBHANDARI, N., LIN, X., BERGMANN, B. A., NISHIMURA, Y. & STOMP, A. M. 2001. Genetic transformation of duckweed *Lemna gibba* and *Lemna minor*. *In Vitro Cellular & Developmental Biology—Plant*, 37, 349-353.

YU, W. L., ANSARI, W., SCHOEPP, N., HANNON, M., MAYFIELD, S. & BURKART, M. 2011. Modifications of the metabolic pathways of lipid and triacylglycerol production in microalgae. *Microbial Cell Factories*, 10, 91.

ZAMBRYSKI, P., JOOS, H., GENETELLO, C., LEEMANS, J., VAN MONTAGU, M. & SCHELL, J. 1983. Ti plasmid vector for the introduction of DNA into plant cells without alteration of their normal regeneration capacity. *The EMBO journal*, 2, 2143.

ZHAI, J., JEONG, D-H., DE PAOLI, E., PARK, S., ROSEN, B. D., LI, Y., GONZÁLEZ, A. J., YAN, Z., KITTO, S. L., GRUSAK, M. A., JACKSON, S. A., STACEY, G., COOK, D. R., GREEN, P. J., SHERRIER, D. J. and MEYERS, B. C., 2011. MircoRNSa as master regulators of the plant NB-LRR defense gene family via the production of phased, trans-acting siRNSa. *Genes & Dev.* 25:2540-2553

ABBREVIATIONS

| | |
|---|---|
| μg | micro grams |
| μL | micro Liters |
| μM | micro Molar |
| μm | micrometers |
| amiRNA | artificial micro Ribonucleic Acid |
| Ath | *Arabidopsis thaliana* |
| bp | base pairs |
| cDNA | complementary Deoxyribonucleic Acid |
| $cm^2$ | square centimeters |
| $C_T$ | Cycle Threshold |
| DAPI | 4',6-diamidino-2-phenylindole |
| DNA | Deoxyribonucleic Acid |
| DNase | Deoxyribonuclease |
| dNTP | deoxyribonucleotide Triphosphate |
| dsRNA | double stranded Ribonucleic Acid |
| FA | Fatty Acid |
| g | units of gravity |
| GFP | Green Fluorescent Protein |
| h | hours |
| kb | kilo base |
| kDa | kilo Dalton |
| LB | Left Border |
| Lg | *Lemna gibba* |
| $m^2$ | square meters |
| min | minutes |
| miRNA | micro Ribonucleic Acid |
| mL | mili Liters |
| mM | mili Molar |
| mm | milimeters |
| mRNA | messenger Ribonucleic Acid |
| ng | nanograms |
| °C. | Degree Celsius |
| Osa | *Oryza sativa* |
| PCR | Polymerase Chain Reaction |
| PDS | Phitotene Desaturase |
| pre-amiRNA | artificial micro Ribonucleic Acid precursor |
| PTGS | Post Transcriptional Gene Silencing |
| RB | Right Border |
| RISC | Ribonucleic Acid-induced Silencing Complex |
| RNA | Ribonucleic Acid |
| RNAi | Ribonucleic Acid of interference |
| RNase | Ribonuclease |
| rpm | revolutions per minute |
| rRNA | ribosomal Ribonucleic Acid |
| RT-qPCR | Real Time quantitative Polymerase Chain Reaction |
| s | Seconds |
| SDS-PAGE | Sodium Dodecyl Sulfate Polyacrylamide Gel Electrophoresis |
| shRNA | small hairpin Ribonucleic Acid |
| siRNA | small interference Ribonucleic Acid |
| sRNA | small Ribonucleic Acid |
| TAG | Tryacylglicerid |
| Tail-PCR | Thermal Asymmetric Interlaced Polymerase Chain Reaction |
| UV | Ultraviolet |
| V | Volts |
| w/v | weight/volume |

The invention claimed is:

1. A method for stably transforming *Lemna minor* duckweed with a nucleic acid, the method comprising:

(a) inoculating, in liquid infection medium that comprises magnesium, a plant metabolizable sugar, and acetosyringone, an actively growing *Lemna minor* duckweed callus with an engineered *Agrobacterium* that comprises a nucleic acid of interest, a selectable marker gene that confers resistance to a selection substance, and a visible reporter gene encoding a protein that is visualized without killing inoculated callus, thereby producing inoculated callus;

(b) culturing inoculated callus on semi-solid nodule production medium that comprises acetosyringone, and then culturing inoculated callus on semi-solid selection medium that comprises (i) the selection substance and (ii) an antibiotic, thereby producing cultured, inoculated callus;

(c) selecting, from cultured, inoculated callus of (b), transformed callus based on expression of the visible reporter protein in the transformed callus;

(d) culturing, in liquid selection medium that comprises the selection substance and the antibiotic, selected callus of (c); and (e) culturing callus cultured in (d) on semi-solid selection medium that comprises the selection substance and the antibiotic, thereby producing genetically engineered progeny *Lemna minor* duckweed comprising the nucleic acid of interest.

2. The method of claim 1, wherein the *Agrobacterium* is an *Agrobacterium tumefaciens*.

3. The method of claim 1, wherein the diameter of the actively growing *Lemna minor* duckweed callus of (a) is about 3 to 5 mm.

4. The method of claim 1, wherein the magnesium comprises magnesium sulfate and the plant metabolizable sugar comprises sucrose.

5. The method of claim 1, wherein the selection substance is DL-phosphinothricin.

6. The method of claim 1, wherein the visible reporter gene encodes green fluorescent protein.

7. The method of claim 1, wherein the semi-solid nodule production medium of (b) further comprises Murashige and Skoog basal salts, sucrose, 2,4-dichlorophenoxyacetic acid, and 6-benzylaminopurine.

8. The method of claim 1, wherein cultured, inoculated callus of (b) is cultured for about 4 to 7 days on the semi-solid selection medium.

9. The method of claim 1, wherein the semi-solid selection medium of (b) further comprises the selection substance, the antibiotic, basal salts and sucrose.

10. The method of claim 9, wherein the selection substance comprises DL-phosphinothricin, and the antibiotic comprises carbenicillin and cefotaxamin.

11. The method of claim 1, wherein the visible reporter gene encodes a fluorescent protein, and wherein (c) comprises selecting fluorescent cells using fluorescent microscopy.

12. The method of claim 1, wherein the selected callus of (c) is cultured in liquid selection medium for about 3 to 4 weeks.

13. The method of claim 1, wherein the liquid selection medium of (d) further comprises basal salts and sucrose.

14. The method of claim 13, wherein the selection substance comprises DL-phosphinothricin, and the antibiotic comprises carbenicillin and cefotaxamin.

15. The method of claim 1, wherein (e) comprises culturing callus cultured in (d) on the semi-solid selection medium until genetically engineered progeny *Lemna minor* duckweed is visible.

16. The method of claim 1, wherein the semi-solid selection medium of (e) further comprises basal salts and sucrose.

17. The method of claim 16, wherein the selection substance comprises DL-phosphinothricin, and the antibiotic comprises carbenicillin and cefotaxamin.

18. The method of claim 1, wherein the nucleic acid of interest comprises a promoter operably linked to a nucleic acid that encodes a protein of interest or an artificial microRNA.

* * * * *